US012624102B2

(12) United States Patent
Liu

(10) Patent No.: US 12,624,102 B2
(45) Date of Patent: May 12, 2026

(54) CD147 CHIMERIC ANTIGEN RECEPTORS AND METHODS OF USE

(71) Applicant: Rutgers, The State University of New Jersey, New Brunswick, NJ (US)

(72) Inventor: Dongfang Liu, Millburn, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1185 days.

(21) Appl. No.: 17/438,741

(22) PCT Filed: Feb. 28, 2020

(86) PCT No.: PCT/US2020/020436
§ 371 (c)(1),
(2) Date: Sep. 13, 2021

(87) PCT Pub. No.: WO2020/190483
PCT Pub. Date: Sep. 24, 2020

(65) Prior Publication Data
US 2022/0152106 A1 May 19, 2022

Related U.S. Application Data

(60) Provisional application No. 62/819,403, filed on Mar. 15, 2019.

(51) Int. Cl.
| | |
|---|---|
| *C07K 16/28* | (2006.01) |
| *A61K 39/00* | (2006.01) |
| *A61K 40/11* | (2025.01) |
| *A61K 40/15* | (2025.01) |
| *A61K 40/31* | (2025.01) |
| *A61K 40/42* | (2025.01) |
| *A61K 45/06* | (2006.01) |
| *A61P 35/00* | (2006.01) |
| *C07K 14/725* | (2006.01) |
| *C12N 5/0783* | (2010.01) |

(52) U.S. Cl.
CPC .......... *C07K 16/2803* (2013.01); *A61K 40/11* (2025.01); *A61K 40/15* (2025.01); *A61K 40/31* (2025.01); *A61K 40/421* (2025.01); *A61K 45/06* (2013.01); *A61P 35/00* (2018.01); *C07K 14/7051* (2013.01); *C12N 5/0636* (2013.01); *A61K 2039/505* (2013.01); *A61K 2239/13* (2023.05); *A61K 2239/31* (2023.05); *A61K 2239/38* (2023.05); *A61K 2239/53* (2023.05)

(58) Field of Classification Search
CPC ................ A61K 40/31; A61K 2239/13; A61K 2239/17; A61K 2239/21; A61K 2239/22; A61K 40/11; A61K 40/15; A61K 40/17
See application file for complete search history.

(56) References Cited

U.S. PATENT DOCUMENTS

| | | | |
|---|---|---|---|
| 8,618,264 B2 | 12/2013 | Cunningham et al. | |
| 2011/0200627 A1* | 8/2011 | Cunningham | ............ A61P 9/00 |
| | | | 530/387.2 |
| 2016/0361360 A1 | 12/2016 | Chang et al. | |
| 2018/0148508 A1 | 5/2018 | Wang et al. | |
| 2018/0303952 A1* | 10/2018 | Sagert | ............. A61K 47/68031 |

FOREIGN PATENT DOCUMENTS

| | | | | |
|---|---|---|---|---|
| WO | WO 1995/03828 | 2/1995 | | |
| WO | WO 2010/036460 A2 | 4/2010 | | |
| WO | WO-2016120220 A1 * | 8/2016 | ............. | A61K 35/17 |
| WO | WO 2016/210447 A1 | 12/2016 | | |
| WO | WO-2017037634 A1 * | 3/2017 | ............. | A61P 35/00 |
| WO | WO 2018/165619 | 9/2018 | | |

OTHER PUBLICATIONS

Xiong et al (Molecular Therapy, 2018, vol. 26, pp. 963-975). (Year: 2018).*
Roybal et al (Cell, 2016, vol. 164, pp. 770-779) (Year: 2016).*
Gargett et al., "The inducible caspase-9 suicide gene system as a "safety switch" to limit on-target, off-tumor toxicities of chimeric antigen receptor T cells," *Frontiers in Pharmacology*, vol. 5, Article 235, 2014 (7 pages).
Stavrou et al., "A Rapamycin-Activated Caspase 9-Based Suicide Gene," *Molecular Therapy*, vol. 26, No. 5, pp. 1266-1276, 2018.
Xin et al., "CD147/EMMPRIN overexpression and prognosis in cancer: A systematic review and meta-analysis," *Scientific Reports*, vol. 6, Article 32804, 2016 (12 pages).
Zhang et al., "Doxycycline Inducible Chimeric Antigen Receptor T Cells Targeting CD147 for Hepatocellular Carcinoma Therapy," *Front Cell Dev Biol.*, vol. 7, Article 233, 2019 (13 pages).
Halim et al., "Pre-clinical development of chimeric antigen receptor T-cell immunotherapy: Implications of design for efficacy and safety," *Best Practice & Research Clinical Haematology* 31(2):117-125, Jun. 2018.

* cited by examiner

*Primary Examiner* — Karen A. Canella
(74) *Attorney, Agent, or Firm* — Klarquist Sparkman, LLP

(57) ABSTRACT

Modified single chain variable fragments (scFv) that specifically bind CD147 are provided. Also provided are chimeric antigen receptors (CARs) including the modified CD147 scFv, nucleic acids encoding the CARs, vectors including the nucleic acids encoding the CARs, and immune cells expressing the CARs. Methods of treating a subject with cancer including administering to the subject an immune cell expressing a disclosed CD147-CAR are also provided.

22 Claims, 39 Drawing Sheets

Specification includes a Sequence Listing.

FIG. 5D
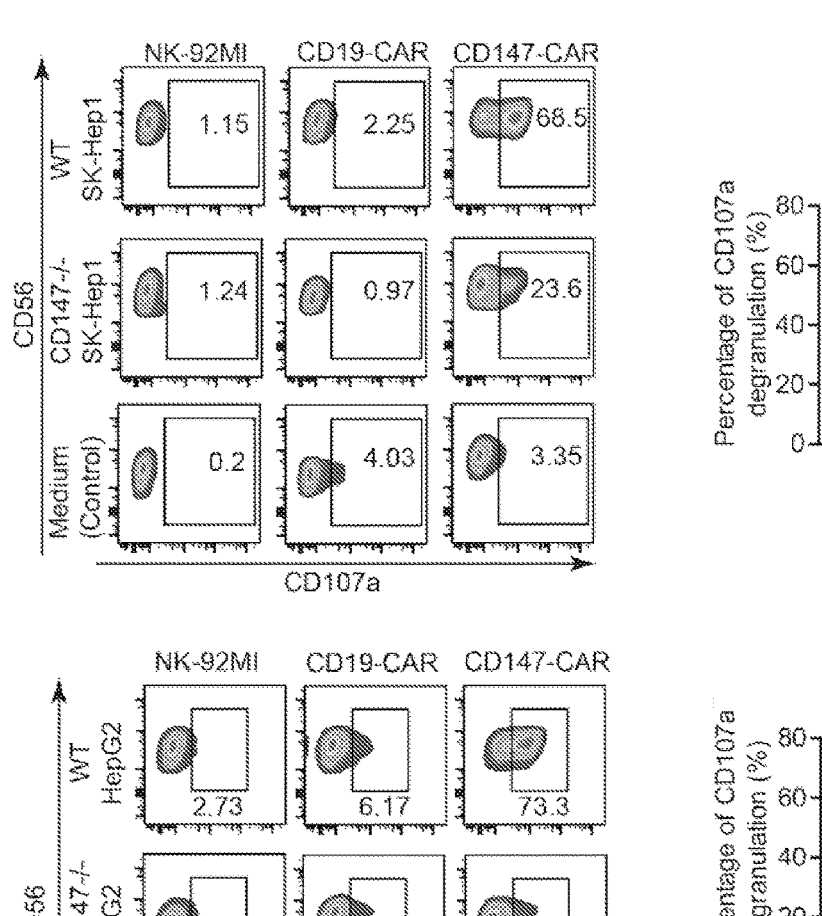
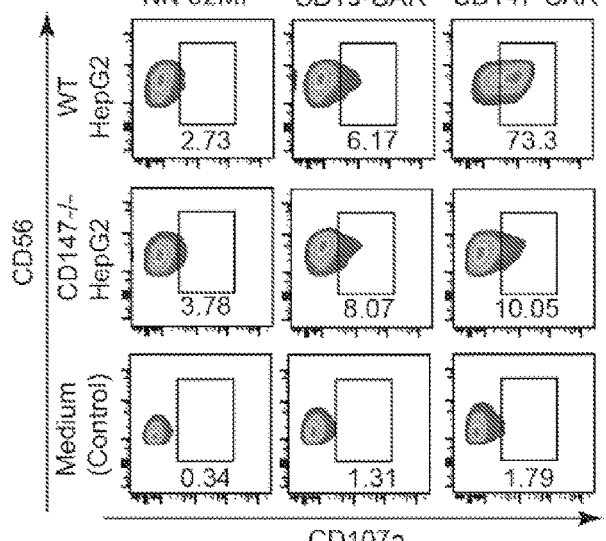
FIG. 5F
FIG. 5E
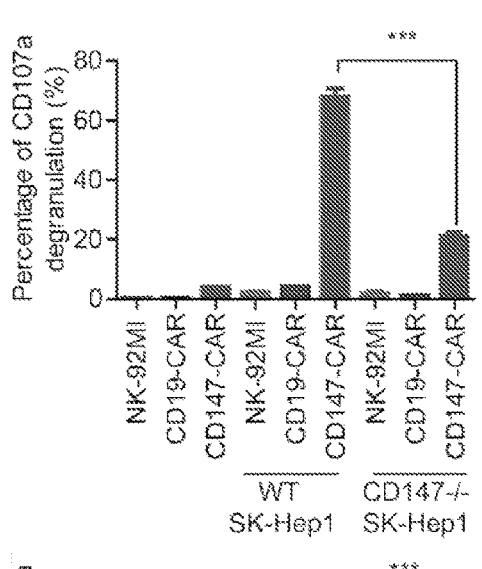
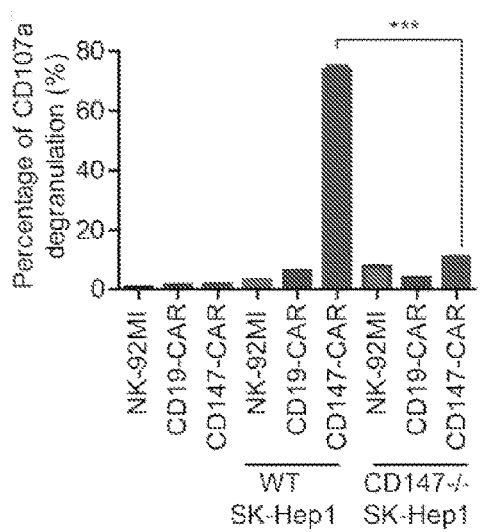
FIG. 5G

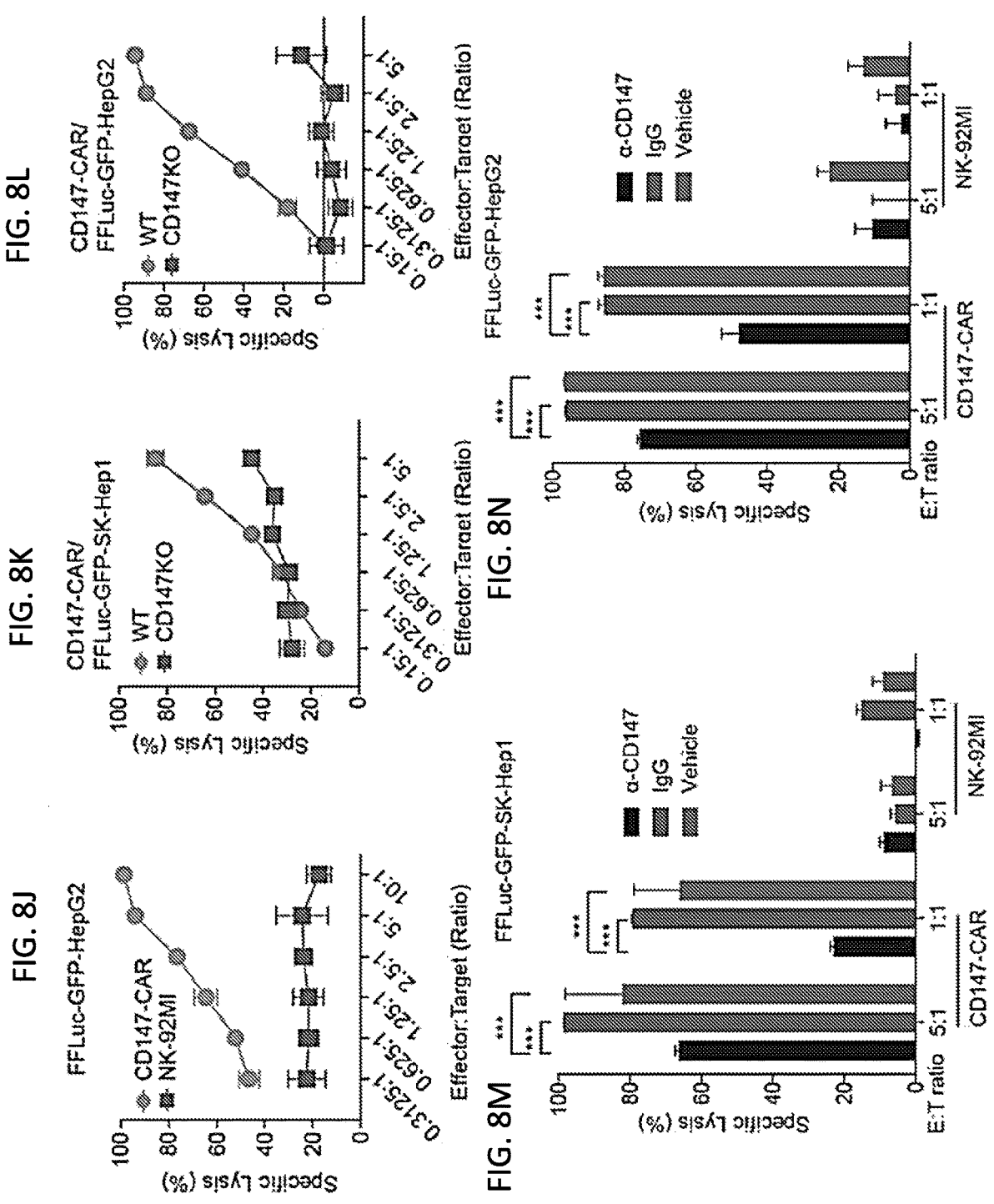

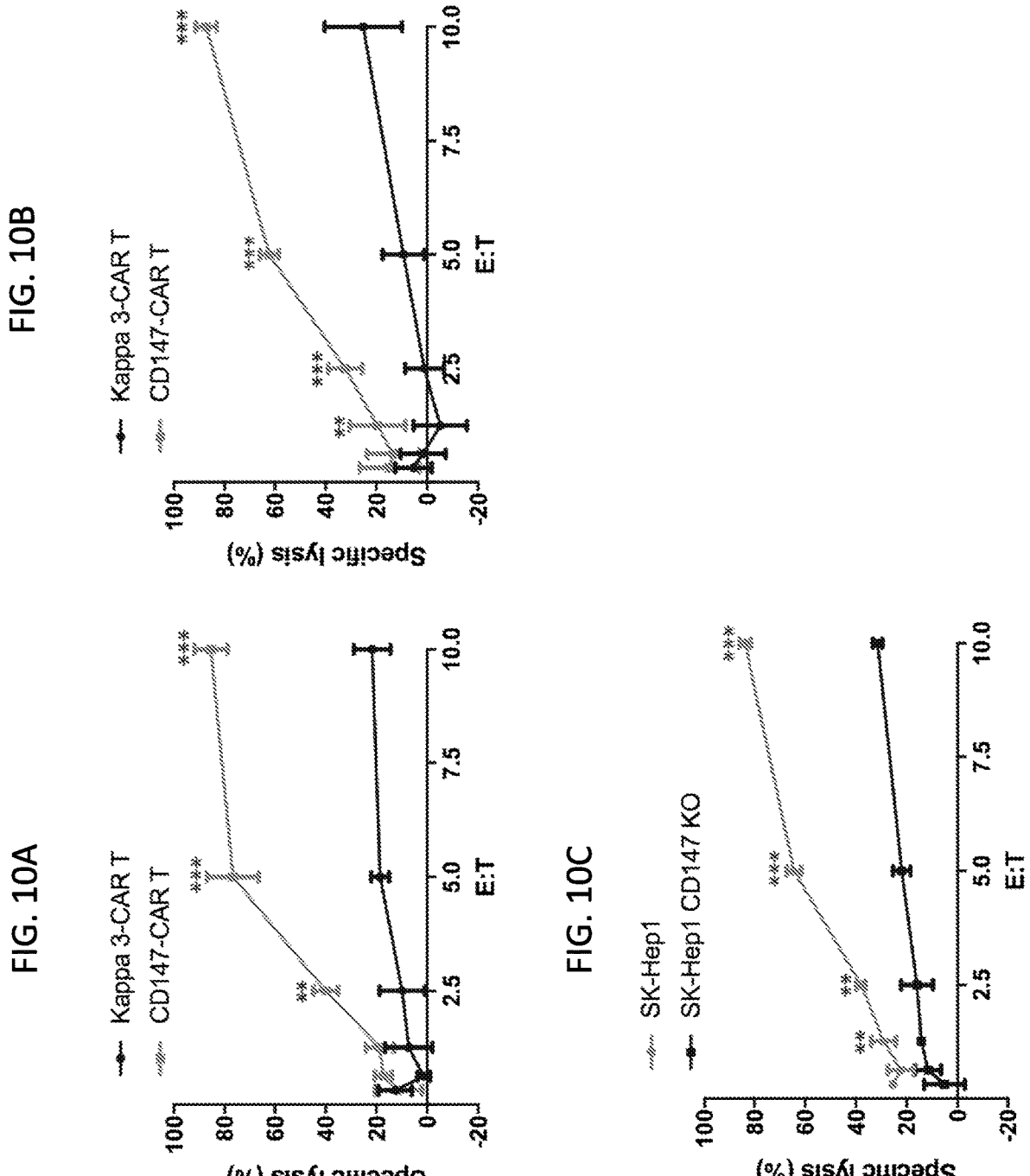

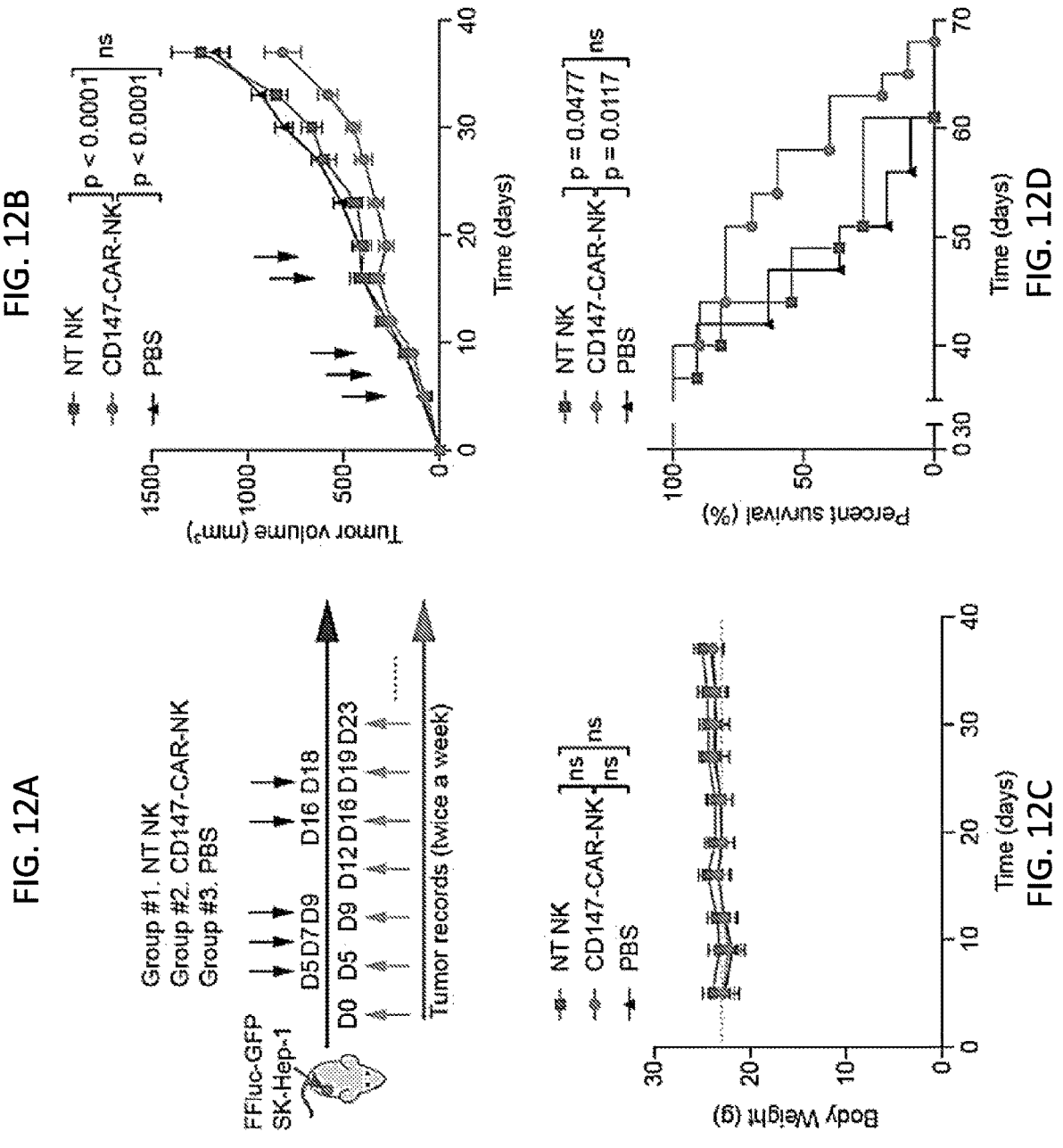

FIG. 13

FIG. 17A                    FIG. 17B
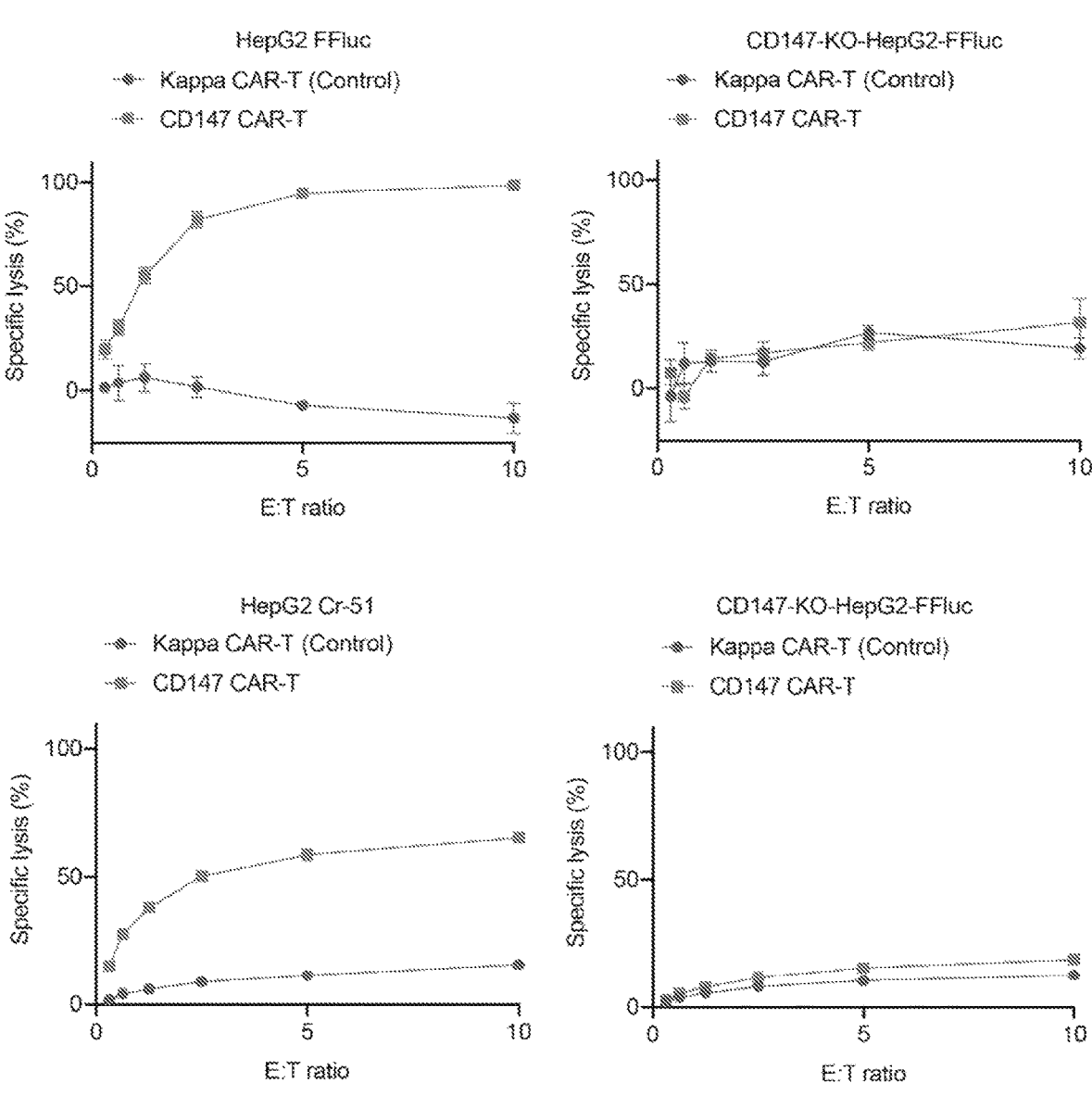
FIG. 17C                    FIG. 17D

| Start at 0 hour | After 3 hour |

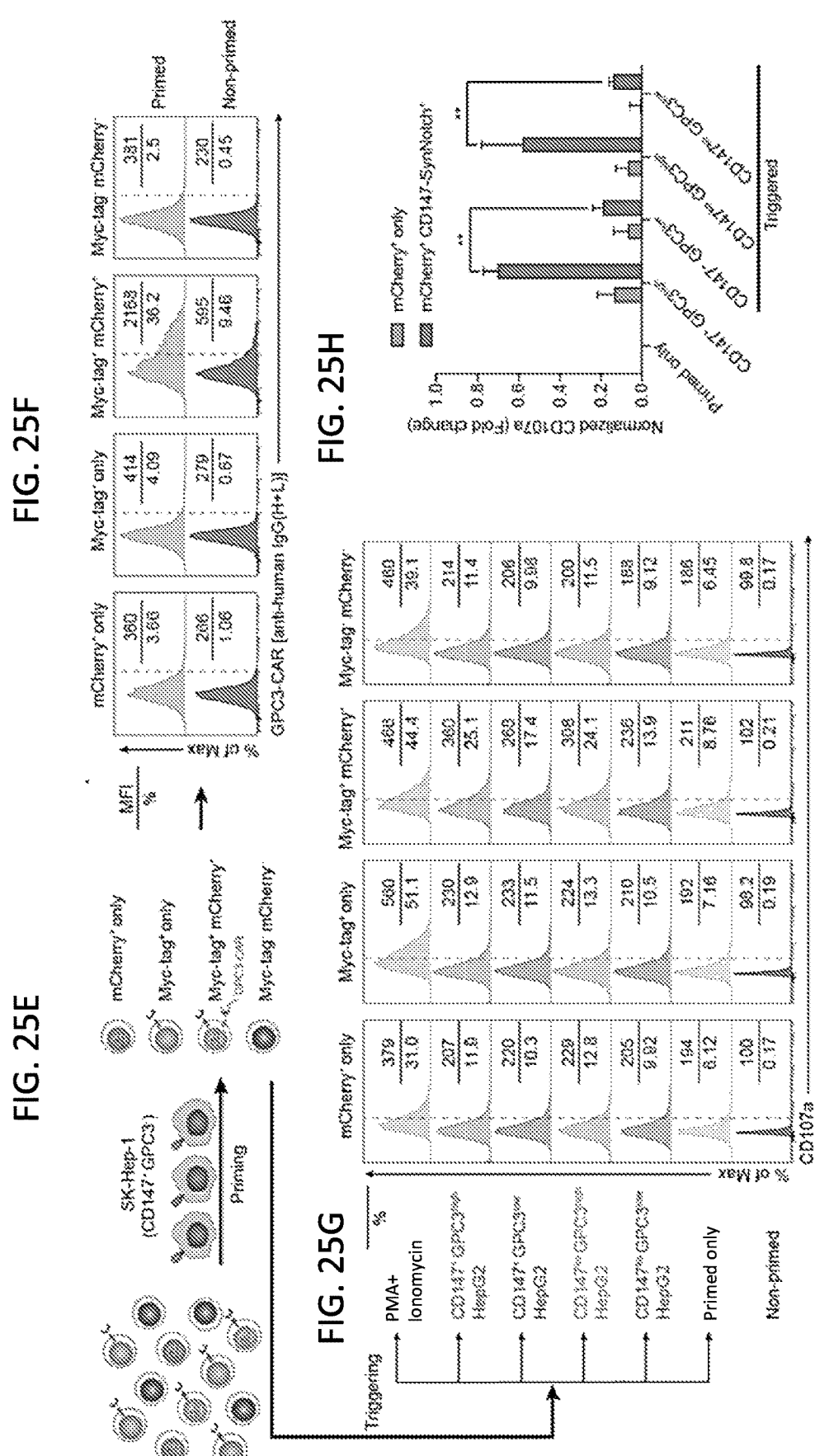

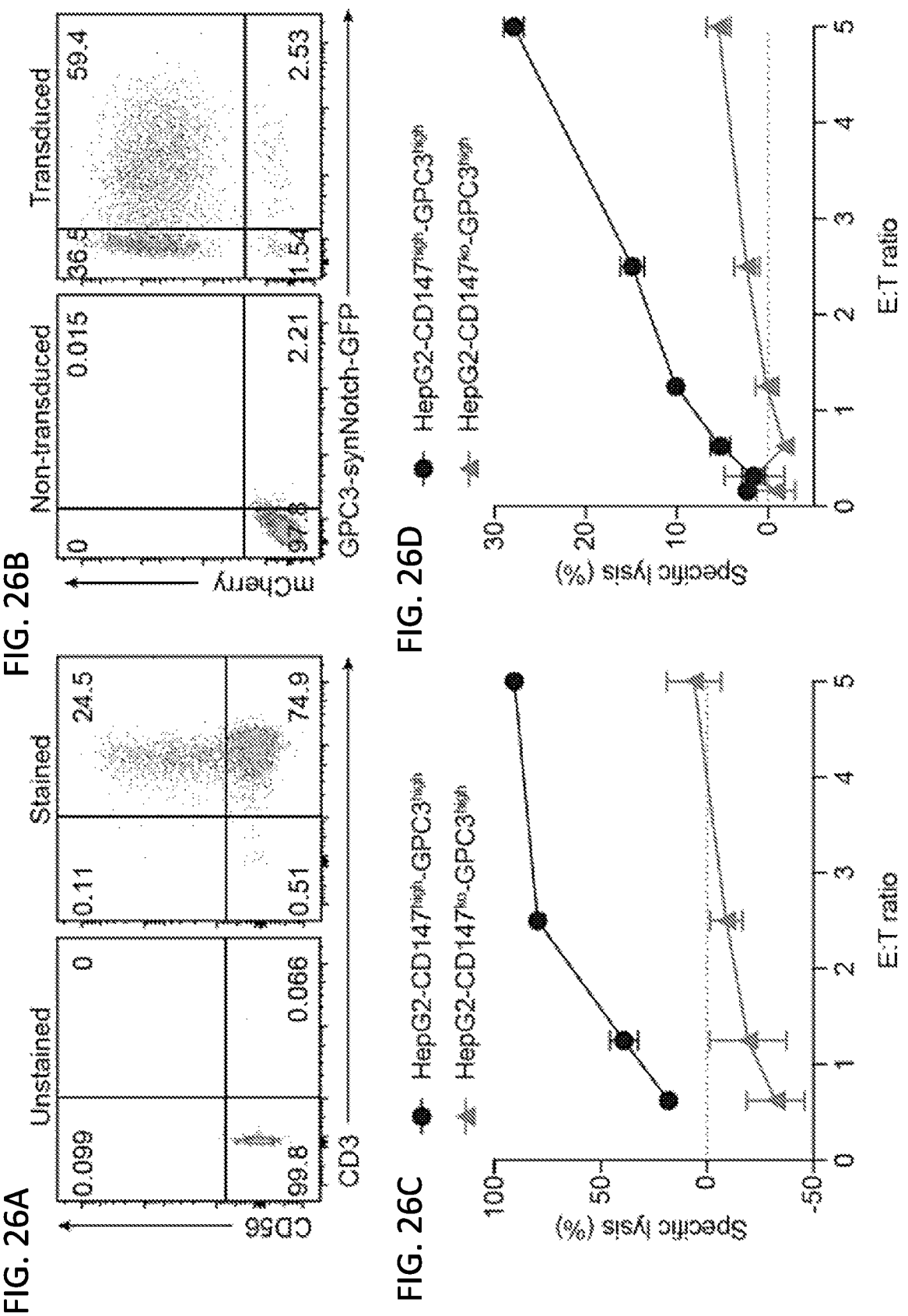

CD147 CHIMERIC ANTIGEN RECEPTORS AND METHODS OF USE

CROSS REFERENCE TO RELATED APPLICATIONS

This application is the § 371 U.S. National Stage of International Application No. PCT/US2020/020436, filed Feb. 28, 2020, which was published in English under PCT Article 21(2), which in turn claims the benefit of U.S. Provisional Patent Application No. 62/819,403, filed Mar. 15, 2019, which is incorporated herein by reference in its entirety.

ACKNOWLEDGMENT OF GOVERNMENT SUPPORT

This invention was made with government support under grant numbers HL150852 and AI130197 awarded by the National Institutes of Health. The government has certain rights in the invention.

FIELD

This disclosure related to immunotherapies, particularly chimeric antigen receptors targeting CD147 and their use for treating cancer.

SEQUENCE LISTING INCORPORATION BY REFERENCE

The Sequence Listing is submitted as an ASCII text file in the form of the file named Sequence_Listing-2.txt, which was created on Dec. 15, 2025, and is 61,738 bytes, which is incorporated by reference herein.

BACKGROUND

Liver cancer is the second most common cause of cancer-related death worldwide. The burden of liver cancer is projected to be over 1 million cases by 2030. Liver cancer ranks fifth in terms of global cases and second in terms of deaths for males. More than half a million patients die from hepatocellular carcinoma (HCC) each year.

Primary liver cancer includes hepatocellular carcinoma (HCC), intrahepatic cholangiocarcinoma (iCCA), fibrolamellar carcinoma, and hepatoblastoma. HCC and iCCA are the most common primary liver cancers, which account for more than 99% of primary liver cancer cases. HCC alone (nearly 800,000 new cases per year) accounts for 90% of all cases of primary liver cancer. Currently, there is no effective therapy available to treat HCC. Sorafenib (CheckMate-040, a multi-kinase inhibitor widely used for advanced HCC patients with low efficacy and severe side effects) is a first-line standard systemic agent for HCC. Currently, PD-1 blockade Opdivo (Nivolumab) has been approved by the US Food and Drug Administration (FDA) as a second line treatment strategy for patients with HCC who have been previously treated with Sorafenib. Clinical trials testing PD-1 blockade as a first-line treatment for HCC are underway. Meanwhile, various clinical trials using PD-1 or PD-L1 blockades in combination with other interventions are ongoing as well. For example, a study evaluating anti-PD-1 antibody in combination with anti-CTLA-4 antibody in patients with resectable and potentially resectable HCC is being tested in clinical trials (NCT03222076).

Chimeric antigen receptor (CAR)-modified T cell therapy has become a promising immunotherapeutic strategy for the treatment of various blood cancers. Despite recent advances in CAR-modified T cell immunotherapy in blood cancers, high costs and severe toxicity have hindered its widespread use. Meanwhile, CAR-T cells face additional challenges during the targeting of solid tumors, such as maintaining durable proliferation and persistence in the tumor microenvironment. An additional challenge for CAR-mediated immunotherapy for liver cancer is to find an effective target.

SUMMARY

CD147 is expressed on different cell types (e.g., hematopoietic, epithelial, and endothelial cells) at varying levels. However, CD147 is significantly upregulated in disease states, such as in HCC, breast cancer, bladder cancer, colorectal cancer, ovarian cancer, melanoma, and osteosarcoma. CARs that specifically target cells expressing CD147 are provided. These CARs can be used in immunotherapy of cancers expressing or overexpressing CD147.

Disclosed herein are modified single-chain variable fragments (scFvs) that specifically bind CD147. In some embodiments, the scFv has an amino acid sequence that includes the variable heavy chain (VH) domain complementarity determining region 1 (CDR1), CDR2 and CDR3 amino acid sequences of SEQ ID NO: 8 and the variable light chain (VL) domain CDR1, CDR2 and CDR3 amino acid sequences of SEQ ID NO: 9. In some examples, the scFv has at least 90% sequence identity to the amino acid sequence of SEQ ID NO: 2 or includes or consists of the amino acid sequence of SEQ ID NO: 2. Also provided are nucleic acids that encode the modified CD147 scFv, such as a nucleic acid with at least 90% sequence identity to the nucleic acid molecule of SEQ ID NO: 1, or include or consist of the nucleic acid sequence of SEQ ID NO: 1 and vectors including the nucleic acid sequence. In additional embodiments, provided are vectors encoding the modified CD147 scFv (such as SEQ ID NO: 1), which further comprise an inducible promoter or enhancer nucleic acid molecule operably linked to the CD147 scFv nucleic acid molecule. In some examples, the enhancer nucleic acid is a Gal4 upstream activation sequence (UAS) that is operably linked to a nucleic acid encoding the CD147 scFv. In another example, the vector is a synNotch construct, for example a vector including the nucleic acid sequence of the modified CD147 scFv nucleic acid molecule (e.g., SEQ ID NO: 1) linked to synNotch and a Gal4-VP64 encoding sequence (e.g., SEQ ID NO: 17).

Also provided are CARs that include a modified CD147 scFv provided herein, a hinge domain, a transmembrane domain, an intracellular domain comprising one or more co-stimulatory molecule intracellular domains and an intracellular signaling domain. In one embodiment, the CD147-CAR includes a modified CD147 scFv provided herein, an IgG1 hinge domain, a CD28 transmembrane domain, CD28 and 4-1BB co-stimulatory domains, and a CD3 signaling domain. In some examples, the CD147-CAR includes an amino acid sequence with at least 90% identity to the amino acid sequence of SEQ ID NO: 5 or includes or consists of the amino acid sequence of SEQ ID NO: 5.

In some embodiment, the CD147-CAR further includes an inducible suicide molecule, such as caspase 9. In some examples, expression of the suicide molecule is induced by tetracycline, doxycycline, or rapamycin. In one example, the CD147-CAR with an inducible suicide gene includes an amino acid sequence with at least 90% identity to the amino acid sequence of SEQ ID NO: 7 or includes or consists of the amino acid sequence of SEQ ID NO: 7. The CD147-CAR may further include a cytokine receptor intracellular domain, such as an interleukin-15 receptor intracellular domain (e.g., SEQ ID NO: 12), an interleukin-12 receptor intracellular domain or an interleukin 18 receptor intracellular domain.

Also provided are nucleic acids encoding the CD147-CARs disclosed herein, and vectors including the nucleic acids (such as a viral vector). In some examples, the CD147-CAR is encoded by a nucleic acid sequence with at least 90% identity to the nucleic acid sequence of SEQ ID NO: 4 or SEQ ID NO: 6. In other examples, the CD147-CAR is encoded by a nucleic acid that includes or consists of the nucleic acid sequence of SEQ ID NO: 4 or SEQ ID NO: 6.

In additional embodiments, provided are vectors encoding a CD147-CAR (such as SEQ ID NO: 4 or SEQ ID NO: 6), further comprising an inducible promoter or enhancer nucleic acid molecule operably linked to the CD147-CAR nucleic acid molecule. In some examples, the enhancer nucleic acid is a Gal4 upstream activation sequence (UAS) that is operably linked to a nucleic acid encoding the CD147-CAR (e.g., SEQ ID NO: 14). In one example, the vector includes the CD147-CAR in a synNotch construct, for example a vector including the nucleic acid sequence of SEQ ID NO: 15. In other examples, the CD147-CAR nucleic acid molecule (e.g., SEQ ID NO: 1) is linked to synNotch and a Gal4-VP64 encoding sequence (e.g., SEQ ID NO: 17).

Also provided are T cells, natural killer (NK) cells, natural killer T (NKT) cells, double negative T (DNT) cells (CD3$^+$ CD4$^-$CD8$^-$), neutrophils, or macrophages expressing the disclosed scFvs and/or CARs, such as T cells, NK cells, NKT cells, DNT cells, neutrophils, or macrophages comprising a nucleic acid encoding a disclosed CD147 scFv or CD147-CAR or a vector encoding a disclosed CD147 scFv or CD147-CAR. In some examples, the NK cells are NK-92 or NK-92MI cells. Methods of producing cells expressing the CARs, including but not limited to CD147-CAR-NK cells, CD147-CAR-T cells, or CD147-CAR-macrophages are provided. These methods include transducing or transfecting T cell, NK cells, NKT cells, DNT cells, neutrophils, or macrophages with a vector encoding a disclosed CAR.

In further embodiments, provided are T cells, NK cells, NKT cells, DNT cells, neutrophils, or macrophages expressing a CD147-CAR operably linked to an activator of the inducible promoter or enhancer element. In some examples, the T cells, NK cells, NKT cells, DNT cells, neutrophils, or macrophages further express a nucleic acid encoding an anti-GPC3 specific binding agent (such as an anti-GPC3 scFv) operably linked to an activator of the inducible promoter or enhancer element. In other embodiments, provided are T cells, NK cells, NKT cells, DNT cells, neutrophils, or macrophages expressing a CD147 scFv operably linked to an inducible promoter or enhancer element and further comprising a nucleic acid molecule encoding an anti-GPC3 chimeric antigen receptor operably linked to the inducible promoter or enhancer.

Disclosed herein are methods for treating a subject with cancer, for example by administering a CAR-expressing NK cell, T cell, NKT cell, DNT cell, neutrophil, or macrophage disclosed herein (e.g., CD147-CAR NK cell, CD147-CAR-T cell, or CD147-CAR macrophage) to the subject. In some examples, the subject has a cancer that expresses CD147. In particular non-limiting examples, the subject has hepatocellular carcinoma, neuroblastoma, breast cancer, pancreatic cancer, leukemia, lymphoma, multiple myeloma, colorectal cancer, lung cancer, melanoma, renal cell carcinoma, sarcoma, or nasopharyngeal carcinoma.

The foregoing and other features of the disclosure will become more apparent from the following detailed description, which proceeds with reference to the accompanying figures.

BRIEF DESCRIPTION OF THE DRAWINGS

FIG. 1A shows prognostic value of the CD147 upregulated expression for overall survival of human cancer patients from TCGA datasets. Survival curves (top panel) of different patient populations based on relative CD147 high and low expression (bottom panel). The data of LUAD (Lung adenocarcinoma), SKCM (Skin Cutaneous Melanoma), LIHC (Liver hepatocellular carcinoma), and LGG (Brain Lower Grade Glioma) were collected for analysis. FIG. 1B shows comparison of CD147 expression between normal tissue (NT) and tumor sample (TP) in multiple cancer types from TCGA datasets. Data represent the mean±SEM of three separate experiments. Unpaired Student's t test were employed. *p<0.05, p<0.01, **p<0.001 and n.s (no significant difference). According to the TCGA database, the full name of each cancer type is: BRCA (Breast invasive carcinoma), CHOL (Cholangiocarcinoma), GBM (Glioblastoma multiforme), LGG (Brain Lower Grade Glioma), HNSC (Head and Neck squamous cell carcinoma), KICH (Kidney Chromophobe), KIPAN Pan-kidney cohort (KICH+KIRC+KIRP), KIRP (Kidney renal papillary cell carcinoma), LIHC (Liver hepatocellular carcinoma), LUAD (Lung adenocarcinoma), LUSC (Lung squamous cell carcinoma), PRAD (Prostate adenocarcinoma), UCEC (Uterine Corpus Endometrial Carcinoma). FIG. 1C shows Western blot analysis of CD147 in HCC cell lines. 1×10$^6$ cells of various cell lines were lysed in 200 μl RIPA buffer and mixed with 50 μl 5×SDS loading buffer before loading onto an SDS-PAGE independently. Mouse anti-Human CD147 (HIM6, Mouse IgG1) was used for Western blot analysis. Anti-GAPDH was used as a loading control. FIG. 1D shows CD147 in HCC cell lines (SK-Hep1 and HepG2). SK-Hep1 and HepG2 (1×10$^6$ cells) were stained with 2 μg FITC-mouse anti-human CD147 (anti-CD147) or 2 μg FITC-isotype mouse IgG1 (Isotype, Kappa). After incubation and washing, samples were analyzed by flow cytometry. Number represents mean fluorescence intensity (MFI) of each sample. FIG. 1E is a series of panels showing histopathology analysis of CD147 antigen expression on human HCC tumor isolated from PDX mouse model. Representative H&E (top row) and CD147 IHC staining (middle row) of tumor samples from different patient-derived xenograft (PDX) mice treated with PBS, NK-92MI, and CD147-CAR NK-92MI, respectively. Bottom row shows IHC staining without the primary antibody. Scale bars represent 50 μm. Data are representative of three independent experiments.

FIG. 2A shows the schematic design of a CD147-specific CAR based on the SFG retroviral vector. The construct includes a CD147-specific single chain antibody fragment (modified scFv, from clone 5F6, mIgG1), a human IgG1 CH2CH3 hinge region and CD28 transmembrane region, followed by the intracellular domains of co-stimulatory CD28, 4-1BB and intracellular domain of CD32. FIG. 2B shows flow cytometric analysis of CAR expression and CD56 on the surface of parental NK-92MI and CD147-CAR-NK-92MI. Data are representative of at least three experiments. FIG. 2C shows Western blot analysis of CAR expression in parental NK-92MI and CD147-CAR-NK-92MI cells by anti-human CD3ζ-specific antibody for detection of endogenous CD147 and CD147-CAR fusion protein. FIG. 2D shows NK activation and inhibition markers in parental NK-92MI, CAR-CD19 (4-1BB)-NK-92MI, and CD147-CAR-NK-92MI cells. Each data represents at least three or four experiments. Number in the flow graph represents mean fluorescence intensity (MFI) of each sample. FIG. 2E shows flow cytometric analysis of expression of CARs on CD19-CAR-NK-92MI and CD147-CAR-NK-92MI using goat anti-human IgG (H+L). Wild type NK-92MI cells were used as control. FIG. 2F shows flow cytometric analysis of expression of CD147 on NK-92MI, CD19-CAR-NK-92MI, and CD147-CAR-NK-92MI.

FIG. 3A shows representative flow cytometric data illustrating CD107a degranulation on NK-92MI, CD19-4-1BB-CAR, CD19-CD28-CAR and CD147-CAR after 10 hours with medium (control), SK-Hep1, and HepG2. The ratio of effector and target is 1:1.2. Cells were gated for CD56 positive subsets for quantifying surface CD107a expression. FIG. 3B shows quantitative data for percentage of surface CD107a expression on CD147-CAR-NK-92MI cells upon different stimulations, as indicated. Cytokine TNF-alpha (FIG. 3C) and IFN-gamma (FIG. 3D) production by CD147-CAR-NK-92MI, CD19-4-1BB-CAR-NK-92MI, CD19-CD28-CAR-NK-92MI, and wild-type NK-92MI stimulated by different conditions. The NK-92MI cells were co-cultured with SK-Hep1 cells at an effector/target ratio of 1:1 or medium for 12 hours. Phorbol-12-myristate-13-acetate (PMA)/ionomycin (IONO) were used for a positive control. The ratios of cytokine release were calculated by the following equation: sample value/average of positive control value×100(%). Data were pooled from at least three or four experiments.

FIG. 4A is representative flow cytometric staining of surface CD147 molecules on Huh7 (left) and HCO2 (right) cell lines. FIG. 4B is a graph showing cytotoxicity of CD147-CAR-NK-92MI measured by a standard 4-hr $^{51}$Cr release assay. CD147-positive Huh7 cells were used as the CD147-CAR-NK-92MI susceptible target cells. Wild type NK-92MI was used as control. FIG. 4C is a graph showing cytotoxicity of CD147-CAR-NK-92MI measured by a standard 4-hr $^{51}$Cr release assay. CD147-positive HCO2 cells were used as the CD147-CAR-NK-92MI susceptible target cells. Wild type NK-92MI was used as control. Data represent the mean±SEM from three independent experiments. *p<0.05, p<0.01, and *p<0.001.

FIGS. 5A-5G show activation of CD147-CAR-NK-92MI cells upon CD147 positive target cell stimulation. FIG. 5A shows representative data showing the percentage of surface CD107a expression on CD147-CAR-NK-92MI cells upon different stimulation, as indicated. CD147-CAR-NK-92MI cells were stimulated with SK-Hep1 or HepG2 cells for 4 hours. To block the interaction between CD147-CAR and CD147 molecules, 5 μg mouse-anti-human CD147 (HIM6) was added into the mixture of effector and target cells. As a control, 5 μg Isotype-Mouse IgG (IgG) or PBS (Vehicle control group) was used, as indicated. FIGS. 5B and 5C are graphs showing quantitative data for the percentage of surface CD107a staining on CD147-CAR-NK-92MI cells stimulated with CD147 positive SK-Hep1 (FIG. 5B) and CD147 positive HepG2 (FIG. 5C) cell lines. Wild type NK-92MI cells alone and CD147-CAR-NK-92MI cells alone were used as the control, as indicated. FIG. 5D shows representative data showing the percentage of surface CD107a expression on CD147-CAR-NK-92MI cells stimulated with CD147 positive wild type (WT) SK-Hep1 cell line (top panel) and CD147-knockout (CD147$^{-/-}$) SK-Hep1 cell line (middle panel). The culture medium only group was used as a control. Naive NK-92MI and 4-1BB-CD19-CAR (CD19-CAR) was used as the control effector cell. FIG. 5E shows quantitative data for the percentage of surface CD107a staining on CD147-CAR-NK-92MI cells stimulated with CD147 positive SK-Hep1 (WT) and CD147-Knock out SK-Hep1 (CD147$^{-/-}$) cell lines, respectively. FIG. 5F shows representative data showing the percentage of surface CD107a expression on CD147-CAR-NK-92MI cells stimulated with a CD147 positive wild type (WT) HepG2 cell line (top panel) and a CD147-knockout HepG2 cell line (middle panel). The culture medium only group was used as a control. Naive and CD19-4-1BB-CAR-NK-92MI (CD19-CAR) was used as the control effector cell. FIG. 5G shows quantitative data for the percentage of surface CD107a staining on CD147-CAR-NK-92MI cells stimulated with CD147 positive HepG2 (WT) and CD147-Knock out HepG2 (CD147$^{-/-}$) cell lines, respectively. The ratio of effector and target is 1:1.2. CD147-CAR-NK-92MI cells were gated by CD56 antibody surface staining. NK degranulation was measured by the CD107a surface staining by flow cytometry. Data represent the mean±SEM of three separate experiments. *p<0.05, p<0.01, and *p<0.001.

FIGS. 8A-8N show CD147-CAR-T and -NK cells specifically kill CD147-positive tumor cells in vitro. FIG. 8A shows cytotoxicity of primary CD147-CAR-T cells measured by FFLuc reporter assays. CD147-positive FFLuc-GFP-SK-Hep1 were used as the CD147-CAR-T susceptible target cells. Kappa-CAR T cells were used as control groups for each experiment. FIGS. 8B and 8C show significantly decreased cytotoxicity of CD147-CAR-T cells using knockout-CD147 FFLuc-GFP-SK-Hep1 cell line and HepG2 cell line by FFLuc reporter assays. Data represent the mean±SEM from three independent experiments. FIG. 8D shows cytotoxicity of primary CD147-CAR-NK cells measured by the 4-h standard $^{51}$Cr release assays. CD147-positive FFLuc-GFP-SK-Hep1 were used as the CD147-CAR-T susceptible target cells. Kappa-CAR T cells were used as a control group for each experiment. FIGS. 8E and 8F demonstrate significantly decreased cytotoxicity of primary CD147-CAR-NK cells using knockout-CD147 FFLuc-GFP-SK-Hep1 cell line and HepG2 cell line by the 4-h standard $^{51}$Cr release assays. Data represent the mean±SEM from three independent experiments. FIG. 8G shows that anti-NKG2D antibody blocked primary CD147-CAR-NK naturally killing to FFLuc-GFP-SK-Hep1. Primary CD147-CAR-NK cells in different ratios were co-cultured with FFLuc-GFP-SK-Hep1, knockout-CD147 FFLuc-GFP-SK-Hep1 cell line, or knockout-CD147 FFLuc-GFP-SK-Hep1 cell lines with 5 μg anti-NKG2D for 4 hours. FFLuc reporter assays were used. Data represent the mean±SEM from three independent experiments. FIG. 8H shows cytotoxicity of CD147-CAR-NK-92MI to the SK-Hep1 was measured by a standard 4-hr $^{51}$Cr release assay. Effector cells (CD147-CAR-NK-92MI and NK-92MI) were co-cultured with target cells at $1 \times 10^4$ per well FFLuc-GFP-SK-Hep1. Four hours later, the supernatants were collected and the released $^{51}$Cr was measured with a gamma counter. FIGS. 8I and 8J are FFLuc reporter system assay for specific killing of FFLuc-GFP-SK-Hep1 and FFLuc-GFP-HepG2 cell lines by CD147-CAR-NK-92MI. Effector cells (CD147-CAR-NK-92MI and NK-92MI) were co-cultured with $1 \times 10^4$ FFLuc-GFP-SK-Hep1 (FIG. 8I) or FFLuc-GFP-HepG2 (FIG. 8J) target cells per well in a 96-well optical-bottom microplate for 6 hours. Luminescent signals were measured by microplate reader after incubated with D-Luciferin for 5 minutes to calculate cytotoxicity of NK cells. The control groups used were wild type NK-92MI incubated with CD147-positive FFLuc-GFP-SK-Hep1 or CD147-positive FFLuc-GFP-HepG2. FIGS. 8K and 8L demonstrate decreased cytotoxicity of CD147-CAR-NK-92MI cells using knockout-CD147 FFLuc-GFP-SK-Hep1 (FIG. 8K) and knockout-CD147-FFLuc-GFP-HepG2 (FIG. 8L) cell lines by FFLuc reporter system assay. Effector cells (CD147-CAR-NK-92MI and NK-92MI) were co-cultured with $1 \times 10^4$ wild-type or CD147 knockout target cells per well in a 96-well optical-bottom microplate for 6 hours. Luminescent signals were measured by microplate reader after incubated with D-Luciferin for 5 minutes to calculate cytotoxicity of NK cells. FIGS. 8M and 8N are graphs showing that anti-CD147 (clone, HIM6) inhibited the CD147-CAR-NK-92MI specific lysis effect against and FFLuc-GFP-SK-Hep1 (FIG. 8M) and FFLuc-GFP-HepG2 (FIG. 8N). Effector cells (CD147-CAR-NK-92MI and NK-92MI) were co-cultured with $1 \times 10^4$ FFLuc-GFP-SK-Hep1 or FFLuc-GFP-HepG2 target cells per well in a 96-well optical-bottom microplate for 6 hours. Luminescent signals were measured by microplate reader after incubated with D-Luciferin for 5 minutes to calculate cytotoxicity of NK cells. Data represent the mean±SEM from three independent experiments. *p<0.05, p<0.01, and *p<0.001.

FIG. 9A shows staining of surface CD147 molecules on wild-type (wt) SK-Hep1 and CD147$^{-/-}$-SK-Hep1 cell lines (top), as well as wild-type (wt) HepG2 and CD147$^{-/-}$-HepG2 cell lines (bottom). FIG. 9B shows a Western blot analysis of CD147 molecules on wild-type (wt) SK-Hep1 and CD147$^{-/-}$-SK-Hep1 cell lines, as well as on wild-type (wt) HepG2 and CD147$^{-/-}$-HepG2 cell lines. GAPDH was used as a loading control (bottom).

FIGS. 10A-10C show CD147-CAR-NK-T cells specifically kill CD147-positive tumor cells. Cytotoxicity of CD147-CAR-T cells was measured by a FFLuc report system assay. CD147-positive FFLuc-EGFP-Hep-G2 (FIG. 10A) and CD147-positive FFLuc-EGFP-SK-Hep1 (FIG. 10B) were used as the CD147-CAR-T susceptible target cells. Kappa-CAR T cells were used as control groups for each experiment. FIG. 10C shows significantly decreased cytotoxicity of CD147-CAR-T cells using knockout-CD147 FFLuc-GFP-SK-Hep1 cell line by FFLuc report system assay. Briefly effector cells (CD147-CAR-T cells) were co-cultured with target cells FFLuc-EGFP-SK-Hep1 or CD147 knockout FFLuc-EGFP-SK-Hep1 ($1 \times 10^4$) in a 96-well optical-bottom microplate for 6 hours. Cytotoxicity of CD147-CAR-T cells was measured by the luminescence signal read by a microplate reader. Data represent the mean±SEM from three independent experiments. *p<0.05, p<0.01, and *p<0.001.

FIG. 11A is a diagram of experimental design of HCC xenograft model. Briefly, NSG mice were subcutaneous injected with $4 \times 10^6$ SK-Hep1 cells premixed with equal volume Matrigel (Day 0). Mice were monitored tumor burden (achieved nearly 50 mm$^2$) and randomly grouped on day 4. At day 5 (D5), mice were injected (i.v.) with one dose of $1 \times 10^7$ effector CD147-CAR-T (Group #1) cells with $2 \times 10^4$ IU IL-2. The control groups were injected with vehicle (PBS) control only (Group #2). At day 7, 9, and 16, identical treatments in each group were administrated. FIG. 11B shows quantification of tumor burden of SK-Hep1 xenografts treated with CD147-CAR-T and PBS (vehicle control group), respectively. All results are mean±SEM. The difference for each group was analyzed by two-way ANOVA analysis. FIG. 11C is quantitative body weight of each group was assessed at the indicated time points. FIG. 11D shows Kaplan-Meier survival curves of tumor-bearing mice after treatment with CD147-CAR-T cells and PBS (vehicle control group). The p-value was analyzed by log-rank (Mantel-Cox) Test.

FIGS. 12A-12D show the antitumor efficacy of CD147-CAR-NK-92-MI cells against HCC in a mouse xenograft model. FIG. 12A is a diagram of experimental design for anti-tumor efficacy of primary CD147-CAR-NK in HCC xenograft model. After tumor implantation for 5 days (day 5), the mice were injected (i.v.) with one dose $1 \times 10^7$ effector primary CD147-CAR-NK cells with $2 \times 10^4$ IU IL-2. The control groups were injected with the same number of non-transduced primary NK cells with $2 \times 10^4$ IU IL-2 (Group #2) or PBS only (Group #3). At day 5, 7, 9, 16, and 18, identical treatments in each group were administrated, as indicated. FIG. 12B shows quantitative tumor burden of HCC xenograft mice treated with primary CD147-CAR-NK, non-transduced primary NK, and PBS (vehicle control group), respectively. All results are mean±SEM. The difference for each group was analyzed by two-way ANOVA analysis. FIG. 12C shows quantitative body weights of each group were assessed at the indicated time points. FIG. 12D is Kaplan-Meier survival curves of tumor-bearing mice after treatment with primary CD147-CAR-NK, parental primary NK groups, and PBS (vehicle control group). P-value analysis by log-rank (Mantel-Cox) Test. The difference for each group was analyzed by two-way ANOVA analysis. The *p<0.05, p<0.01, and *p<0.001 are indicated as in comparison of the CD147-CAR-modified cells treated groups with the control groups.

FIG. 13 shows comparable anti-HCC tumor activity between irradiated CD147-CAR-NK-92MI and non-irradiated CD147-CAR-NK-92MI cells in killing HCC cell lines in vitro. Cytotoxicity of irradiated and non-irradiated CD147-CAR-NK-92MI was measured by the standard 4-hr $^{51}$Cr release assay. CD147-positive wild type-HepG2 tumor cell (experimental group, left panel) or CD147-knockout (CD147KO, right panel) HepG2 tumor cell lines were used as the CD147-CAR-NK-92MI susceptible target cells. Irradiated and non-irradiated wild type NK-92MI cells were used as effector cell control groups. Data are representative of three independent experiments. All data are presented as the mean±SEM.

FIG. 14A is a diagram of experimental design of HCC xenograft model. NSG mice were injected (s.c.) with $2\times10^6$ SK-Hep1 cells premixed with equal volume Matrigel (Day 0). One day before the treatment (at day 4), tumor burden was determined (achieved nearly 50 mm$^2$) and mice randomly grouped. At day 5 (D5) mice were injected (i.v.) with one dose of $1\times10^7$ effector non-irradiated CD147-CAR-NK-92MI (Group #1) cells with $2\times10^4$ IU IL-2. The control groups were injected with the same number of irradiated CD147-CAR-NK-92MI with $2\times10^4$ IU IL-2 (Group #2) in PBS or vehicle control only (Group #3). At days 7, 9, 16, and 18, identical treatments in each group were administrated. FIG. 14B shows quantification of tumor burden of SK-Hep1 xenografts treated with CD147-CAR-NK-92MI and PBS (vehicle control group), respectively. All results are mean±SEM. The difference for each group was analyzed by two-way ANOVA analysis. FIG. 14C is a graph of quantitative body weight of each group was assessed at the indicated time points. FIG. 14D shows Kaplan-Meier survival curves of tumor-bearing mice after treatment with CD147-CAR-NK-92MI cells and PBS (vehicle control group). The p-value was analyzed by log-rank (Mantel-Cox) Test. Data are representative of two independent experiments. All data are presented as the mean±SEM.

FIG. 15A is a diagram of experimental design of HCC xenograft model. Briefly, NSG mice were subcutaneous injected with $4\times10^6$ SK-Hep1 cells premixed with equal volume Matrigel (Day-7). At Day 0 (the day before day 1), tumor burden was determined (around 50 mm$^2$) and mice were randomly grouped. At day 1 (D1) mice were injected (i.v.) with one dose of $1\times10^7$ effector CD147-CAR-NK-92MI (Group #1) cells with $2\times104$ IU IL-2. The control groups were injected with the same number of NK-92MI with $2\times10^4$ IU IL-2 (Group #2) in PBS or vehicle control only (Group #3). At day 3 and 5, identical treatments in each group were administered. FIG. 15B shows quantification of tumor burden of SK-Hep1 xenografts treated with CD147-CAR-NK-92MI, parental NK-92MI cells (control group), and PBS (vehicle control group), respectively. All results are mean±SEM. The difference for each group was analyzed by two-way ANOVA analysis. The *p<0.05, p<0.01, and *p<0.001 are indicated as in comparison of the CD147-CAR-treated group with the NK-92MI-treated group. The +p<0.05, ++p<0.01, and +++p<0.001 are indicated in comparison of the CD147-CAR-treated group with the vehicle control-treated group. FIG. 15C shows quantitative body weight of each group was assessed at the indicated time points and FIG. 15D shows Kaplan-Meier survival curves of tumor-bearing mice after treatment with CD147-CAR-NK-92MI cells, parental NK-92MI group, and PBS (vehicle control group). The p-value was analyzed by log-rank (Mantel-Cox) Test.

FIG. 16A is a diagram of experimental design for anti-tumor efficacy of CD147-CAR-NK-92MI in a liver PDX model generated by The Jackson Laboratory. The patient-derived xenograft liver cancer mice were purchased from The Jackson Laboratory. After tumor implantation for 4 weeks (day 1), tumor burden was determined (around 50 mm$^2$) and mice were randomly grouped. Then indicated mice were injected (i.v.) with one dose of $5\times10^6$ effector CD147-CAR-NK-92MI cells with $2\times10^4$ IU IL-2. The control groups were injected with the same number of NK-92MI cells with $2\times10^4$ IU IL-2 (Group #2) in PBS or PBS only (Group #3). At day 6, 8, 11, 15, 18, 22, and 26, identical treatments in each group were administrated, as indicated. FIG. 16B is quantitative tumor burden of PDX mice treated with CD147-CAR-NK-92MI cells, parental NK-92MI cells (control group), and PBS (vehicle control group), respectively. All results are mean±SEM. The difference for each group was analyzed by two-way ANOVA analysis. The *p<0.05, p<0.01, and *p<0.001 are indicated as in comparison of the CD147-CAR-treated group with the NK-92MI-treated group. The +p<0.05, ++p<0.01, and +++p<0.001 are indicated in comparison of the CD147-CAR-treated group with the vehicle control-treated group. FIG. 16C shows quantitative body weights of each group were assessed at the indicated time points. FIG. 16D is Kaplan-Meier survival curves of tumor-bearing mice after treatment with CD147-CAR-NK-92MI cells, parental NK-92MI groups, and PBS (vehicle control group). P-value analysis by log-rank (Mantel-Cox) Test.

FIGS. 17A-17D show killing of CD147-positive HCC cells by CD147-CAR-T cells. FFLuc reporter system assay for specific killing of FFLuc-EGFP-HepG2 by CD147-CAR-T cells (FIG. 17A). The control group used the wild type kappa-CAR-T cells incubating with CD147-positive FFLuc-EGFP-HepG2. FIG. 17B shows decreased cytotoxicity of CD147-CAR-T cells using knockout-CD147 FFLuc-GFP-HepG1 by FFLuc report system assay. FIG. 17C shows cytotoxicity of CD147-CAR-T cells measured by a standard 4-hr $^{51}$Cr release assay. FIG. 17D shows significantly decreased cytotoxicity of CD147-CAR-T cells using knockout-CD147 FFLuc-GFP-HepG1 by a standard 4-hr $^{51}$Cr release assay.

FIG. 18A shows representative flow cytometric data illustrating CD107a degranulation on CD147-CAR-T cells after 10 hours with medium (control), SK—N—SH tumor cells. Cells were gated for CD56 positive subsets for quantifying surface CD107a expression. FIG. 18B shows quantitative data for percentage of surface CD107a expression on CD147-CAR-NK-92MI cells upon different stimulations, as indicated. Data are pooled from at least three or four experiments.

FIG. 20 is an alignment showing an optimized CD147 scFv nucleic acid sequence (SEQ ID NO: 1) compared to the original scFv sequence (SEQ ID NO: 3), and a consensus sequence (SEQ ID NO: 13).

FIG. 21A is representative H&E (top) and IHC (bottom) staining of liver samples from different stages of HCC patients. FIG. 21C is a diagram of experimental design of HCC sample acquisition from different areas of liver cancer tissues. Briefly, three regions of interest (tumor zone, adjacent zone, and non-tumor zone) were obtained. Primary NK cells were isolated from these zones (illustrated in FIG. 21B). FIG. 21D is flow cytometry analysis of CD147-CAR positive primary NK cells from different zones of liver tissues. FIG. 21E shows cytotoxicity of primary CD147-CAR-NK cells measured by 4-h standard $^{51}Cr$ release assays.

FIG. 23A is a schematic design of GPC3-Gal4VP64-synNotch receptor in SFG retroviral vector and CD147-CAR based on the pHR lentiviral vector. The SFG retroviral vector contains eGFP, which can be used as a marker for selecting GPC3-Gal4VP64-synNotch positive cells. The pHR construct included the CD147-specific single chain antibody fragment (clone, 5F6), a human IgG1 CH2CH3 hinge region and CD28 transmembrane region, followed by the intracellular domains of co-stimulatory CD28, 4-1BB, and the intracellular domain of CD3ζ. The pHR lentiviral vector contains mCherry, which can be used as a marker for selecting CD147-CAR positive cells. FIG. 23B is a schematic design of 'logic-gated' GPC3-synNotch and CD147-CAR showing induced cytotoxicity when both antigens are co-expressed, but not when they are separately expressed on bystander or healthy cells. FIGS. 23C and 23D are schematic experimental design of GPC3-synNotch-GFP and CD147-CAR-mCherry vectors co-transduced T cells (FIG. 23C) and representative flow cytometric analysis of GPC3-synNotch-GFP and CD147-CAR-mCherry expression (FIG. 23D). FIG. 23E is a schematic experimental design of GPC3-synNotch-GFP and CD147-CAR-mCherry vectors co-transduced into T cells, priming by GPC3$^{high}$CD147$^{low}$ HepG2 cell line, and followed by CD147-CAR expression analysis among different subsets of transduced T cells, including mCherry positive only, GFP positive only, GFP and mCherry double positive, and GFP and mCherry double negative subsets. FIG. 23F shows representative flow cytometric analysis of CD147-CAR expression on the surface of different subsets of transduced T cells. Both mean fluorescence intensity (MFI) and percentage of CD147-CAR are displayed in each representative flow cytometric chart. FIG. 23G is a representative flow cytometric analysis of CD147 and GPC3 expression on HepG2 tumor cell lines. FIG. 23H shows quantitative analysis of surface CD107a expression on different subsets of transduced T cells after 'primed and triggered' protocol by different HepG2 tumor cell lines for 2 hours. Data are representative of two independent experiments.

FIGS. 25A-25H shows SynNotch CD147-inducible GPC3-CAR T cells selectively target GPC3+CD147+ HepG2 cells, but not GPC3+CD147− or GPC3-CD147+ HepG2 cells. FIG. 25A is a schematic design of Myc-CD147-Gal4VP64-SynNotch receptor in the SFG retroviral vector and GPC3-CAR based on the pHR lentiviral vector. The SFG retroviral vector contains a Myc-tag, which can be used as a marker for selecting CD147-Gal4VP64-SynNotch positive cells. The pHR construct consisted of the GPC3-specific single chain antibody fragment (scFv, clone 5F6, mIgG1), a human IgG1 CH2CH3 hinge region and CD28 transmembrane region, followed by the intracellular domains of co-stimulatory CD28, 4-1BB, and the intracellular domain of CD32. The pHR lentiviral vector contains mCherry, which can be used as a marker for selecting cells with GPC3-CAR positive cells. FIG. 25B is a schematic design of 'Logic-gated' CD147-SynNotch and GPC3-CAR showing induced cytotoxicity when both antigens are co-expressed, but not activated when they are separately expressed on bystander or healthy cells. FIGS. 25C and 25D are schematic experimental design of Myc-CD147-Syn-Notch and GPC3-CAR-mCherry vectors co-transduced T cells (FIG. 25C) and Representative flow cytometric analysis of Myc-CD147-SynNotch and GPC3-CAR-mCherry expression (FIG. 25D). FIG. 25E is a schematic experimental design of Myc-CD147-SynNotch and GPC3-CAR-mCherry vectors co-transduced in T cells, priming by GPC3$^{high}$CD147$^{low}$ HepG2 cell line, and followed by GPC3-CAR expression analysis among different subsets of transduced T cells, including mCherry positive only, GFP positive only, GFP and mCherry double positive, and GFP and mCherry double negative subsets. FIG. 25F is a representative flow cytometric analysis of GPC3-CAR expression on the surface of different subsets of transduced T cells. Both mean fluorescence intensity (MFI) and percentage of GPC3-CAR are displayed in each representative flow cytometric chart. FIG. 25G is a representative flow cytometric analysis of surface CD107a expression on different subsets of transduced T cells after 'primed and triggered' protocol by different HepG2 tumor cell lines. FIG. 25H shows quantitative analysis of surface CD107a expression on different subsets of transduced T cells after 'primed and triggered' protocol by different HepG2 tumor cell lines. Fold-change of CD107a MFI was calculated as follows: [(MFIsample−MFIprimed only)/MFIprimed only]. Data are representative of two independent experiments. All data are presented as the mean±SEM. *p<0.05, p<0.01, and *p<0.001.

FIGS. 26A-26D show that SynNotch GPC3-inducible CD147-CAR T cells selectively kill GPC3$^{high}$CD147$^{high}$ HepG2 cells but not CD147$^{knockout}$GPC3$^{high}$ HepG2 cells. FIGS. 26A and 26B are representative flow cytometric analysis of CD3, CD56, GPC3-synNotch-GFP, and CD147-

US 12,624,102 B2

13

Figure 1A:
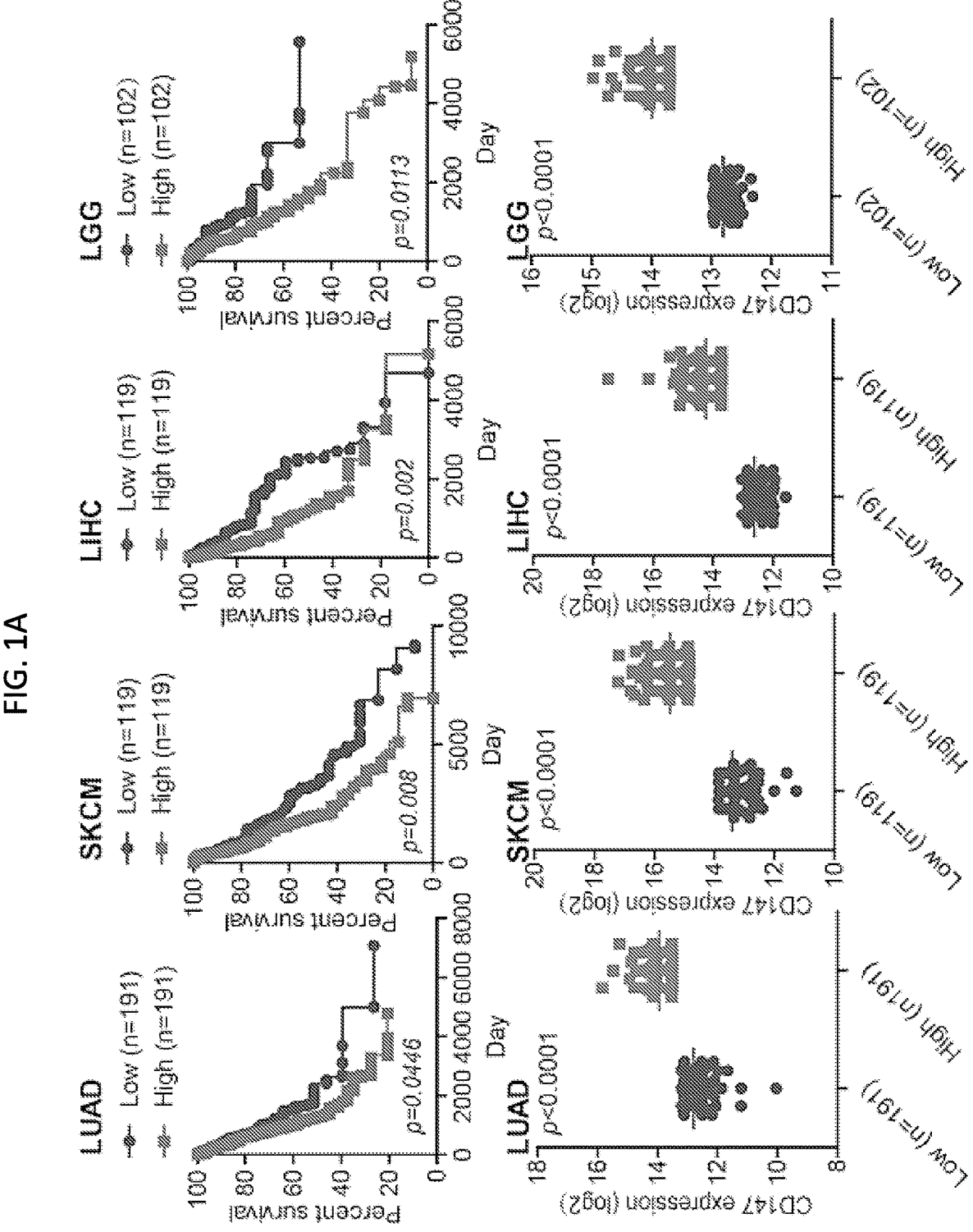
FIGS. 1A-1E show CD147 overexpression in hepatocellular carcinoma cells.

CAR-mCherry expression. Primary PBMCs were transduced with CD147-CAR-mCherry lentivirus. These mCherry positive T cells were sorted using flow cytometry, followed by a secondary transduction with GPC3-synNotch-GFP retrovirus. Representative flow cytometric analysis of CD3 and CD56 (FIG. 26A) and GPC3-synNotch-GFP and CD147-CAR-mCherry expression (FIG. 26B) are displayed, respectively. FIG. 26C is a graph of cytotoxicity of primary GPC3-synNotch-GFP-CD147-CAR-mCherry T cells against HepG2-CD147$^{high}$-GPC3$^{high}$ and HepG2-CD147$^{knockout}$-GPC3$^{high}$ measured by 7-hour FFluc reporter assays. FIG. 26D is a graph showing cytotoxicity of primary GPC3-synNotch-GFP-CD147-CAR-mCherry T cells against HepG2-CD147$^{high}$-GPC3$^{high}$ and HepG2-CD147$^{knockout}$-GPC3$^{high}$ measured by 7-hour Cr-51 release assays. Data are representative of two independent experiments.

SEQUENCE LISTING

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is a nucleic acid sequence encoding a modified CD147 scFv. Nucleotides 349-409 are a linker sequence.

SEQ ID NO: 2 is the amino acid sequence of the modified CD147 scFv.

SEQ ID NO: 3 is the nucleic acid sequence encoding the starting CD147 scFv.

SEQ ID NO: 4 is the nucleic acid sequence encoding a CD147-CAR. Signal peptide: nucleotides 1-57; VH domain: nucleotides 58-411; Linker sequence: nucleotides 412-468; VL domain: nucleotides 469-792; CD28 TM domain-41BB intracellular domain-CD3ζ domain: nucleotides 793-2202.

SEQ ID NO: 5 is the amino acid sequence of the CD147-CAR. Signal peptide: amino acids 1-19; VH domain: amino acids 20-137; Linker sequence: amino acids 138-156; VL domain: amino acids 157-264; CD28 TM domain-41BB intracellular domain-CD3ζ domain: amino acids 269-734.

SEQ ID NO: 6 is the nucleic acid sequence encoding CD14-CAR with inducible caspase 9. The iCaspase9 sequence is nucleotides 355-1200.

SEQ ID NO: 7 is the amino acid sequence of CD147-iCaspase 9-CAR. Amino acids 119-400 are iCaspase 9.

SEQ ID NO: 8 is the amino acid sequence of anti-CD147 VH CDR domains.

SEQ ID NO: 9 is the amino acid sequence of anti-CD147 VL CDR domains.

SEQ ID NOs: 10 and 11 are guide RNAs targeting CD147 used to generate CD147 knock out cell lines.

SEQ ID NO: 12 is an exemplary IL-15 receptor intracellular domain.

SEQ ID NO: 13 is a consensus nucleic acid sequence of an optimized CD147 scFv nucleic acid sequence (SEQ ID NO: 1) compared to the original scFv sequence (SEQ ID NO: 3).

SEQ ID NO: 14 is a nucleic acid sequence of a Gal4UAS CD147-CAR construct.

SEQ ID NO: 15 is the nucleic acid sequence of a pHR_Gal4UAS-CD147-CAR-pGK_mCherry vector.

SEQ ID NO: 16 is the nucleic acid sequence of a GPC3-CAR.

SEQ ID NO: 17 is a nucleic acid encoding a GAL4-VP64 activator.

SEQ ID NOs: 18-35 are the nucleic acid sequences of primers used for plasmid construction.

DETAILED DESCRIPTION

Disclosed herein are immune cells (including T cells and NK cells) expressing a novel CD147-targeting CAR. The biological properties of the CD147 antigen allow CD147-CAR-NK cells and CD147-CAR-T cells to produce potent antitumor activity against hepatocellular carcinoma in vitro and in vivo. In addition, CD147-CAR-NK cells are also capable of killing human neuroblastoma cells in vitro.

Since CD147 is also expressed on several organs with varying expression levels, CD147-CAR modified immune cells may potentially exhibit an "on-target, off-tumor" toxicity. Disclosed herein are constructs and methods for addressing this potential toxicity, including "suicide genes" (such as an inducible caspase 9) and combination treatments, such as CAR-expressing cells that are only activated upon binding of two antigens, such as CD147 and GPC3.

I. Terms

Unless otherwise noted, technical terms are used according to conventional usage. Definitions of common terms in molecular biology may be found in *Lewin's Genes* X, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3$^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank Accession numbers. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy (V$_H$) region and the variable light (V$_L$) region, respectively. Together, the V$_H$ region and the V$_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A single-chain antibody (scFv) is a genetically engineered molecule containing the V$_H$ and V$_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the V$_H$-domain and the V$_L$-domain in a scFv, is typically not decisive for scFvs. Thus, scFvs with both possible arrangements (V$_H$-domain-linker domain-V$_L$-domain; V$_L$-domain-linker domain-V$_H$-domain) may be used. In a dsFv the V$_H$ and V$_L$ have been mutated to introduce a disulfide bond to stabilize the association of the chains. Diabodies also are included, which are bivalent, bispecific antibodies in which V$_H$ and V$_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, IL); Kuby, J., *Immunology*, 3$^{rd}$ Ed., W.H. Freeman & Co., New York, 1997.

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrated to other parts of the body, for example via the bloodstream or lymph system.

CD147: Also known as basigin (BSG), extracellular matrix metalloproteinase inhibitor (EMMPRIN or EMPRIN). A transmembrane glycoprotein with multiple functions in normal cell function and disease (Hahn et al., *J. Leukocyte Biol.* 98:33-48, 2015). CD147 is important in immune cells for T cell activation and proliferation, as well as cell migration, adhesion, and invasion (Hahn et al., *J. Leukocyte Biol.* 98:33-48, 2015). CD147 is expressed on different cell types (e.g., hematopoietic, epithelial, and endothelial cells) at varying levels (Liao et al., *Mol. Cell Biol.* 31:2591-2604, 2011) and may be significantly upregulated in disease states, such as in HCC.

CD147 sequences are publicly available. For example, GenBank Accession Nos. NM_198590, NM_198591, NM_001728, NM_198589, and NM_001322243 disclose human CD147 nucleic acid sequences, and GenBank Accession Nos. NP_940992, NP_940993, NP_001719, NP_940991, and NP_001309172 disclose human CD147 amino acid sequences. Similarly, NM_009768 and NM_001077184 disclose mouse CD147 nucleic acid sequences and GenBank Accession Nos. NP_033898 and NP_001070652 disclose mouse CD147 amino acid sequences. All of these sequences are incorporated by reference as present in GenBank on Mar. 15, 2019.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs include an antigen-binding portion, a transmembrane domain, and an intracellular domain. The intracellular domain typically includes a signaling chain having an immunoreceptor tyrosine-based activation motif (ITAM), such as CD3ζ or FcεRIγ. In some instances, the intracellular domain also includes the intracellular portion of at least one additional co-stimulatory domain, such as CD28, 4-1BB (CD137), ICOS, OX40 (CD134), CD27 and/or DAP10.

Complementarity determining region (CDR): A region of hypervariable amino acid sequence that defines the binding affinity and specificity of an antibody. The light and heavy chains of a mammalian immunoglobulin each have three CDRs, designated VL-CDR1, VL-CDR2, VL-CDR3 and VH-CDR1, VH-CDR2, VH-CDR3, respectively.

Glypican-3 (GPC3): A cell surface heparan sulfate proteoglycan that binds to and inhibits CD26 activity. GPC3 can induce apoptosis in some cell types. GPC3 is expressed by some tumors, including hepatocellular carcinoma, melanoma, ovarian clear-cell carcinoma, yolk sac tumors, neuroblastoma, hepatoblastoma, and Wilms tumor.

GPC3 sequences are publicly available. For example, GenBank Accession Nos. NM_001164619, NM_001164618, NM_004484, and NM_001164617 disclose exemplary human GPC3 nucleic acid sequences, and GenBank Accession Nos. NP_001158091, NP_001158090, NP_004475, and NP_001158089 disclose exemplary human GPC3 amino acid sequences. Similarly, GenBank Accession No. NM_016697 discloses an exemplary mouse GPC3 nucleic acid sequence and GenBank Accession No. NP_057906 discloses an exemplary mouse GPC3 amino acid sequence. Each of these sequences are incorporated by reference as present in GenBank on Feb. 27, 2020.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Liver cancer: Hepatocellular carcinoma (HCC) is the most common type of primary malignancy of the liver, which often occurs in patients with viral hepatitis (e.g., hepatitis B or hepatitis C), toxin exposure, or hepatic cirrhosis (sometimes caused by alcoholism). Other types of liver cancer include intrahepatic cholangiocarcinoma (iCCA), fibrolamellar carcinoma, and hepatoblastoma.

Natural Killer (NK) cells: Cells of the immune system that kill target cells in the absence of a specific antigenic stimulus and without restriction according to MHC class. Target cells can be tumor cells or cells harboring viruses. NK cells are characterized by the presence of CD56 and the absence of CD3 surface markers. NK cells typically comprise approximately 10 to 15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the CTL response by down-regulating MHC class I presentation. In addition to being involved in direct cytotoxic killing, NK cells also serve a role in cytokine production, which can be important to control cancer and infection.

In some examples, a "modified NK cell" is a NK cell transduced or transfected with a heterologous nucleic acid (such as one or more of the nucleic acids or vectors disclosed herein) or expressing one or more heterologous proteins. The terms "modified NK cell" and "transduced NK cell" are used interchangeably in some examples herein.

Purified: The term purified does not require absolute purity; rather, it is intended as a relative term. Thus, for example, a purified protein or nucleic acid preparation is one in which the protein or nucleic acid is more enriched than the protein or nucleic acid is in its natural environment (e.g., within a cell). In one embodiment, a preparation is purified such that the protein or nucleic acid represents at least 50% of the total protein or nucleic acid content of the preparation. Substantial purification denotes purification from other proteins or cellular components. A substantially purified protein or nucleic acid is at least 60%, 70%, 80%, 90%, 95% or 98% pure. Thus, in one specific, non-limiting example, a substantially purified protein or nucleic acid is 90% free of other components.

Recombinant: A nucleic acid or protein that has a sequence that is not naturally occurring or has a sequence that is made by an artificial combination of two otherwise separated segments of sequence (e.g., a "chimeric" sequence). This artificial combination can be accomplished by chemical synthesis or by the artificial manipulation of isolated segments of nucleic acids, for example, by genetic engineering techniques.

Subject: A living multi-cellular vertebrate organism, a category that includes both human and veterinary subjects, including human and non-human mammals.

T cell: A white blood cell (lymphocyte) that is an important mediator of the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8$^+$ T cell is a cytotoxic T lymphocyte (CTL). In another embodiment, a CD8$^+$ cell is a suppressor T cell.

Activated T cells can be detected by an increase in cell proliferation and/or expression of or secretion of one or more cytokines (such as IL-2, IL-4, IL-6, IFN$\gamma$, or TNF$\alpha$). Activation of CD8+ T cells can also be detected by an increase in cytolytic activity in response to an antigen.

In some examples, a "modified T cell" is a T cell transduced or transfected with a heterologous nucleic acid (such as one or more of the nucleic acids or vectors disclosed herein) or expressing one or more heterologous proteins. The terms "modified T cell" and "transduced T cell" are used interchangeably in some examples herein.

Transduced or Transformed: A transformed cell is a cell into which a nucleic acid molecule has been introduced by molecular biology techniques. As used herein, the terms transduction and transformation encompass all techniques by which a nucleic acid molecule might be introduced into such a cell, including transfection with viral vectors, the use of plasmid vectors, and introduction of DNA by electroporation, lipofection, and particle gun acceleration.

Treating or ameliorating a disease: "Treating" refers to a therapeutic intervention that decreases or inhibits a sign or symptom of a disease or pathological condition after it has begun to develop, such as a reduction in tumor size or tumor burden. "Ameliorating" refers to the reduction in the number or severity of signs or symptoms of a disease, such as cancer.

Vector: A nucleic acid molecule that can be introduced into a host cell (for example, by transfection or transduction), thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function.

II. Overview of Several Embodiments

Disclosed herein are CD147-specific binding agents, including a modified CD147 scFv. Also disclosed are chimeric antigen receptors (CARs) that encode the CD147-specific binding agent fused to a hinge region, a transmembrane domain and an intracellular domain including a co-stimulatory domain and an intracellular signaling domain. In some examples, the co-stimulatory domain is from CD28 and/or 4-1BB and the signaling domain is from CD3$\zeta$. Also provided are nucleic acids encoding the CD147-specific binding agents and the CD147-CARs, and vectors including the nucleic acids.

Also provided herein are modified immune cells (such as T cells, NK cells, NKT cells, DNT cells, neutrophils, or macrophages) that express the CD147-CARs. In some embodiments, the modified immune cells express one or more additional CARs, such as a CAR targeting hepatitis virus (for example, hepatitis B or hepatitis C). In other embodiments, the modified immune cells express an inducible CD147-CAR and a construct that induces expression of the CD147-CAR, such as an anti-GPC3 SynNotch construct that drives expression of an inducer of the CD147-CAR. In further embodiments, the modified immune cells express an inducible GPC3-CAR and a construct that induces expression of the GPC3-CAR, such as an anti-CD147 SynNotch construct that drives expression of an inducer of the GPC3-CAR. In particular examples, the CD147-CAR and/or the anti-CD147 SynNotch construct include the modified CD147 scFv disclosed herein.

Also provided are methods of treating a cancer that expresses CD147 in a subject. In some embodiments, the method includes administering to the subject an effective amount of a modified immune cell (such as a T cell, NK cell, NKT cell, DNT cell, neutrophil, or macrophage) comprising a nucleic acid encoding a CD147-CAR. In other embodiments, the method includes administering to the subject an effective amount of a modified immune cell (such as a T cell, vided in Table 1. In some examples, the scFv specifically binds CD147 and includes an amino acid sequence comprising the variable heavy chain (VH) domain complementarity determining region 1 (CDR1), CDR2 and CDR3 amino acid sequences of SEQ ID NO: 8 and the variable light chain (VL) domain CDR1, CDR2 and CDR3 amino acid sequences of SEQ ID NO: 9. In some embodiments, the scFv includes the CDR amino acid sequences provided in Table 1 and has at least 90% sequence identity (for example, at least 91%, at least 92%, at least 93%, at least 94%, at least 95%, at least 96%, at least 97%, at least 98% or at least 99% sequence identity) to the amino acid sequence of SEQ ID NO: 1. In other embodiments, the scFv includes or consists of the amino acid sequence of SEQ ID NO: 1.

TABLE 1

| CDR | Nucleic Acid Sequence (SEQ ID NO: 1) | Amino Acid Sequence (SEQ ID NO: 2) |
|---|---|---|
| VH CDR1 | GGCTTCACCTTCAGCAACTAC (nt 76-96) (SEQ ID NO: 36) | GFTFSNY (aa 26-32) (SEQ ID NO: 42) |
| VH CDR2 | AGACTGAAGTCCTACAACTACGCC (nt 154-177) (SEQ ID NO: 37) | RLKSYNYA (aa 52-59) (SEQ ID NO: 43) |
| VH CDR3 | GATGGCAGCGAC (nt 301-312) (SEQ ID NO: 38) | DGSD (aa 101-104) (SEQ ID NO: 44) |
| VL CDR1 | AAGGCCTCCCAGTCCGTGAGCAACGATGTGGCC (nt 478-510) (SEQ ID NO: 39) | KASQSVSNDVA (aa 155-165) (SEQ ID NO: 45) |
| VL CDR2 | TACGCCAGCAACAGGTACACA (nt 556-576) (SEQ ID NO: 40) | YASNRYT (aa 181-187) (SEQ ID NO: 46) |
| VL CDR3 | CAGCAGGACTACTCCAGCCCCTACACC (nt 673-699) (SEQ ID NO: 41) | QQDYSSPYT (aa 220-228) (SEQ ID NO: 47) |

Location of the CDRs in the CD147 scFv sequence (determined using Kabat numbering scheme)

NK cell, NKT cell, DNT cell, neutrophil, or macrophage) comprising a nucleic acid encoding an inducible CD147-CAR and a nucleic acid for an anti-GPC3 SynNotch that expresses an inducer of the CD147-CAR expression. In still other embodiments, the method includes administering to the subject an effective amount of a modified immune cell (such as a T cell, NK cell, NKT cell, DNT cell, neutrophil, or macrophage) comprising a nucleic acid encoding a GPC3-CAR and an anti-CD147 SynNotch construct that expresses an inducer of the GPC3-CAR expression. In some examples, the modified immune cells are autologous. In other examples, the immune cells are allogeneic. In some specific examples, the subject has hepatocellular carcinoma or neuroblastoma.

III. CD147 Specific Binding Agents

Figure 20:
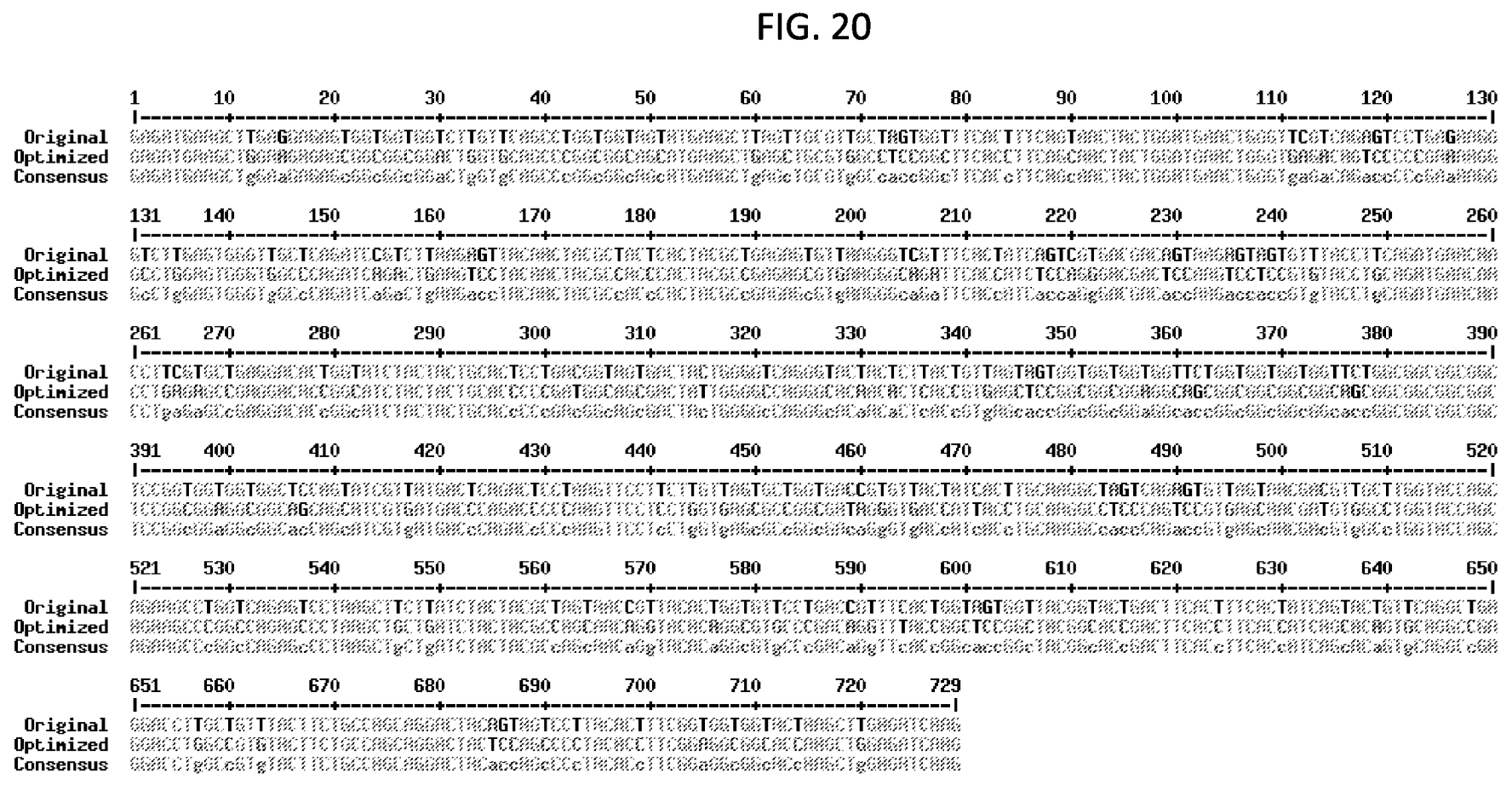

Disclosed herein is a CD147 binding agent, that in some examples is used as the targeting portion of a chimeric antigen receptor. In some embodiments, the CD147 binding agent is a CD147 scFv that is a modified fragment encoding the CD147-specific scFv from the 5F6 clone (U.S. Pat. No. 8,618,264). FIG. 20 shows an alignment of the starting CD147 scFv nucleic acid sequence (SEQ ID NO: 3) and the modified scFv nucleic acid sequence (SEQ ID NO: 1). In some examples, the modified CD147-specific scFv binds to high-expressing CD147 cells.

In some embodiments, the CD147-specific binding agent is a single domain antibody (such as an scFv) that specifically binds CD147 and includes the CDR sequences pro- In additional examples, the scFv is encoded by a nucleic acid including the CDR sequences provided in Table 1 and has at least 90% sequence identity (for example, at least 91%, at least 92%, at least 93%, at least 94%, at least 95%, at least 96%, at least 97%, at least 98% or at least 99% sequence identity) to the nucleotide sequence of SEQ ID NO: 2. In other embodiments, the scFv is encoded by a nucleic acid that includes or consists of the nucleotide sequence of SEQ ID NO: 2.

Also provided are vectors that include a nucleic acid encoding the CD147-specific binding agents described above. In some examples, the vector includes a nucleic acid with at least 90% sequence identity (for example, at least 91%, at least 92%, at least 93%, at least 94%, at least 95%, at least 96%, at least 97%, at least 98% at least 99%, or 100% identity) to SEQ ID NO: 1, for example, encoding an amino acid sequence with at least 90% sequence identity (for example, at least 91%, at least 92%, at least 93%, at least 94%, at least 95%, at least 96%, at least 97%, at least 98% at least 99%, or 100% identity) to SEQ ID NO: 2.

Figures 25A, 25B:
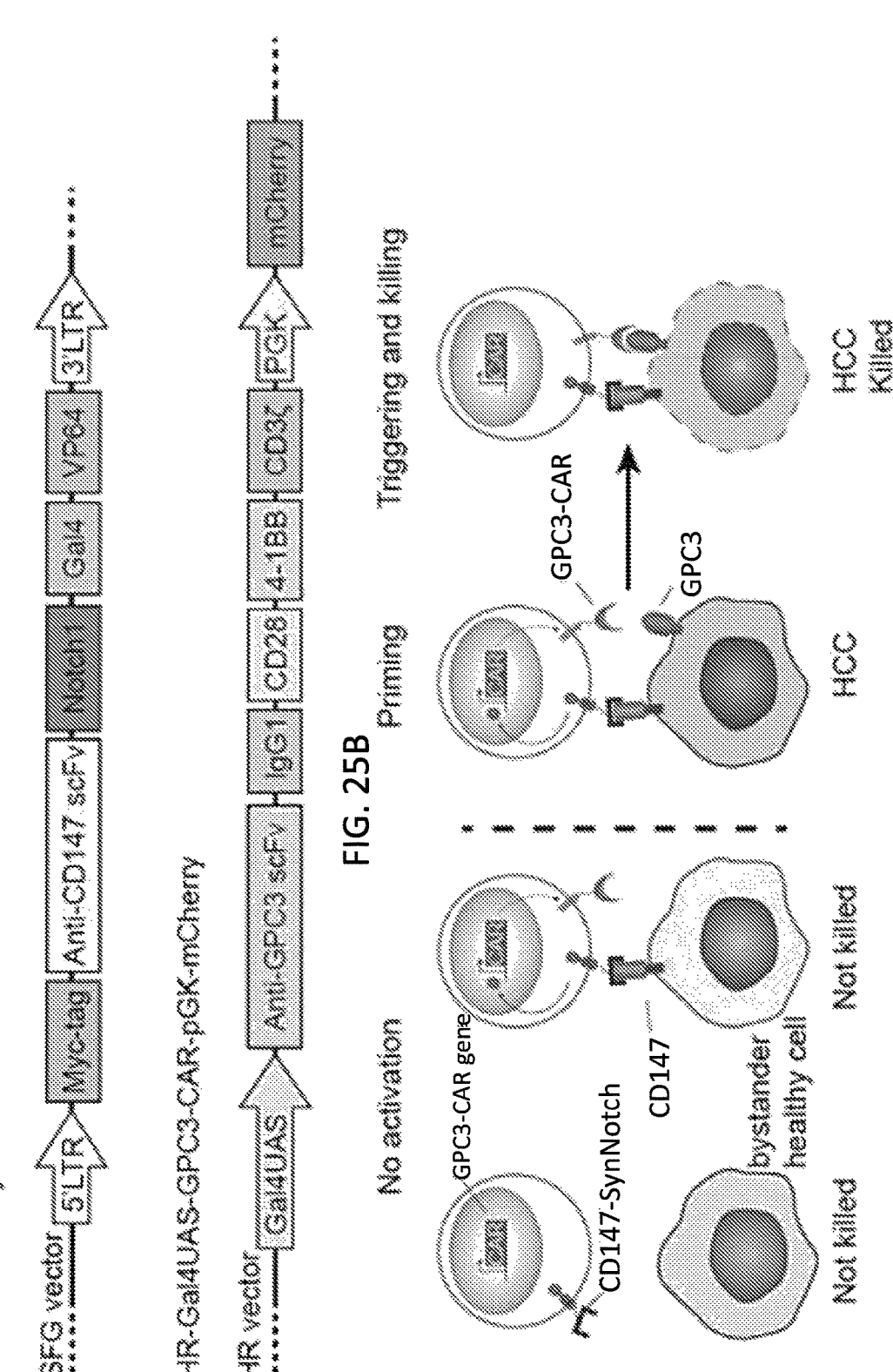
Figures 25C, 25D:
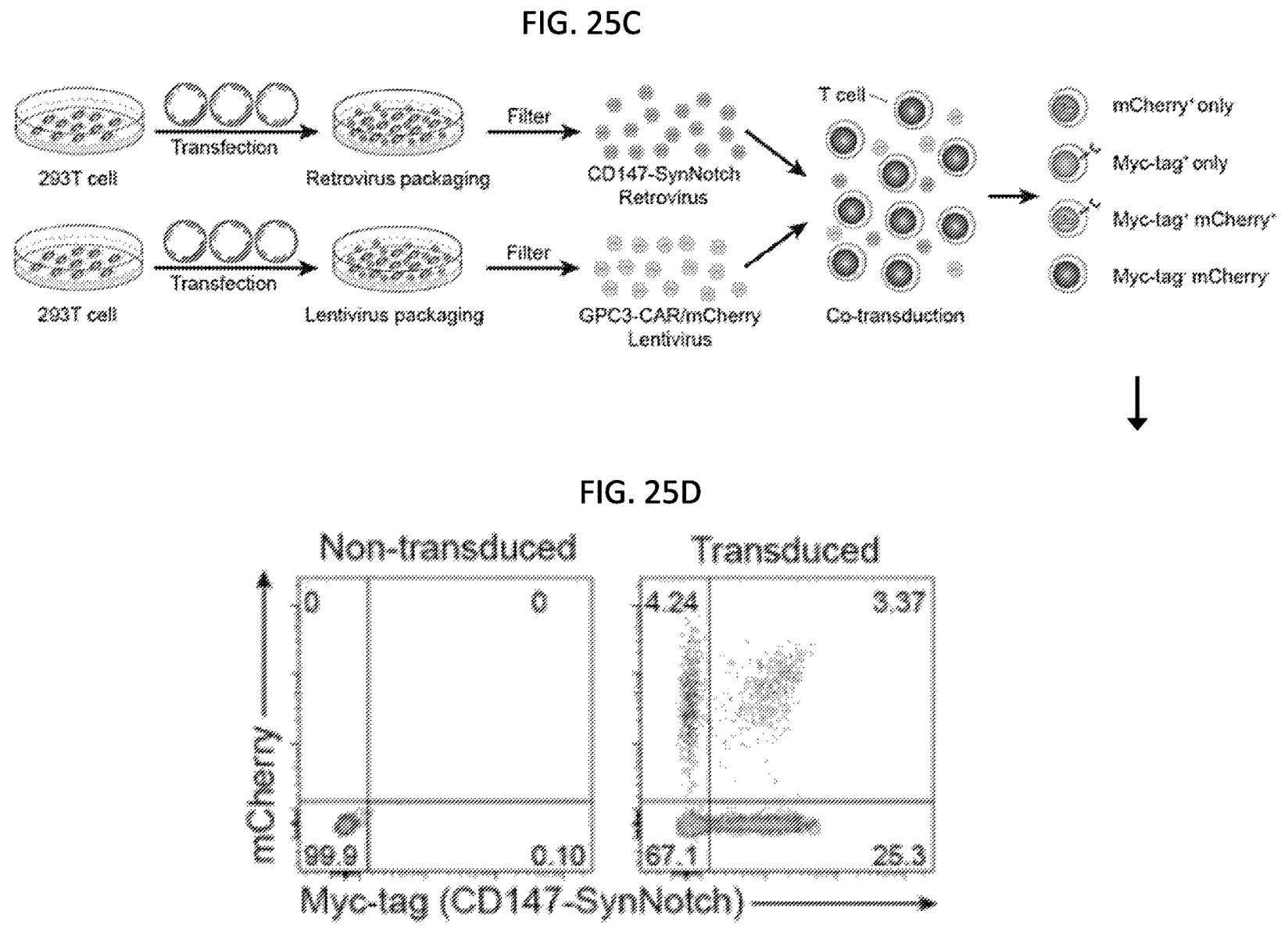

In further examples, provided herein are nucleic acids encoding an CD147-specific binding agent (such as a nucleic acid with at least 90% sequence identity (for example, at least 91%, at least 92%, at least 93%, at least 94%, at least 95%, at least 96%, at least 97%, at least 98% at least 99%, or 100% identity to SEQ ID NO: 1) that is operably linked to a nucleic acid encoding Gal4-VP64 (e.g., SEQ ID NO: 17). In some examples, the nucleic acid is part of a SynNotch construct. When CD147 binds to the protein encoded by this construct, Gal4-VP64 is activated, and can induce expression of a construct with a Gal4-responsive element (such as Gal4UAS). An exemplary vector encoding an anti-CD147 scFv SynNotch inducer construct is shown in FIG. 25A.

IV. CD147 Chimeric Antigen Receptors

Provided herein are CD147-CARs that include the CD147-specific binding agent described in Section III above. In some embodiments, the CAR includes an antigen binding domain including a CD147-specific scFv (such as SEQ ID NO: 2), a hinge domain, a transmembrane domain, and an intracellular domain including at least one co-stimulatory domain and an intracellular signaling domain.

In some embodiments, the antigen binding domain is a CD147-specific scFv, for example having an amino acid sequence with at least 90% sequence identity (for example, at least 91%, at least 92%, at least 93%, at least 94%, at least 95%, at least 96%, at least 97%, at least 98% at least 99% identity) to SEQ ID NO: 2 or including or consisting of the amino acid sequence of SEQ ID NO: 2.

In some embodiments, the hinge domain is an IgG hinge region. In one example, the hinge domain is an IgG1 hinge. Other hinge domains can be used, such as hinge regions from other immunoglobulins (for example, IgG4 or IgD) or a hinge region from CD8, CD28, or CD40.

In additional embodiments, the transmembrane domain is a CD28 transmembrane domain. In one example, the trans-membrane domain is from CD28. The transmembrane domain can also be from other T cell proteins, such as CD8, CD4, CD3ζ, CD40, OX40L, 41BBL, ICOS, ICOS-L, CD80, CD86, ICAM-1, LFA-1, ICAM-1, CD56, CTLA-4, PD-1, TIM-3, NKP30, NKP44, NKP40, NKP46, B7-H3, PD-L1, PD-2, and CD70.

In further embodiments, the intracellular domain includes one or more intracellular regions from a co-stimulatory molecule, or a portion thereof. Exemplary co-stimulatory molecules include CD28, 4-1BB, CD8, CD40, OX-40, ICOS, CD27, and DAP10, OX40-L, 4-1BBL, ICOS-L, CD80, CD86, ICAM-1, LFA-1, CD56, CTLA-4, PD-1, TIM-3, NKP30, NKP44, NKP40, NKP46, B7-H3, PD-L1, PD-2, and CD70. In particular examples, the co-stimulatory domain is from CD28 and/or 4-1BB. In one example, the co-stimulatory domain includes domains from both CD28 and 4-1BB. The intracellular domain also includes an intra-cellular signaling domain from CD3ζ. In other examples, the intracellular signaling domain is from DAP10, DAP12, PDK, or FcεRIγ. In one example, the intracellular signaling domain is from CD3ζ.

In some embodiments, the CD147-CAR also includes a signal sequence, which is located N-terminal to the scFv domain. In some examples, the signal sequence is a IgG signal sequence or a GM-CSF signal sequence. In one example, the signal sequence is amino acids 1-19 of SEQ ID NO: 5.

In particular embodiments, the CD147-CAR includes an amino acid sequence with at least 90% sequence identity (for example, at least 91%, at least 92%, at least 93%, at least 94%, at least 95%, at least 96%, at least 97%, at least 98% at least 99% identity) to SEQ ID NO: 5. In some examples, the CD147-CAR includes or consists of the amino acid sequence of SEQ ID NO: 5.

In additional embodiments, the CD147-CAR further includes an inducible gene that can be used to eliminate CD147-CAR expressing cells (e.g., a "suicide" gene). The inducible gene can be activated in the event of off target side effects (or on target/off tumor effects), such as cytokine release syndrome ("cytokine storm"). In some examples, expression of the suicide gene is inducible by a small molecule, such as tetracycline or doxycycline (a "TET ON" system) or rapamycin. See, e.g., Gargett et al., *Front. Pharmacol.* 5:235, 2014; Stavrou et al., *Mol. Ther.* 6:1266-1276, 2018. In other examples, the suicide gene is inducible by a Fas domain inducible system. In some examples, the inducible suicide domain is located N-terminal or C-termi-nal to the antigen binding domain of the CAR, while in other examples, the inducible suicide domain is located C-termi-nal to the CD3ζ domain of the CAR. The inducible suicide domain is separated from the CAR by a self-cleaving peptides (such as a P2A peptide or T2A peptide). In some embodiments, the inducible suicide domain includes Caspase 9, such as amino acids 119-400 of SEQ ID NO: 7. In some examples, a CD147-CAR including a tetracycline-inducible Caspase 9 includes an amino acid sequence with at least 90% sequence identity (for example, at least 91%, at least 92%, at least 93%, at least 94%, at least 95%, at least 96%, at least 97%, at least 98% at least 99% identity) to SEQ ID NO: 7. In other examples, the CD147-CAR including a tetracycline-inducible Caspase 9 includes or consists of the amino acid sequence of SEQ ID NO: 7.

In other embodiments, the CD147-CAR further includes a domain that increases survival or persistence of a modified immune cell expressing the CAR. In some examples, the domain is an intracellular domain from a cytokine receptor, for example, an intracellular domain from interleukin (IL) receptor 15 (e.g., SEQ ID NO: 12), IL-12 receptor, or IL-18 receptor. In other examples, the domain is an intracellular domain a growth factor receptor, such as an intracellular domain from CD40, NKG2D, NKP40, or NKP46. In some examples, the domain is located C-terminal to the CD32 domain of the CAR.

In some examples, the CD147-CAR further includes one or more additional antigen binding domains that specifically bind to an antigen that is co-expressed with CD147 on tumor cells. In some non-limiting examples, the CD147-CAR includes at least one additional antigen binding domain that specifically binds to a liver cancer antigen, such as one or more of glypican-3, alpha-fetoprotein, or mucin-1. Addi-tional tumor antigens can be selected based on the type of cancer being treated.

Also provided are nucleic acids encoding the CD147-CARs disclosed herein. In some embodiments, the nucleic acid encodes a CAR including a CD147-specific scFv, such as a nucleic acid sequence with at least 90% sequence identity (for example, at least 91%, at least 92%, at least 93%, at least 94%, at least 95%, at least 96%, at least 97%, at least 98% or at least 99% sequence identity) to SEQ ID NO: 1 or includes or consists of the nucleic acid sequence of SEQ ID NO: 1. In some examples, the CD147-specific CAR nucleic acid also encodes an IgG hinge domain, a CD28 transmembrane domain, CD28 and 4-1BB co-stimulatory domains, and a CD3ζ domain. In one example, the CD147-specific CAR is encoded by a nucleic acid sequence with at least 90% sequence identity (for example, at least 91%, at least 92%, at least 93%, at least 94%, at least 95%, at least 96%, at least 97%, at least 98% or at least 99% sequence identity) to SEQ ID NO: 4 or includes or consists of the nucleic acid sequence of SEQ ID NO: 4. In other examples, the CD147-specific CAR nucleic acid also encodes an inducible Caspase 9 domain, for example a nucleic acid sequence with at least 90% sequence identity (for example, at least 91%, at least 92%, at least 93%, at least 94%, at least 95%, at least 96%, at least 97%, at least 98% or at least 99% sequence identity) to SEQ ID NO: 6 or includes or consists of the nucleic acid sequence of SEQ ID NO: 6.

Also provided are functional variants of the CARs or the domains thereof described herein, which retain the biological activity of the CAR of which it is a variant or retains the biological activity of the particular domain. The functional variant can be at least about 80%, about 85%, about 90%, about 91%, about 92%, about 93%, about 94%, about 95%, about 96%), about 97%, about 98%, about 99% or more identical in amino acid sequence to the parent CAR or domain. Substitutions can be made, for example, in one or more of the extracellular targeting domain, hinge domain, transmembrane domain, and intracellular domains.

In some examples, the functional variant includes the amino acid sequence of the parent CAR or domain with at least one conservative amino acid substitution (such as up to 10 conservative amino acid substitutions, for example, 1, 2, 3, 4, 5, 6, 7, 8, 9, or 10 conservative substitutions). In other examples, the functional variant includes the amino acid sequence of the parent CAR or domain with at least one non-conservative amino acid substitution (such as up to 10 non-conservative amino acid substitutions, for example, 1, 2, 3, 4, 5, 6, 7, 8, 9, or 10 non-conservative substitutions). In this case, the non-conservative amino acid substitution does not interfere with or inhibit the biological activity of the functional variant. The non-conservative amino acid substitution may enhance the biological activity of the functional variant, such that the biological activity of the functional variant is increased as compared to the parent CAR or domain.

The CARs or domains thereof can in some examples, include one or more synthetic amino acids in place of one or more naturally-occurring amino acids. Such synthetic amino acids include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, -(2-amino-2-norbornane)-carboxylic acid, γ-diaminobutyric acid, α,β-diaminopropionic acid, homophenylalanine, and α-tert-butylglycine. The CARs may be glycosylated, amidated, carboxylated, phosphorylated, esterified, N-acylated, cyclized via, e.g., a disulfide bridge, or converted into an acid addition salt and/or optionally dimerized or polymerized, or conjugated.

In some embodiments, a nucleic acid molecule encoding a disclosed CAR is included in an expression vector (such as a viral vector) for expression in a host cell, such as a T cell or NK cell. In some examples, the expression vector includes a promoter operably linked to the nucleic acid molecule encoding the CAR. Additional expression control sequences, such as one or more enhancers, transcription and/or translation terminators, and initiation sequences can also be included in the expression vector. In some embodiments, a nucleic acid encoding a CD147-CAR provided herein is included in a viral vector. Examples of suitable virus vectors include retrovirus (e.g., MoML V or lentivirus), adenovirus, adeno-associated virus, vaccinia virus, and fowlpox vectors. In specific examples, the CD147-CAR encoding nucleic acid is included in a MoMLV vector, such as an SFG retroviral vector or a pHAGE-CPPT lentiviral vector. In other examples, the vector may be a DNA vector.

Figures 23A, 23B:
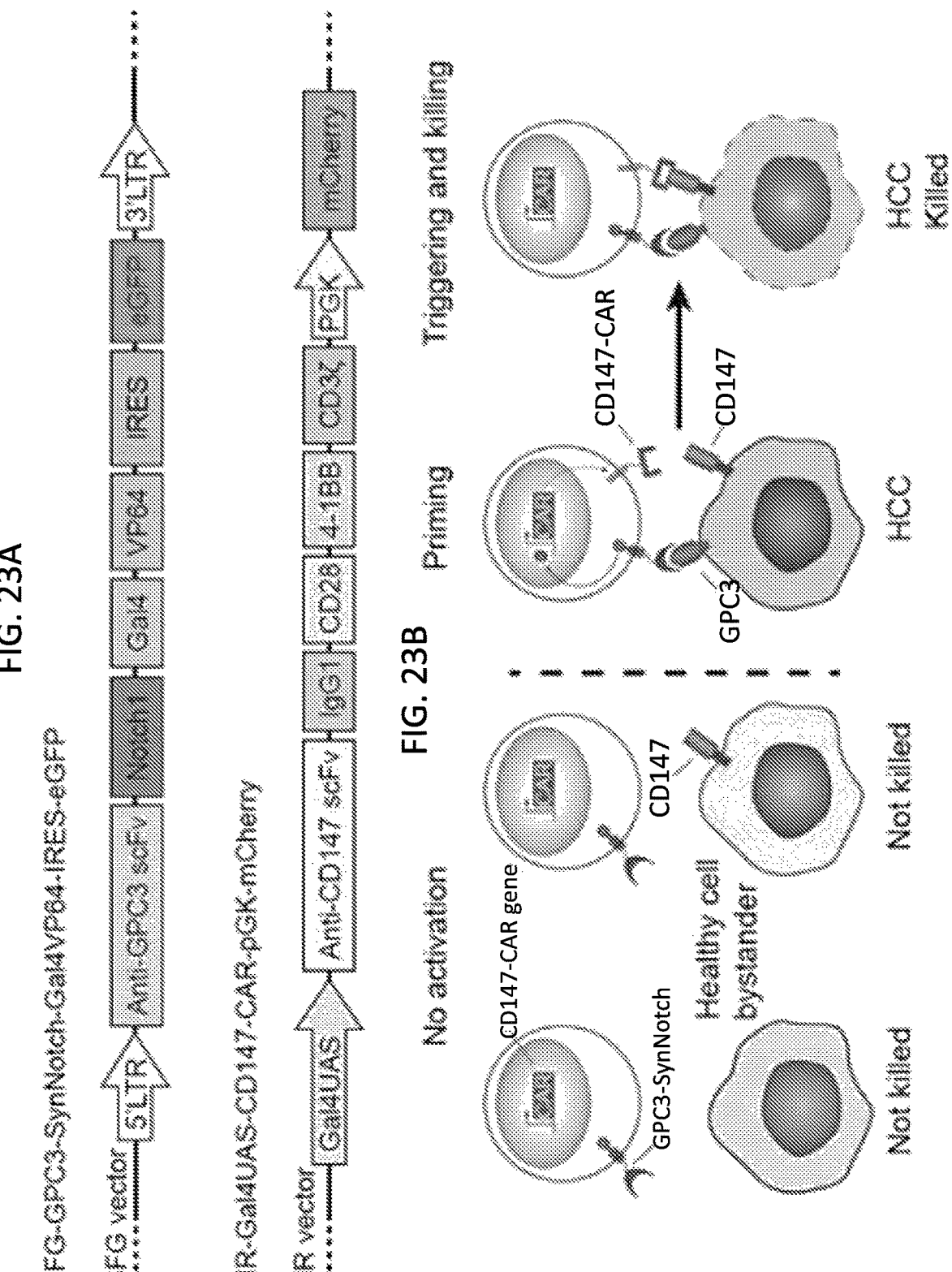
FIGS. 23A-23H demonstrate that SynNotch GPC3-inducible CD147-CAR T cells selectively target GPC3+CD147+ HepG2 cells but not GPC3+CD147− or GPC3-CD147+ HepG2 cells.

In some embodiments, the vector further includes an upstream activation sequence (UAS) that permits inducible expression of the CD147-CAR. In one non-limiting example, the UAS is a Gal4 UAS, which is activated by Gal4. However, one of skill in the art can identify other trans-activation systems that could be utilized. In one example, a Gal4UAS CD147-CAR nucleic acid includes a nucleic acid sequence with at least 90% sequence identity (for example, at least 91%, at least 92%, at least 93%, at least 94%, at least 95%, at least 96%, at least 97%, at least 98% at least 99%, or 100% identity) to SEQ ID NO: 14. An exemplary vector encoding a Gal4UAS CD147-CAR construct is shown in FIG. 23A, such as pHR_Gal4UAS-CD147-CAR-pGK_mCherry. In some examples, the vector includes a nucleic acid sequence with at least 90% sequence identity (for example, at least 91%, at least 92%, at least 93%, at least 94%, at least 95%, at least 96%, at least 97%, at least 98% at least 99%, or 100% identity) to SEQ ID NO: 15. In some examples, the vector includes a selectable marker (such as mCherry in SEQ ID NO: 15), but in other examples, the selectable marker is not included in the vector.

In some examples, the vector further includes a nucleic acid sequence encoding at least one additional CAR. In some examples, the additional CAR is specific to an additional tumor antigen, for example, to increase specificity of targeting of the CD147-CAR to tumor cells expressing or overexpressing CD147. In some examples, the vector includes a nucleic acid encoding one or more CARs including an antigen binding domain that specifically binds to a liver cancer antigen, such as one or more of glypican-3, alpha-fetoprotein, or mucin-1. Additional tumor antigens/CARs can be selected based on the type of cancer being treated. In other examples, the vector includes a nucleic acid encoding a CAR encoding a CAR including an antigen binding domain specific for hepatitis B or hepatitis C. In some examples, the additional CAR binds to a HBV envelope protein or hepatitis B surface antigen (HBsAg). In other examples, the additional CAR binds to HCV E2 glycoprotein. In some examples, the one or more additional CARs are included in the vector with the CD147-CAR, for example, separated by a self-cleaving peptide, such as a P2A peptide sequence.

V. Cells Expressing CD147 CARs or CD147-Specific Binding Agents

Also provided herein are cells (for example, immune cells) that express the disclosed CD147-CARs or CD147-specific binding agents. In particular embodiments, the cells include T cells, NK cells, NKT cells, DNT cells, neutrophils, or macrophages. In some embodiments, the cells are T cells, NK cells, or macrophages expressing a CD147-CAR.

In some examples, the cells further express a GPC3-specific binding agent, such as an anti-GPC3 scFV. In particular examples, the cells express an anti-GPC3 scFV operably linked to a nucleic acid encoding Gal4-VP64 (e.g., a SynNotch construct). When GPC3 binds to the protein encoded by this construct, Gal4-VP64 is activated, and can induce expression of a construct with a Gal4-responsive element (such as Gal4UAS). An exemplary vector encoding an anti-GPC3 scFv SynNotch inducer construct is shown in FIG. 23A. Thus, in some examples, the T cells, NK cells, NKT cells, DNT cells, neutrophils, or macrophages express an inducible CD147-CAR (e.g., SEQ ID NO: 14) and an anti-GPC3 binding agent construct that induces expression of the inducible CD147-CAR.

In other embodiments, the cells are T cells, NK cells, NKT cells, DNT cells, neutrophils, or macrophages expressing a CD147-specific binding agent, such as a CD147 scFv (for example, SEQ ID NO: 1) and a GPC3-CAR. In some examples, the GPC3-CAR includes a nucleic acid sequence with at least 90% sequence identity (for example, at least 91%, at least 92%, at least 93%, at least 94%, at least 95%, at least 96%, at least 97%, at least 98% at least 99%, or 100% identity) to SEQ ID NO: 16. In particular examples, the cells express an anti-CD147 scFV operably linked to a nucleic acid encoding Gal4-VP64 (e.g., a SynNotch construct). When CD147 binds to the protein encoded by this construct, Gal4-VP64 is activated, and can induce expression of a construct with a Gal4-responsive element (such as Gal4UAS). Exemplary vectors encoding an anti-CD147 scFv SynNotch inducer construct and an anti-GPC3-CAR are shown in FIG. 25A. Thus, in some examples, the T cells, NK cells, NKT cells, DNT cells, neutrophils, macrophages express an inducible GPC3-CAR (e.g., SEQ ID NO: 16) and an anti-CD147 binding agent construct that induces expression of the inducible GPC3-CAR.

In some examples, the immune cells are transduced or transfected with one or more expression vectors including one or more nucleic acids, including nucleic acids encoding a CD147-CAR, an inducible GPC3-CAR, an inducible CD147-CAR, a CD147-specific binding agent operably linked to an inducer, a GPC3-specific binding agent operably linked to an inducer, or any combination of two or more thereof. In other examples, the vector (or a DNA encoding the construct) may be introduced by contacting the cells with a nanoparticle including the vector or DNA. In some examples, the cells are irradiated following transduction or transfection (e.g., treated with y-irradiation, such as at a dose of at least 1,000, at least 2,000, at least 3,000, at least 5,000, at least 7,000, at least 8,000, at least 9,000, at least 10,000, at least 11,000, at least 12,000, or at least 15,000 or about 1,000-15,000, 2,000-12,000, 1,000-5,000, 5,000-10,000, or 8,000-12,000, or about 10,000 Rad), for example, prior to administering to a subject.

In some examples, the transduced or transfected cells are isolated T cells (such as a primary T cell or T cells obtained from a subject), isolated NK cells (such as a primary NK cell or NK cells obtained from a subject), isolated NKT cells, isolated DNT cells, isolated neutrophils, or isolated macrophages (such as a primary macrophage or macrophages obtained from a subject). In some examples, the T cells, NK cells, NKT cells, DNT cells, neutrophils, or macrophages are obtained from peripheral blood, umbilical cord blood, lymph node tissue, bone marrow, or tumor tissue. In some examples, T cells, NK cells, NKT cells, or DNT cells are also enriched, purified, and/or expanded from a sample from a subject, for example before and/or after transduction with one or more of the disclosed expression vectors.

In one non-limiting embodiment, the cell is an NK-92 cell. NK-92 cells are a NK cell line derived from a patient with non-Hodgkin's lymphoma (e.g., ATCC® CRL-2407™). This cell line has properties of activated NK cells (see, e.g., Gong et al., *Leukemia* 8:652-658, 1994). In another embodiment, the cell is an NK-92MI cell (e.g., ATCC® CRL-2408™). The NK-92MI cell line is an interleukin-2 (IL-2) independent NK cell line, derived from NK-92, which stably expresses human IL-2 (see, e.g., Tam et al., *Hum. Gene Ther.* 10:1359-1373, 1999). NK-92 or NK-92MI cells expressing a CAR (such as a CD147-CAR and/or other nucleic acids disclosed herein) can be used herein as an "off the shelf" immunotherapy, since autologous NK cells do not have to be produced for each subject. Other NK cell lines that can be used with the CD147-CARs (or other nucleic acids) described herein include NKL, KHYG-1, and YTS cells.

NK-92-mediated immunotherapy is now undergoing phase I/II clinical trials (Arai et al., 2008; Tonn et al., 2013). Commonly, NK-92 cells must be irradiated prior to infusion to prevent permanent engraftment. The amount of irradiation required is around 10 Gy. The dose of irradiated NK-92 infusion can be up to $10^{10}$ NK92 cells/m$^2$. Importantly, irradiated NK-92 cells have been shown to be safe for infusion in patients, as demonstrated by several NK-92 clinical trials (NCT00900809, NCT00990717, NCT00995137, and NCT01974479).

In some non-limiting embodiments, immune cells are transduced with a vector encoding a CD147-CAR. Following transduction, cells expressing the CD147-CAR can be detected and/or enriched, for example, by flow cytometry using a labeled antibody that binds to CD147. In some examples, the transduced cells (such as NK cells or T cells) are expanded, for example, by cell culture for a period of time following transduction. In some examples, some or all of the modified cells are cryopreserved for later use.

VI. Methods of Immunotherapy

Provided are methods of treating cancer (such as a cancer expressing or overexpressing CD147) in a subject with a CD147-CAR disclosed herein. In some embodiments, the methods include administering to the subject a composition including a modified T cell, NK cell, NKT cell, DNT cell, neutrophil, or macrophage expressing a CD147-CAR (for example, transduced with a vector encoding the CAR) and a pharmaceutically acceptable carrier. In other examples, the methods include administering to the subject a pharmaceutical composition including an expression vector encoding a CD147-CAR and a pharmaceutically acceptable carrier.

Also provided are methods of treating cancer (such as a cancer expressing or overexpressing CD147) in a subject with an inducible CD147-CAR and a GPC3-specific binding agent linked to expression of an inducer of the inducible CD147-CAR disclosed herein. In some embodiments, the methods include administering to the subject a composition including a modified T cell, NK cell, NKT cell, DNT cell, neutrophil, or macrophage expressing an inducible CD147-CAR and a GPC3-specific binding agent linked to an inducer (for example, transduced with one or more vectors encoding the CD147-CAR and the GPC3-specific binding agent) and a pharmaceutically acceptable carrier. In other examples, the methods include administering to the subject one or more expression vectors encoding the inducible CD147-CAR (e.g., SEQ ID NO: 15) and the GPC3-specific binding agent linked to the inducer and a pharmaceutically acceptable carrier.

Also provided are methods of treating cancer (such as a cancer expressing or overexpressing CD147) in a subject with an inducible GPC3-CAR and a CD147-specific binding agent disclosed herein linked to an inducer of the inducible GPC3-CAR. In some embodiments, the methods include administering to the subject a composition including a modified T cell, NK cell, NKT cell, DNT cell, neutrophil, or macrophage expressing an inducible GPC3-CAR and a CD147-specific binding agent linked to the inducer (for example, transduced with one or more vectors encoding the GPC3-CAR (e.g., SEQ ID NO: 16) and the CD147-specific binding agent) and a pharmaceutically acceptable carrier. In other examples, the methods include administering to the subject one or more expression vectors encoding the inducible GPC3-CAR and the CD147-specific binding agent linked to the inducer and a pharmaceutically acceptable carrier.

The modified cells (such as T cells, NK cells, NKT cells, DNT cells, neutrophils, or macrophages) expressing a CD147-CAR or CD147-specific binding agent described herein can be incorporated into pharmaceutical compositions. Such compositions typically include a population of cells (such as CD147-CAR-NK cells or CD147-CAR-T cells) and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (see, e.g., *Remington: The Science and Practice of Pharmacy*, The University of the Sciences in Philadelphia, Editor, Lippincott, Williams, & Wilkins, Philadelphia, PA, $21^{st}$ Edition, 2005). Examples of such carriers or diluents include, but are not limited to, water, saline, Ringer's solutions, dextrose solution, balanced salt solutions, and 5% human serum albumin. Liposomes and non-aqueous vehicles such as fixed oils may also be used. Supplementary active compounds can also be incorporated into the compositions. Actual methods for preparing administrable compositions include those provided in *Remington: The Science and Practice of Pharmacy*, The University of the Sciences in Philadelphia, Editor, Lippincott, Williams, & Wilkins, Philadelphia, PA, $21^{st}$ Edition (2005).

In some examples, the composition includes about $10^4$ to $10^{12}$ of the modified NK cells or T cells (for example, about $10^4$-$10^8$ cells, about $10^6$-$10^8$ cells, or about $10^6$-$10^{12}$ cells). For example, the composition may be prepared such that about $10^4$ to $10^{10}$ modified NK cells or modified T cells cells/kg (such as about $10^4$, $10^5$, $10^6$, $10^7$, or $10^8$ cells/kg) are administered to a subject. In specific examples, the composition includes at least $10^4$, $10^5$, $10^6$, or $10^7$ CD147-CAR-NK cells or CD147-CAR-T cells. The population of modified NK cells or modified T cells is typically administered parenterally, for example intravenously; however, injection or infusion to a tumor or close to a tumor (local administration) or administration to the peritoneal cavity can also be used. Appropriate routes of administration can be determined based on factors such as the subject, the condition being treated, and other factors.

Multiple doses of the population of modified NK cells or modified T cells can be administered to a subject. For example, CD147-CAR-NK cells or CD147-CAR-T cells can be administered daily, every other day, twice per week, weekly, every other week, every three weeks, monthly, or less frequently. A skilled clinician can select an administration schedule based on the subject, the condition being treated, the previous treatment history, and other factors.

In additional examples, the subject is also administered at least one, at least one, at least two, at least three, or at least four cytokine(s) (such as IL-2, IL-15, IL-21, and/or IL-12) to support survival and/or growth of the modified NK cells or modified T cells. In specific, non-limiting examples, at least one cytokine includes IL-2 and IL-15. The cytokine(s) are administered before, after, or substantially simultaneously with the modified NK cells or modified T cells. In specific examples, at least one cytokine (e.g., IL-2) is administered simultaneously, for example, with CD147-CAR-NK cells.

In some examples, the subject being treated has a solid tumor, for example, a solid tumor expressing CD147.

Examples of solid tumors, include sarcomas (such as fibrosarcoma, myxosarcoma, liposarcoma, chondrosarcoma, osteosarcoma, soft tissue sarcoma, and other sarcomas), synovioma, mesothelioma, Ewing sarcoma, leiomyosarcoma, rhabdomyosarcoma, colon cancer, colorectal cancer, peritoneal cancer, esophageal cancer (such as esophageal squamous cell carcinoma), pancreatic cancer, breast cancer (including basal breast carcinoma, ductal carcinoma and lobular breast carcinoma), endometrial cancer, lung cancer (such as non-small cell lung cancer), ovarian cancer, prostate cancer, liver cancer (including hepatocellular carcinoma), gastric cancer, squamous cell carcinoma (including head and neck squamous cell carcinoma), basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, hepatoma, bile duct carcinoma, choriocarcinoma, Wilms tumor, cervical cancer, fallopian tube cancer, testicular tumor, seminoma, bladder cancer (such as renal cell cancer), melanoma, and CNS tumors (such as a glioma, glioblastoma, astrocytoma, medulloblastoma, craniopharyrgioma, ependymoma, pinealoma, hemangioblastoma, acoustic neuroma, oligodendroglioma, meningioma, neuroblastoma and retinoblastoma). Solid tumors also include tumor metastases (for example, metastases to the lung, liver, brain, or bone). In some examples, the subject has hepatocellular carcinoma, neuroblastoma, breast cancer, gastric cancer, endometrial cancer, bladder cancer (such as renal cell carcinoma), lung cancer (such as non-small cell lung cancer), cervical cancer, medulloblastoma, esophageal cancer (such as esophageal squamous cell carcinoma), prostate cancer, seminoma, glioblastoma, osteosarcoma, astrocytoma, or soft tissue sarcoma. In particular examples, the subject has hepatocellular carcinoma or neuroblastoma.

In other examples, the subject has a hematological malignancy, for example, a hematological malignancy expressing CD147. Examples of hematological malignancies include leukemias, including acute leukemias (such as 11q23-positive acute leukemia, acute lymphocytic leukemia (ALL), T-cell ALL, acute myelocytic leukemia, acute myelogenous leukemia (AML), and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), lymphoblastic leukemia, polycythemia vera, lymphoma, diffuse large B cell lymphoma, Burkitt lymphoma, T cell lymphoma, follicular lymphoma, mantle cell lymphoma, Hodgkin disease, non-Hodgkin lymphoma, multiple myeloma, Waldenstrom macroglobulinemia, heavy chain disease, myelodysplastic syndrome, hairy cell leukemia, and myelodysplasia. In particular examples, the subject has acute lymphocytic leukemia (ALL), T-cell ALL, acute myelocytic leukemia, or acute myelogenous leukemia (AML).

In some examples, the subject is also treated with one or more of surgery, radiation therapy and chemotherapeutic agents. Exemplary chemotherapeutic agents include (but are not limited to) alkylating agents, such as nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine); antimetabolites such as folic acid analogs (such as methotrexate), pyrimidine analogs (such as 5-FU or cytarabine), and purine analogs, such as mercaptopurine or thioguanine; or natural products, for example vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mito-cycin C), and enzymes (such as L-asparaginase). Additional agents include platinum coordination complexes (such as cis-diamine-dichloroplatinum II, also known as cisplatin), substituted ureas (such as hydroxyurea), methyl hydrazine derivatives (such as procarbazine), and adrenocrotical sup-pressants (such as mitotane and aminoglutethimide); hor-mones and antagonists, such as adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytara-bine), carmustine, busulfan, lomustine, carboplatinum, cis-platinum, cyclophosphamide (Cytoxan®), daunorubicin, dacarbazine, 5-fluorouracil, fludarabine, hydroxyurea, ida-rubicin, ifosfamide, methotrexate, mithramycin, mitomycin, mitoxantrone, nitrogen mustard, paclitaxel (or other taxanes, such as docetaxel), vinblastine, vincristine, VP-16, while newer drugs include gemcitabine (Gemzar®), trastuzumab (Herceptin®), irinotecan (CPT-11), leustatin, navelbine, rit-uximab (Rituxan®) imatinib (STI-571), Topotecan (Hyca-mtin®), capecitabine, ibritumomab (Zevalin®), and calcit-riol. A skilled clinician can select appropriate additional therapies (from those listed here or other current therapies) for the subject, depending on factors such as the subject, the cancer being treated, treatment history, and other factors.

EXAMPLES

The following examples are provided to illustrate certain particular features and/or embodiments. These examples should not be construed to limit the disclosure to the particular features or embodiments described.

Example 1

Materials and Methods

Antibodies and Reagents: Purified anti-CD247 (also known as T-cell surface Glycoprotein CD3 Zeta Chain, CD3) antibody (clone 6B10.2, BioLegend), purified anti-human CD147, FITC-conjugated anti-human CD147 (clone HIM6, BioLegend), PE- or APC-conjugated anti-human CD3 antibody (clone OKT3, BioLegend), FITC or BV 510-conjugated anti-human CD56 antibody (clone HCD56, BioLegend), PE-conjugated anti-human CD69 antibody (clone FN50, BioLegend), APC/Fire 750-conjugated anti-human CD226 antibody (also known as DNAM-1, clone 11A8, BioLegend), APC/Fire 750-conjugated anti-human KLRG1 (MAFA) antibody (clone SA231A2, BioLegend), BV421-conjugated anti-human CD335 (NKp46) antibody (clone 9E2, BioLegend), PE/Cy7-conjugated anti-human CD158b (KIR2DL2/L3, BioLegend) antibody (clone DX27, BioLegend), PE/Cy7-conjugated anti-human CD244 (2B4) antibody (clone C1.7, BioLegend), PE-conjugated anti-hu-man CD152 (CTLA-4) antibody (clone BNI3), APC-conju-gated anti-human CD366 (Tim-3) antibody (clone F38-2E2), PerCP/Cy5.5 anti-human TIGIT (VSTM3) antibody (clone A15153G), FITC-conjugated anti-human CD223 (LAG-3) antibody (clone 11C3C65, BioLegend), and PerCP/Cy5.5-conjugated anti-human CD94 (clone DX22, BioLegend) were purchased from BioLegend (San Diego, CA, USA).

APC-conjugated anti-human CD16 antibody (clone B73.1, BD Biosciences), FITC-conjugated anti-human CD3 antibody (clone UCHT1, BD Biosciences), BV480-conju-gated anti-human CD85j antibody (LIR-1) antibody (clone GHI/75, BD Biosciences), BV711-conjugated anti-human CD314 (NKG2D) antibody (clone 1D11, BD Biosciences), and PE- or FITC-conjugated anti-human CD107a antibody (clone H4A3, BD Biosciences) were purchased from BD Biosciences (San Jose, CA, USA).

FITC-conjugated anti-human KIR/CD158 antibody (clone 180704, R&D Systems), PE-conjugated anti-human KIR2DL1/KIR2DS5 antibody (clone 143211, R&D Sys-tems), APC-conjugated anti-human KIR3DL1 antibody (clone DX9, R&D Systems), AF405-conjugated anti-human KIR3DL2/CD158k antibody (clone 539304, R&D Sys-tems), APC-conjugated anti-human NKG2A/CD159a anti-body (clone 131411, R&D Systems), and PE-conjugated anti-human NKG2C/CD159c antibody (clone 134591, R&D Systems) were purchased from R&D Systems. AF647 Goat anti-human IgG F (ab) 2 fragment antibody was purchased from Jackson ImmunoResearch (West Grove, PA, USA).

Bioinformatic analysis from public cancer patient data-base: Patient survival data and RSEM (RNA-Seq by Expec-tation Maximization) normalized expression datasets about CD147 were generated from The Cancer Genome Atlas (TCGA) and were downloaded from OncoLnc (oncoln-c.org). Data were plotted for Kaplan-Meier curves using GraphPad Prism 5.0 (GraphPad). RSEM normalized expres-sion datasets derived from TCGA come from FireHose Broad GDAC, which was developed by The Broad Institute (gdac.broadinstitute.org). Figures were generated by Graph-Pad Prism 5.

Cell lines: 293T, K562, Daudi cell, SK-Hep1, and HepG2 cell lines were purchased from American Type Culture Collection (ATCC). To establish the Daudi-FFluc cell, CD147-positive HepG2 and SK-Hep1 cells were transduced with the lentiviral vector encoding FFLuc-GFP, as previ-ously described. The protocol for collection of peripheral blood from healthy donors was approved by the institutional review board (IRB) and ethics review committees at the Rutgers-New Jersey Medical School (Newark, NJ).

NK-92MI cell culture and generation of CAR-modified NK-92MI cells: NK-92MI cell line was purchased from ATCC® (CRL-2408TM, USA). NK-92MI, an interleukin-2 (IL-2) independent NK cell line, is derived from NK-92 (ATCC® CRL-2407TM) cell line (Gong et al., *Leukemia* 8:652-658, 1994) stably expressed with human IL-2 cDNA (Tam et al., *Hum Gene Ther* 10:1359-1373, 1999; Tam et al., *J. Hematother.* 8:281-290, 1999). NK-92MI cell lines were maintained in the specific NK-92MI culture medium (alpha minimum essential medium, alpha-MEM) without ribo-nucleosides and deoxyribonucleosides but with 2 mM L-glu-tamine and 1.5 g/L sodium bicarbonate. To make the com-plete growth medium, the following components were added to the base medium: 0.2 mM inositol, 0.1 mM 2-mercapto-ethanol, 0.02 mM folic acid, horse serum to a final concen-tration of 12.5%, and fetal bovine serum to a final concen-tration of 12.5%. NK-92MI cells were transduced with retroviral supernatants on day 3 in plates coated with recom-binant fibronectin fragment (FN CH-296; Retronectin; Takara, Japan). After transduction, NK cells were expanded using IL-2. To check the percentage of CD147-CAR expression on NK-92MI cells, these cells were stained for CD3 and CD56 to stain NK cells, followed by Flow Cytometry analysis.

Generation of CD147-knockout cell line: To generate the CD147 knock-out hepatocellular cell line, a lentiviral delivery system was used, guide RNA targeting CD147 sequence: #1 (5-TTGACATCGTTGGCCACCGC-3; SEQ ID NO: 10), #3 (5-GTGGACGCAGATGACCGCTC-3; SEQ ID NO: 11). Lentivirus was produced in HEK 293T by transfecting lenti-CRISPR v2 with packaging plasmids pSPAX2 and pMD2G. After 3 days, supernatants were filtered (0.45 μm) and incubated with hepatocellular cell cells and 8 μg/mL polybrene (Sigma). After 48 hours incubation, transduced cells were changed to fresh medium and selected with 8.0 μg/ml puromycin for 5 days. Western blots and flow cytometry analysis were performed to confirm the efficacy of the knockout cell lines.

Plasmid construction and retrovirus production: A codon-optimized DNA fragment was synthesized by GENEWIZ encoding the CD147-specific scFv from the 5F6 clone and sub-cloned in-frame into the SFG retroviral vector retroviral backbone in-frame with the hinge component of human IgG1, CD28 trans-membrane domain, intracellular domain CD28 plus 4-1BB, and the & chain of the human TCR/CD3 complex. To produce CD147-CAR retrovirus, 293T cells were transfected with a combination of plasmid containing CD147-specific scFv, RDF, and PegPam3, as previously described (Loskog et al., *Leukemia* 20:1819-1828, 2006). The construct of CD19-CD28-CAR and CD19-4-1BB-CAR has been previously described (Xiong et al., *Mol. Ther.* 26:963-975, 2018).

Transduction of NK-92MI cells with CD147-CAR: NK cells were harvested on day 7 of expansion and transduced with CD147-CAR retrovirus in plates coated with Retronectin (FN CH-296, Takara, Japan). Two days later, cells were transferred to G-Rex 6 multi-well cell culture plates and maintained in 35 ml of complete RPMI-1640 media with 200 U/ml IL-2 (PeproTech). The medium was changed every 3-4 days and $2 \times 10^7$ cells were kept in each well for continued culture at each time. Total cell numbers were counted using Trypan Blue exclusion. To check the percentage of NK cells and the expression of CAR, cells were stained for CD3, CD56, and IgG F(ab')$_2$, and analyzed by Flow Cytometry.

Flow Cytometry Analysis and Sorting: CAR-NK cells were stained with fluorescence-conjugated antibodies in FACS staining buffer with 1% fetal bovine serum (FBS) on ice for 30 minutes, washed with PBS, and analyzed on a FACS LSRII or an LSR Fortessa flow cytometer (BD). PMT voltages were adjusted and compensation values were calculated before data collection. Data were acquired using FACS Diva software (BD) and analyzed using FlowJo software (Tree Star).

For the flow cytometry single live cell sorting, all of the sample cells were stained with fluorescence-conjugated antibodies with (RPMI1640 with 1% FBS) on ice for 30 minutes, washed with PBS twice, re-suspended in completed culture medium, and sorted by SORP BD FACS Aria III. After sorting, collection samples were washed with pre-warmed medium once, and cultured for use.

CAR-NK Degranulation assay (CD107a): CAR-NK cells ($1 \times 10^5$) were incubated with target cells in U-bottomed 96-well plates in complete NK-92MI culture media at 37° C. for 4 hours or overnight. Afterward, cells were harvested, washed, stained for CD3, CD56, and CD107a with GolgiStop (BD) for 30 minutes on ice, and analyzed by flow cytometry.

Cytokine release assays: The IFN gamma and TNF-alpha cytokines secreted by the CAR-NK were measured by a commercial ELISA kit (Invitrogen-Thermo Fisher Scientific) as per the manufacturer's protocol.

$^{51}$Cr release assay: To evaluate the cytotoxic activity of CAR-NK cell, a standard 4-hour $^{51}$Cr release assay was used. Briefly, target cells were labeled with $^{51}$Cr at 37° C. for 2 hours and then resuspended at $2 \times 10^5$/mL in NK-92MI culture medium with 10% FBS without IL2. Then, $2 \times 10^4$ target cells were incubated with serial-diluted CAR-NK cells at 37° C. for 4 hours. After centrifugation, the supernatants were collected and the released $^{51}$Cr was measured with a gamma counter (Wallac, Turku, Finland). The cytotoxicity (as a percentage) was calculated as follows: [(sample−spontaneous release)/(maximum release−spontaneous release)]×100.

FFLuc reporter system assay: To quantify the cytotoxicity of CAR-modified immune cells, a FFLuc reporter system assay was developed. Briefly, at day 1, target cells were pre-seeded at $2 \times 10^4$ or $3 \times 10^4$ target cells/well (FFluc-GFP stably transduced cell) onto an optical 96-well plate (Greiner Bio-One™ No.: 655098) in 100 μl/well of the target cell's full nutrition medium and incubation at 37° C. with 5% CO$_2$ overnight. The next day, serial dilution of the effector cell was prepared according to the ratio of effector/target and the indicated effector cells were added into each well (100 μl/well). The reaction was incubated at 37° C. with 5% CO$_2$ for 4 hours and then the supernatant was gently discarded. 100 μl working D-Luciferin was added to each well and incubated at 37° C. with 5% CO$_2$ for 5 mins, with the lights turned off. A microplate reader (PerkinElmer, USA) was used to quantify the data. The data were quantified by converting the obtained values to percentage of specific lysis by the following equation: Specific Lysis Percentage (%)= $[1−(S−E)/(T−M)]*100$, where S is the value of luminescence of the sample well, E is the value of luminescence of the "effector cell only" well compared to the sample well, T is the mean value of luminescence of "Target cell only" wells, and M is the mean value of luminescence of "blank medium only" wells.

Animal Studies: All animal experiments were approved by the Institutional Animal Care and Use Committee (IACUC). NOD.Cg-Prkdc$^{scid}$ Il2rg$^{tm1wjl}$/SzJ (NSG) mice from The Jackson Laboratory (Bar Harbor, ME) were used for all in vivo experiments. To establish a hepatocellular carcinoma cell line xenograft model, both male and female NSG mice (8-week-old) were injected subcutaneously with $4 \times 10^6$ SK-Hep1 cells in 100 μL of PBS Corning® Matrigel® Matrix in the right flank. When the tumor burden reached ~40-50 mm$^2$, mice were randomly allocated into three groups. Beginning treatment on day 1, the mice were injected (i.v.) with $5 \times 10^6$ CD147-CAR-NK-92MI cells in 100 μL of PBS. Control groups were infused with parental NK-92MI cells or vehicle (PBS). On the next day (day 2), all the animals were injected (i.v.) with IL-2 (20,000 units/mouse). Animal weight and tumor burden were collected twice a week. The tumor size was measured by a caliper and the greatest longitudinal diameter (length) and the greatest transverse diameter (width) were recorded. Tumor sizes based on caliper measurements were calculated by the modified ellipsoidal formula. The tumor size was calculated as follows: Tumor size (mm$^2$)=½(length×width$^2$). When the tumor burden was above 2000 mm$^2$ or the animal's weight reduced >20%, mice were euthanized according to IACUC guidelines. The animal survival data were recorded simultaneously.

For the patient-derived xenograft (PDX) model, patient hepatocellular carcinoma animal models were developed by The Jackson Laboratory. Briefly, fresh PDX specimens were implanted subcutaneously into the flanks of 6-8 week old NOD SCID gamma (NSG) mice. After the tumor burden reached ~40-50 mm², mice were randomly allocated into three groups for further analysis. The main treatment procedure used was as described above. Xenografts specimens were fixed with 10% formalin, embedded in paraffin for cutting, and processed for IHC staining or were directly frozen into liquid nitrogen for further analysis.

Statistical Analysis: Tumor size statistical analysis was performed by two-way ANOVA with Bonferroni post-tests. The overall survival statistics were calculated using the log-rank test. Other statistical significance was determined using a two-tailed unpaired Student's t test and a two-tailed paired Student's t test. All statistical calculation graphs were generated by GraphPad Prism 5.0. P<0.05 (*), P<0.01(), and P<0.001(*) were considered statistically significant.

Example 2

Figures 1B, 1C, 1D:
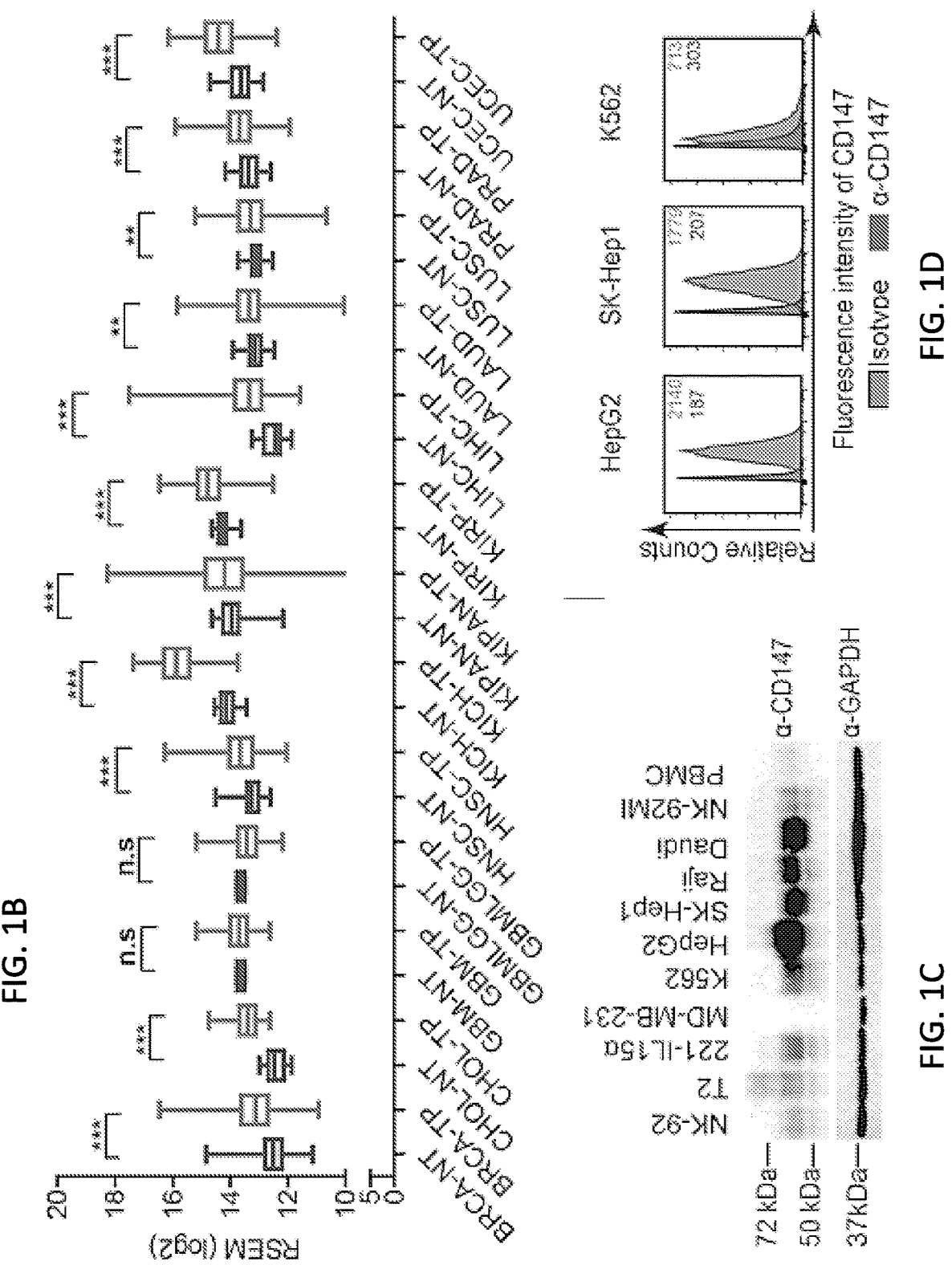

CD147 is Expressed in Hepatocellular Carcinoma Cell Lines and Liver Cancer Specimens from Patients To determine whether CD147 is an effective, valid target for hepatocellular carcinoma and other types of cancer, the correlation between patient survival and expression level of CD147 from TCGA (The Cancer Genome Atlas, cancergenome.nih.gov) datasets was analyzed. Comparison of survival percentage from two different patient subsets (CD147$^{high}$ and CD147$^{low}$) showed that there was a strong negative correlation between CD147 and survival percentage (FIG. 1A). Specifically, CD147$^{high}$ in multiple tumor tissues demonstrated low survival percentage (FIG. 1A). In addition, a comparison of CD147 expression between normal tissue (NT) and tumor sample (TP) in multiple cancer types showed significant upregulation of CD147 expression among different types of tumor tissue (FIG. 1B).

Figure 1E:
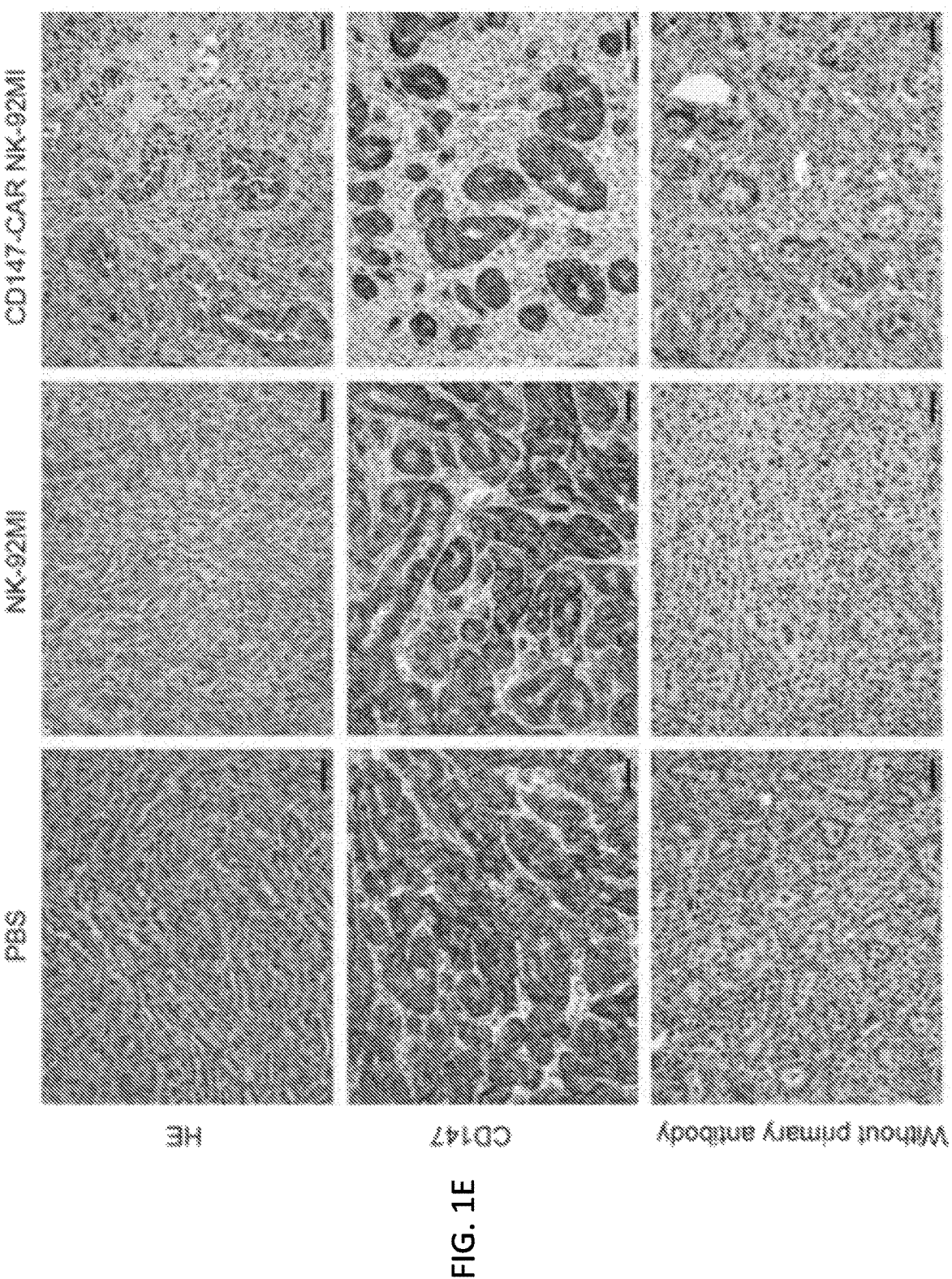

To verify the data from the bioinformatics analysis, the expression of CD147 among different tumor cell lines and other tissue was analyzed by Western-blot, which includes wildtype NK-92 (a human NK cell line), T2 (a mutant T×B cell hybrid), 721.221 (an HLA-A, -B, -C null human cell line), MDA-MB-231 (a human breast carcinoma cell line), K562 (a human myelogenous leukemia cell line), HepG2 (a human hepatocellular carcinoma cell line), SK-Hep1 (a human liver adenocarcinoma cell line), Raji (a human B lymphocyte Burkitt's lymphoma cell line), Daudi (a human B lymphoblast cell line), NK-92-MI (an interleukin 2-independent natural killer cell line), and human peripheral blood monocytes (PBMCs). CD147 molecules were highly upregulated in HepG2 and SK-Hep1 cell lines (two hepatocellular carcinoma cell lines), compared to PBMCs (FIG. 1C). The expression of CD147 on PBMCs was relatively low, compared to tumor cell lines (FIG. 1C). Similar results were obtained by flow cytometry analysis (FIG. 1D). Furthermore, the results of immunohistochemistry (IHC) assays confirmed that CD147 was significantly upregulated in HCC tissue isolated from a PDX mouse model (FIG. 1E).

Example 3

Generation and Characteristics of CD147-CAR-NK Cells

A CD147-CAR using the SFG vector (Loskog et al., *Leukemia* 20:1819-1828, 2006; Xiong et al., *Mol. Ther.*

Figures 2A, 2B, 2C:
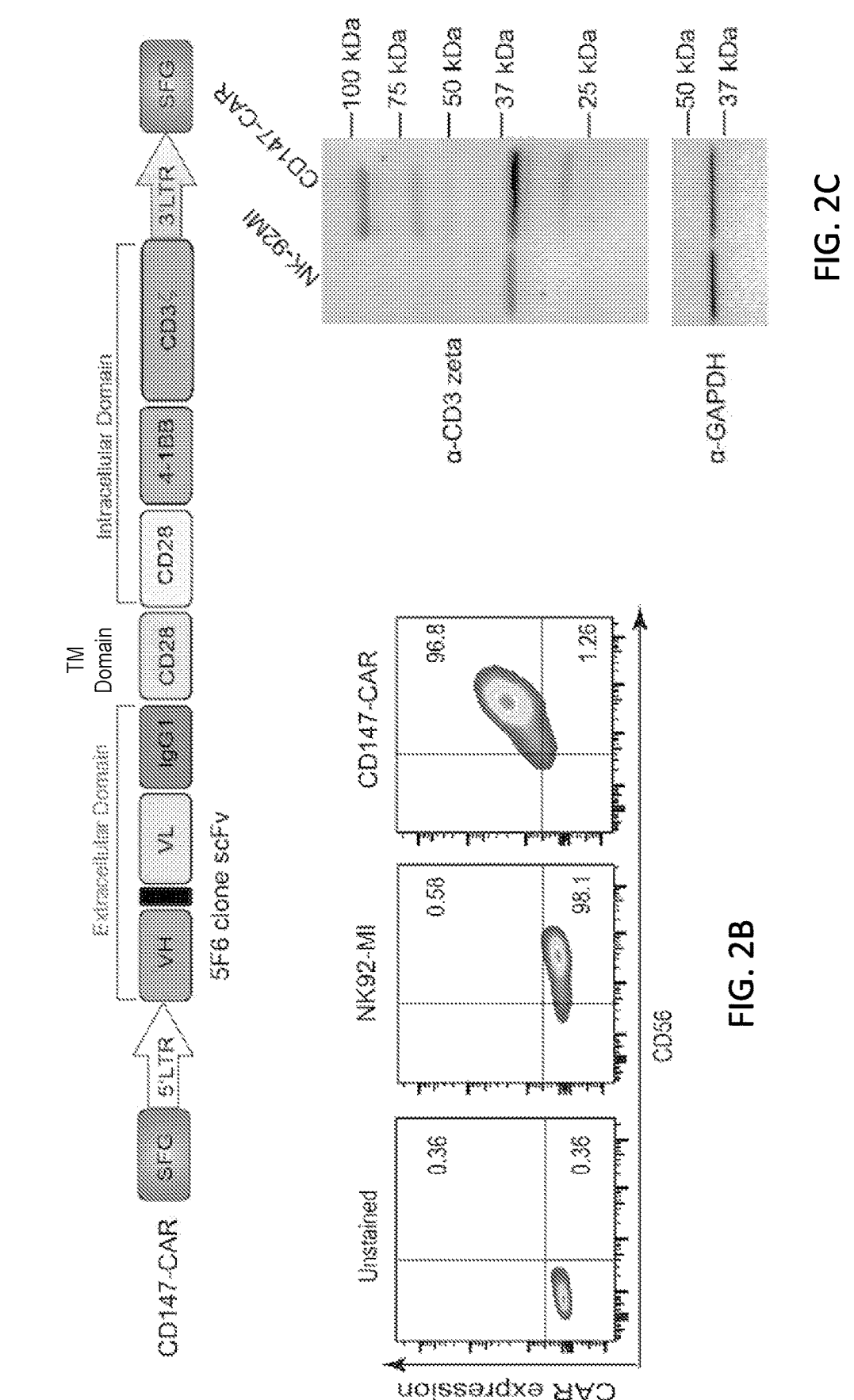
FIGS. 2A-2F show design of CD147-CAR and phenotyping of CAR-modified NK-92MI cells.

26:963-975, 2018) was constructed. The CD147-CAR contained a modified single-chain variable fragment (scFv) of anti-CD147 antibody (derived from clone 5F6, as described in Example 1), an IgG-CH2CH3 spacer, a trans-membrane domain of CD28, intracellular domain of CD28-4-1BB, and intracellular signaling domains of the TCR-zeta chain (FIG. 2A).

Figure 2D:
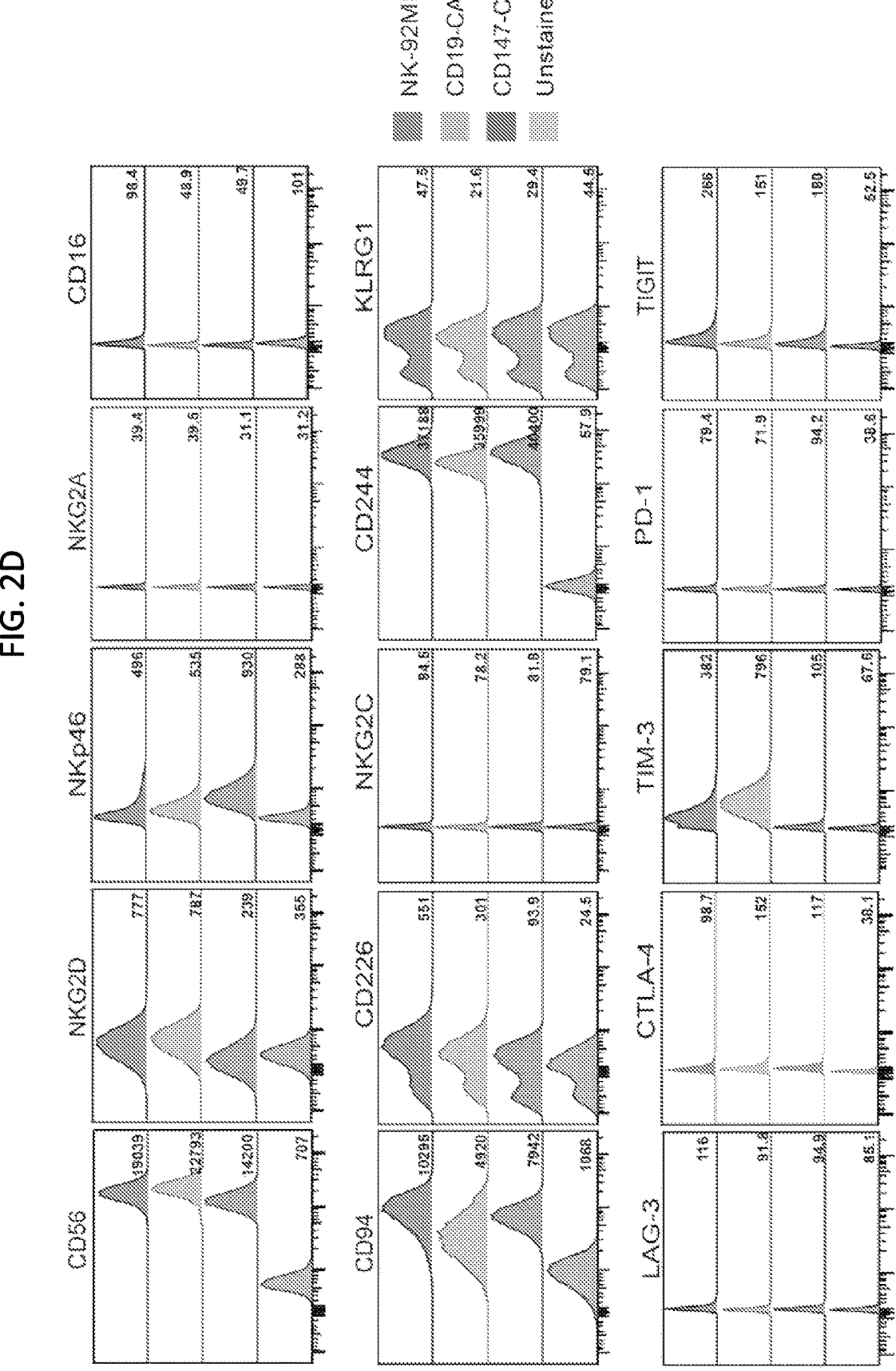
Figures 2E, 2F, 2G:
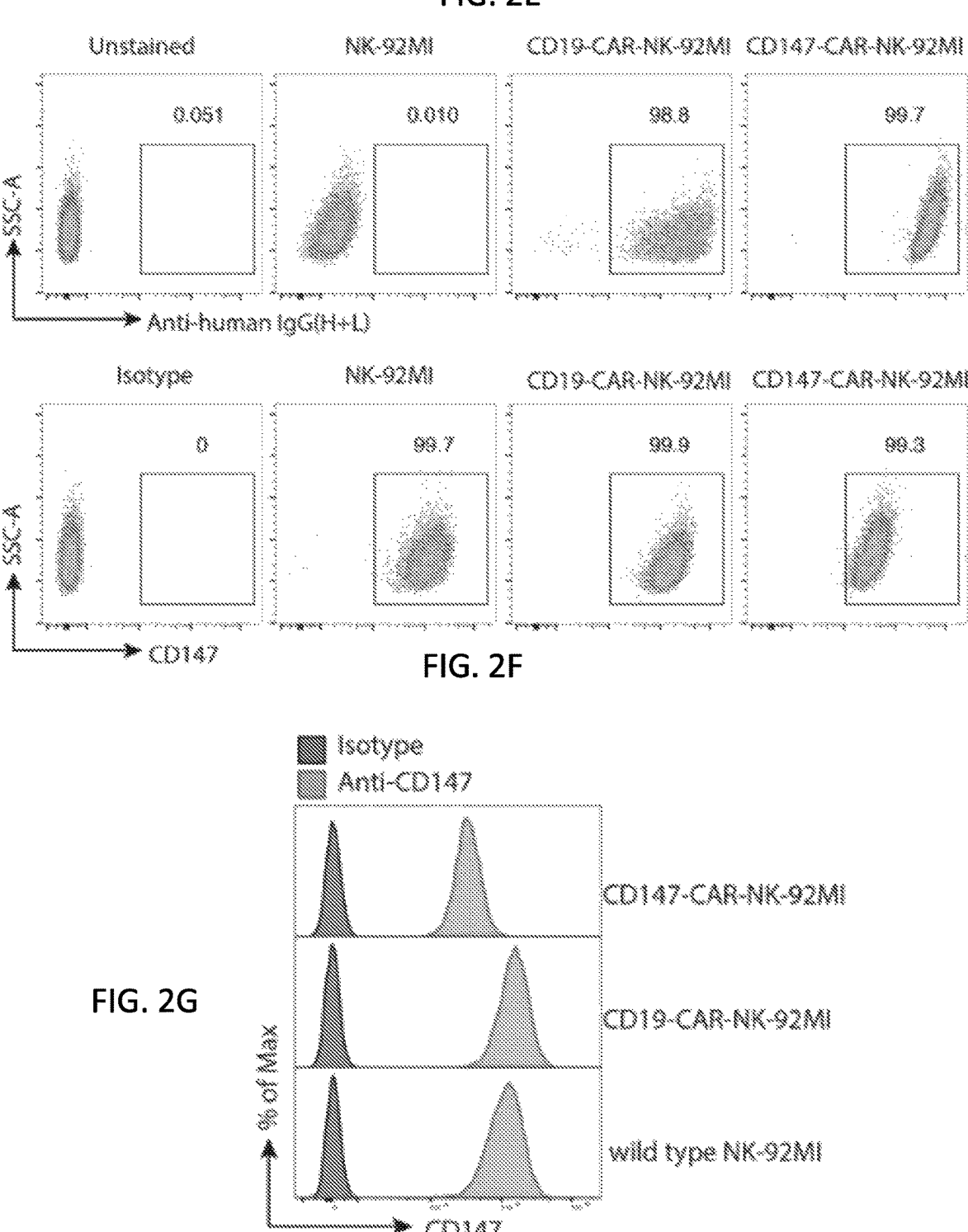
FIG. 2G shows overlaid flow cytometric profile of CD147 expression levels on NK-92MI, CD19-CAR-NK-92MI, and CD147-CAR-NK-92MI. Data are representative of two independent experiments.

First, this CAR construct was tested in the NK-92MI cell line. After transduction, NK-92MI expressed the CD147-CAR molecules (FIG. 2B). After sorting by flow cytometry, the percentage of CD147-positive NK-92MI cells was above 96% (FIG. 2B). The expression of CD147-CAR molecules in NK-92MI cells was further verified by Western blot. Compared to the parental NK-92MI cell line, the CD147-CAR-NK-92MI expressed the chimeric scFv-CD147-CAR. The approximate molecular weight was about 80-85 kD (FIG. 2C). The CD147-CAR-NK-92MI cell line was further characterized by flow cytometry. Comparable activating receptor (e.g., CD56, NKG2D, NKP46, NKG2A, CD16, CD94/NKG2C, CD226 (also known as DNAM-1), and CD244 (also known as 2B4)) and inhibitory receptor (e.g., KLRG1, LAG-3, CTLA-4, TIM-3, PD-1, and TIGIT) expression were observed (FIG. 2D). Given the low level of CD147 expression on NK92-MI cells, the expression of CD147 on CD147-CAR-NK-92MI cell line was also analyzed by flow cytometry. Expression of CD147-CAR on NK-92MI was stable for more than 30 days post-transduction. However, CD147-CAR expression was associated with loss of CD147 on NK-92MI cell line, indicating the limiting fratricide among CD147-CAR-NK-92MI cells (FIGS. 2E-2G). Notably, the loss of CD147 molecule expression on CD147-CAR-NK-92MI cells did not affect their functionalities and expression in vitro.

Example 4

CD147-CAR NK Cells Specifically Kill Hepatocellular Carcinoma (HCC) In Vitro

Figures 3A, 3B:
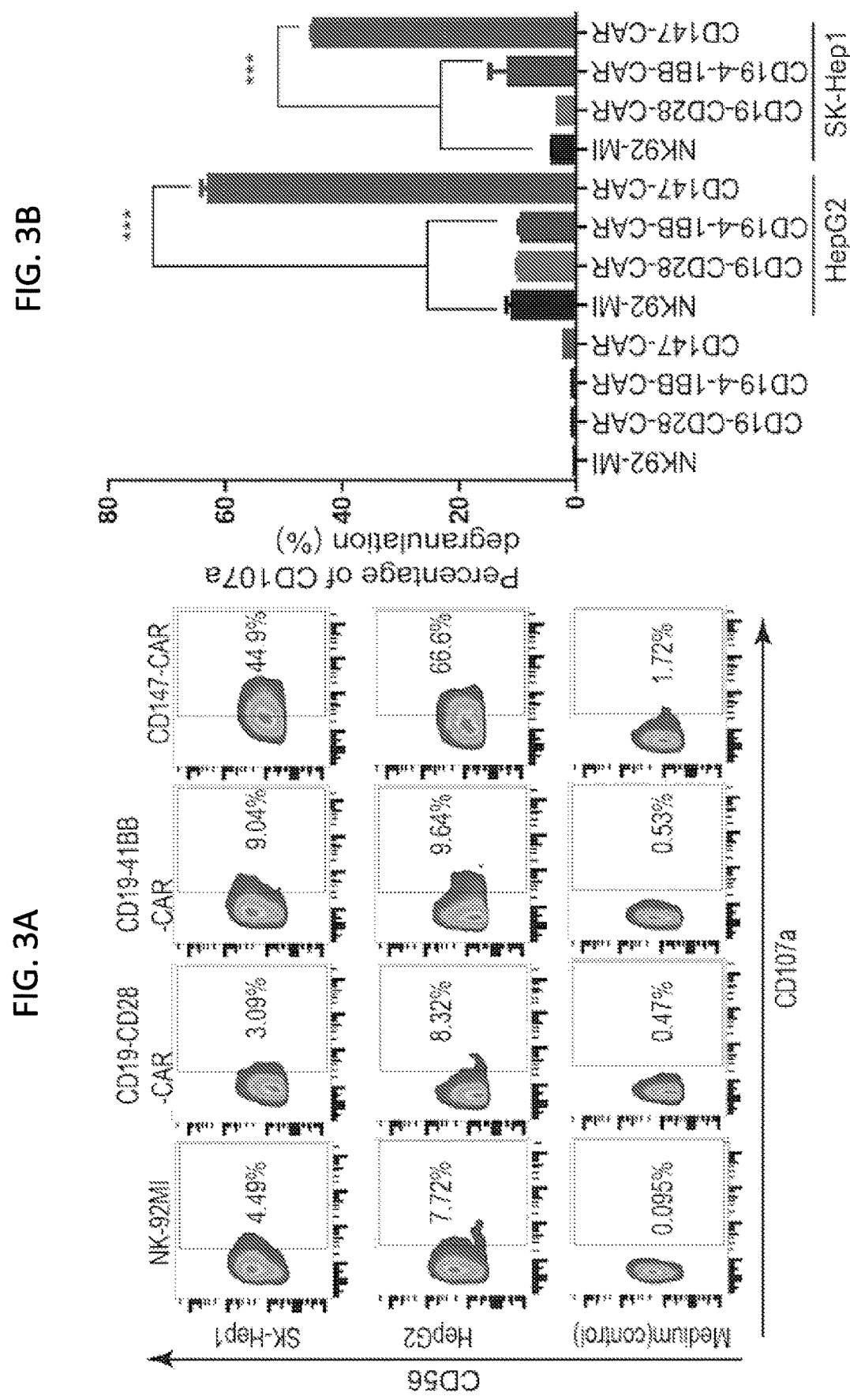
FIGS. 3A-3D show that CD107a degranulation and cytokine production in CD147-CAR-NK-92MI cells is stimulated with its sensitive target cells.
Figures 3C, 3D:
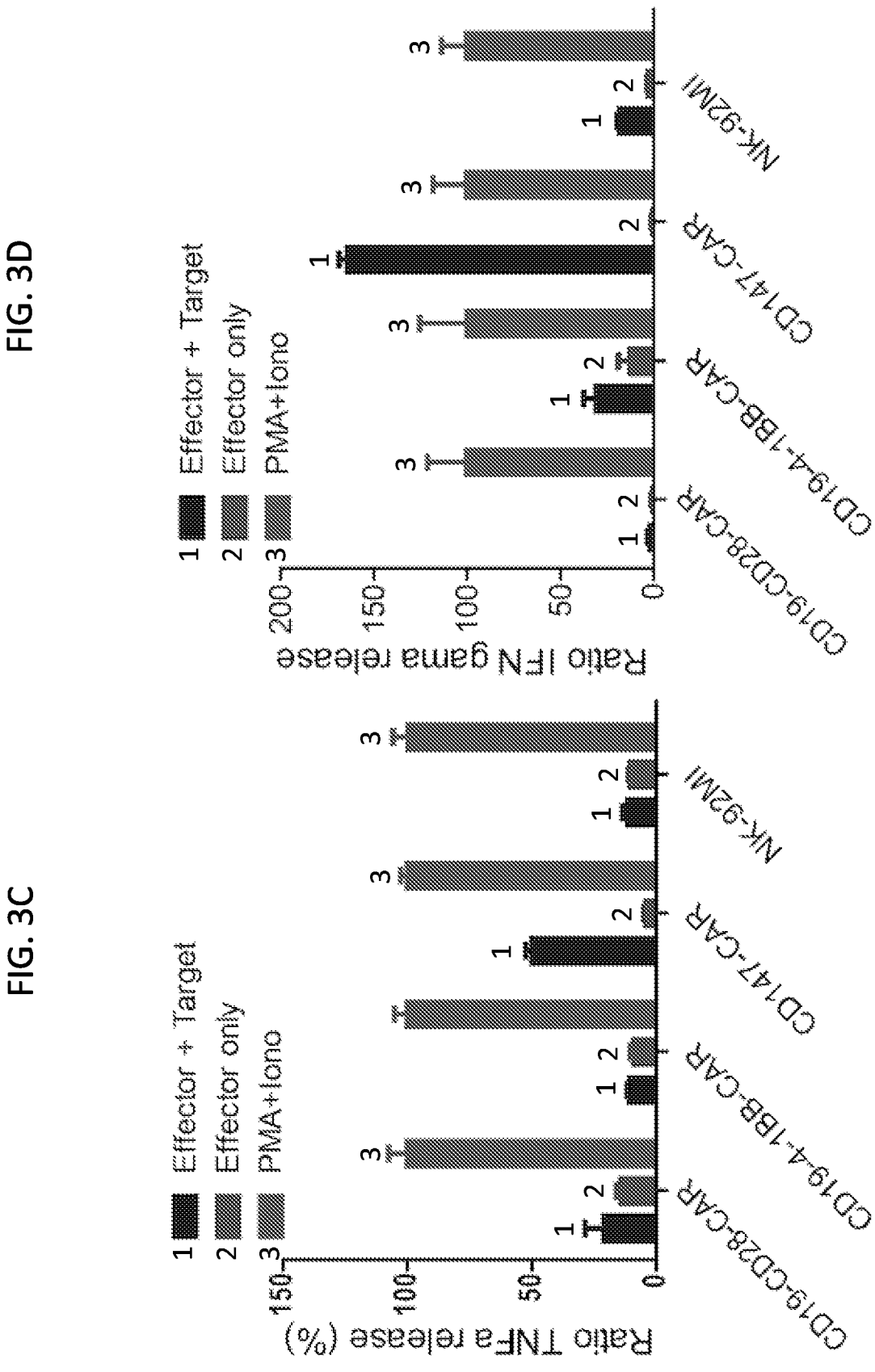
Figures 4A, 4B, 4C:
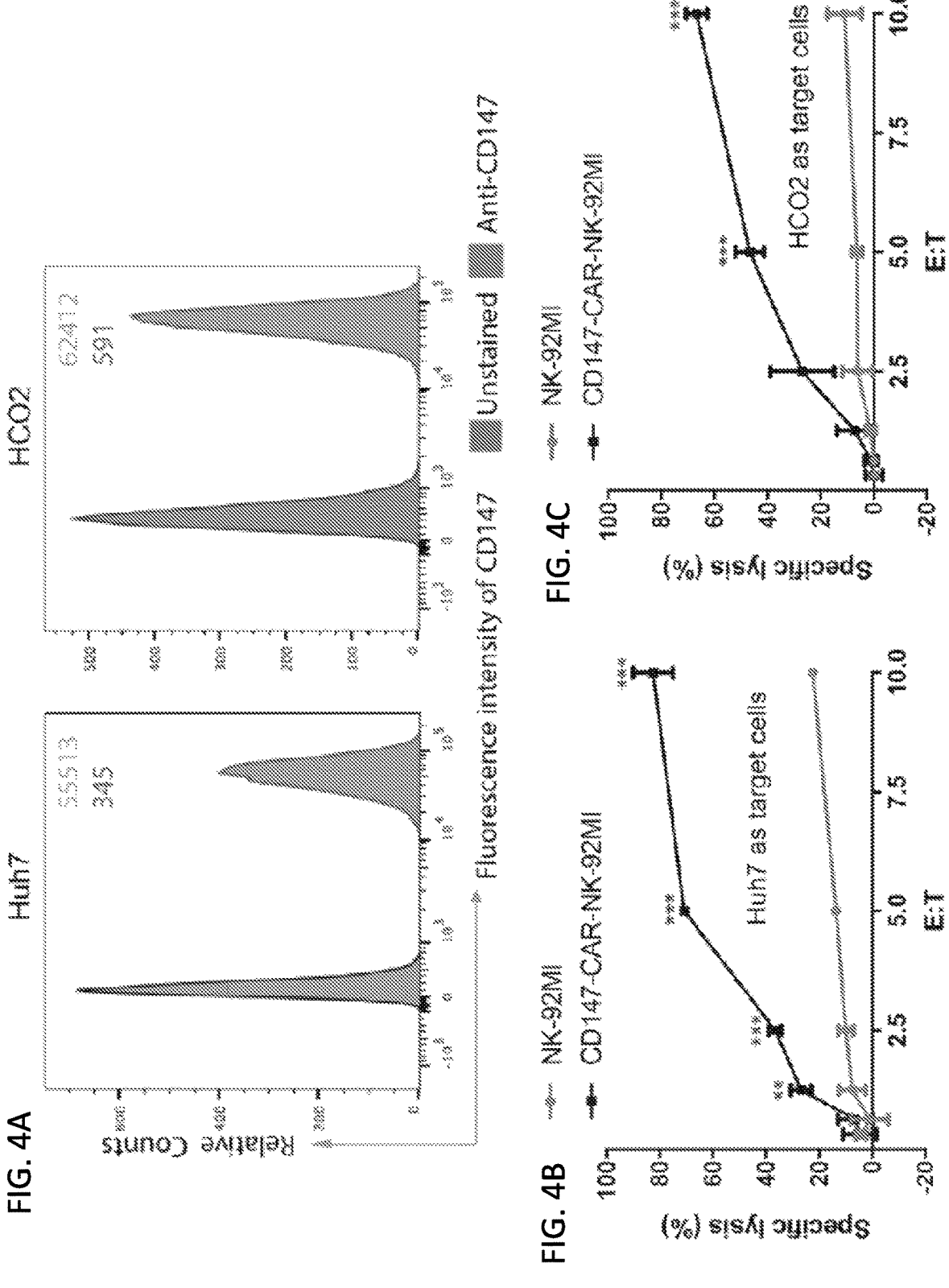
FIGS. 4A-4C show CD147-CAR-NK-92MI killing of two HCC cell lines.
Figures 5A, 5B, 5C:
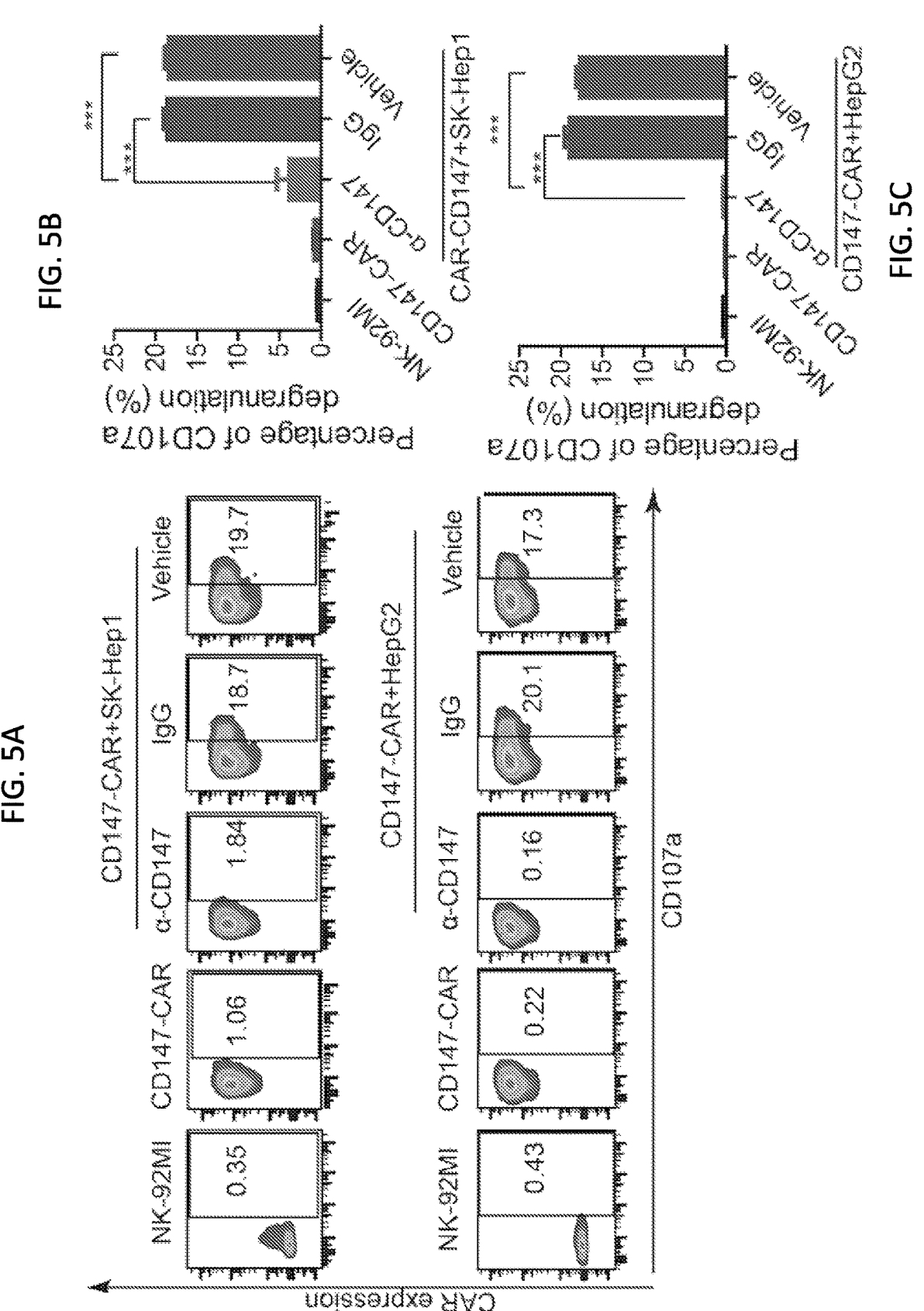
Figure 6:
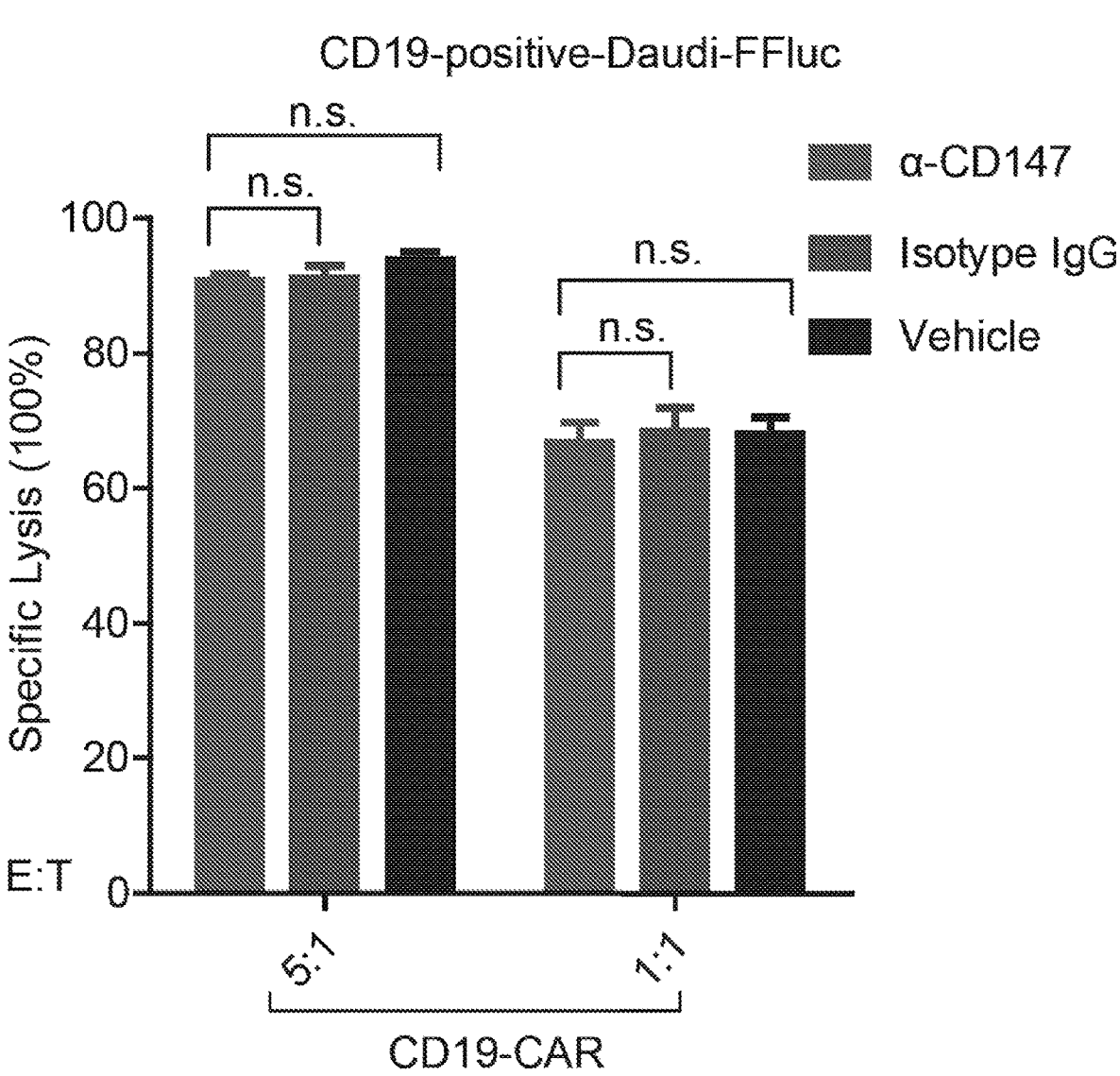
FIG. 6 shows that mouse-anti-human CD147 (HIM6) does not affect the cytotoxicity of CD19-CAR-NK cells. Cytotoxicity of CD19-CAR-NK-92MI was measured using the FFLuc report system assay. Briefly, Daudi-FFLuc cells (1×10$^4$) were pre-seeded in Matrigel (BD) treated 96-well optical-bottom microplate overnight. Effector cells (CD19-CAR-NK-92MI) at two different effector/target ratios (5:1 and 1:1, as indicated) were co-cultured for 6 hours. The luminescence signal was quantified by a microplate reader and the percentage of specific lysis was calculated. Data are pooled from three independent experiments. Error bars show±SEM (stand error of the mean). *p<0.05, p<0.01, and *p<0.001.

After successful establishment of CD147-CAR-NK cells, the capacity of CD147-CAR-NK-92MI cells to eradicate CD147+ HCC cell lines (including SK-Hep1 and HepG2 cells) was tested. Compared with control CD19-CD28-CAR-NK-92MI and CD19-4-1BB-CAR-NK-92MI cells, CD147-CAR-NK-92MI cells demonstrated significant cytotoxicity against two HCC cell lines, SK-Hep1 and HepG2 (FIGS. 3A and 3B), as well as Huh5 and HCO2 cell lines (FIG. 4A-4C). In addition, the production of both TNF-alpha and IFN-gamma by CD147-CAR-NK-92MI cells was significantly higher than that of CD19-CD28-CAR-NK-92MI and CD19-4-1BB-CAR-NK-92MI cells stimulated by SK-Hep1 and HepG2 cells (FIGS. 3C and 3D). Interestingly, activation of CD147-CAR-NK-92MI cells by their susceptible target cells can be blocked by the anti-CD147 antibody (clone HIM6), but not the control IgG1 (FIGS. 5A-5C). The specificity of this anti-CD147 antibody was further verified by testing its effects on cytotoxicity of CD19-4-1BB-CAR-NK-92MI cells. This anti-CD147 antibody could not block the cytotoxicity of CD19-4-1BB-CAR-NK-92MI cells against CD19-positive Daudi cell line (FIG. 6), indicating the selectivity of the CD19-4-1BB-CAR-NK-92MI cells and of the anti-CD147 antibody.

To further confirm the specificity of CD147-CAR-NK-92MI cells, the CD147-knockout (CD147$^{-/-}$) SK-Hep1 cell line (CD147$^{-/-}$-SK-Hep1) and CD147-knockout (CD147$^{-/-}$) HepG2 cell line (CD147$^{-/-}$ HepG2,) were generated. The CD147$^{-/-}$-HepG2 and CD147$^{-/-}$-SK-Hep1 cells were not recognized by CD147-CAR-NK-92MI cells (FIGS. 5D-5G), which was quantified by CD107a surface expression when co-cultured with CD147-KO cell lines.

Both CD107a assay and cytokine production assay can be used to evaluate the activation of CD147-CAR-NK-92MI cells by the susceptible target cells. To directly test whether CD147-CAR-NK-92MI cells can kill CD147-positive HCC cells, the 4-hour standard Chromium-51 ($^{51}$Cr) release assay (a gold standard assay for evaluating the cytotoxicity of CTLs and NK cells in the field of immunology) was used. The CD147-CAR-NK-92MI cells killed SK-Hep1 and Daudi cells. Similar killing activities by CD147-CAR-NK-92MI cells against additional HCC cell lines, such as the Huh7 cell line (Kasai et al., *Hum Cell* 31:261-267, 2018) and HCO2 cell line (Trinh et al., *PLOS One* 10:e0136673, 2015).

To further verify the killing activity of CD147-CAR-NK-92MI cells, a novel, easy-to-use, and non-radioactive approach for the assessment of CD147-CAR-NK-92MI cell cytotoxicity using a luciferase bioluminescent signal was developed. First, the FFLuc-EGFP-SK-Hep1 and FFLuc-EGFP-HepG2 cell lines were generated. To evaluate the direct killing of target cells, CD147-CAR-NK-92MI cells were co-cultured with FFLuc-EGFP-SK-Hep1 and FFLuc-EGFP-HepG2 cell lines, respectively. After a 4-hour incubation of CD147-CAR-NK-92MI cells in a 96-well optical-bottom microplate, which was pre-seeded with target cell stably expressing the EGFP-firefly luciferase fusion gene (EGFP-FFluc), the chemical bioluminescent signal of EGFP-FFluc was quantified by a fluorescent microplate reader. The FFLuc signal was converted into the percentage of specific lysis, as described in the Example 1, similar to the $^{51}$Cr release assay (FIGS. 8H and 8I).

Figures 8A, 8B, 8C, 8D, 8E, 8F, 8G, 8H, 8I:
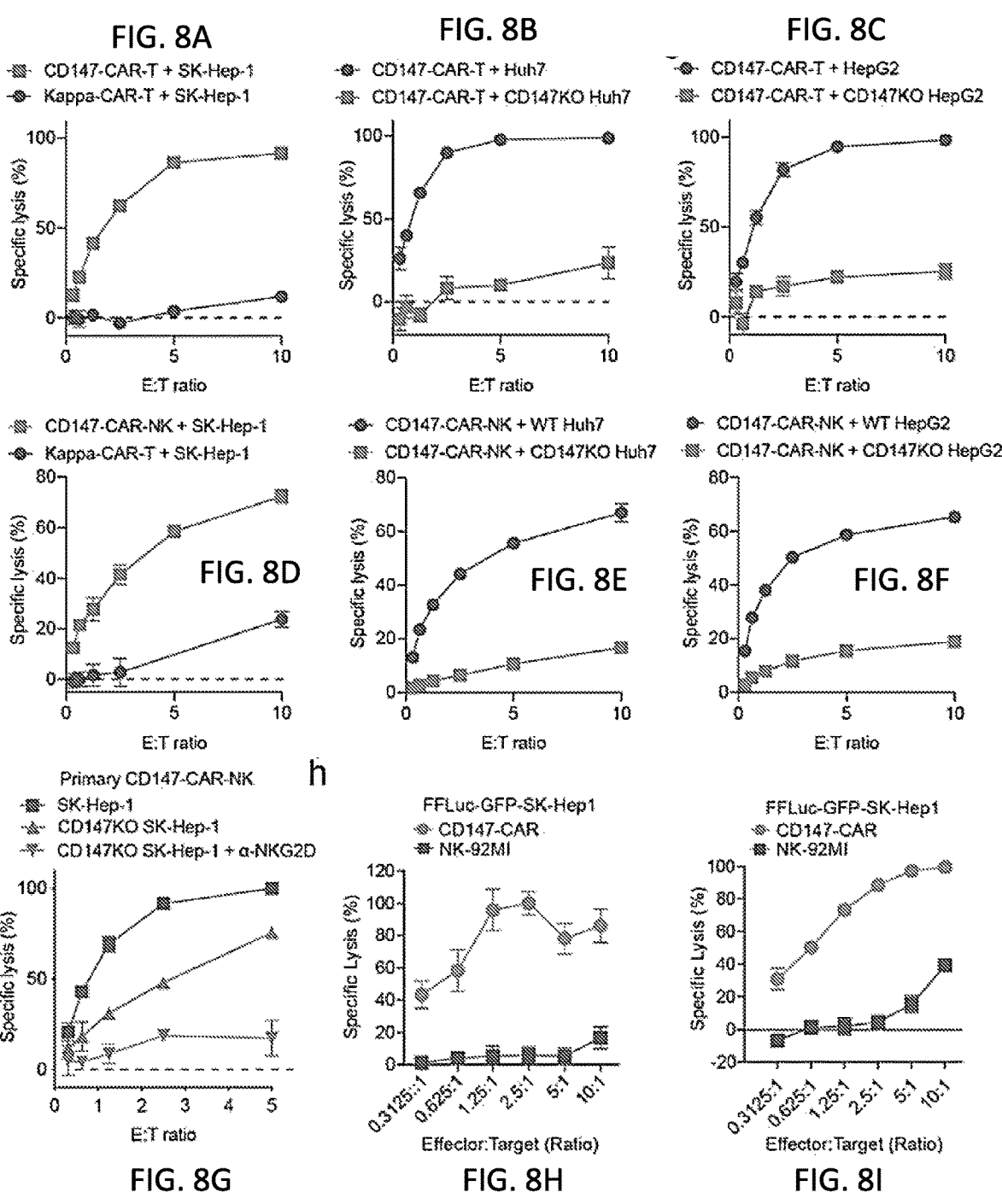
Figure 9A:
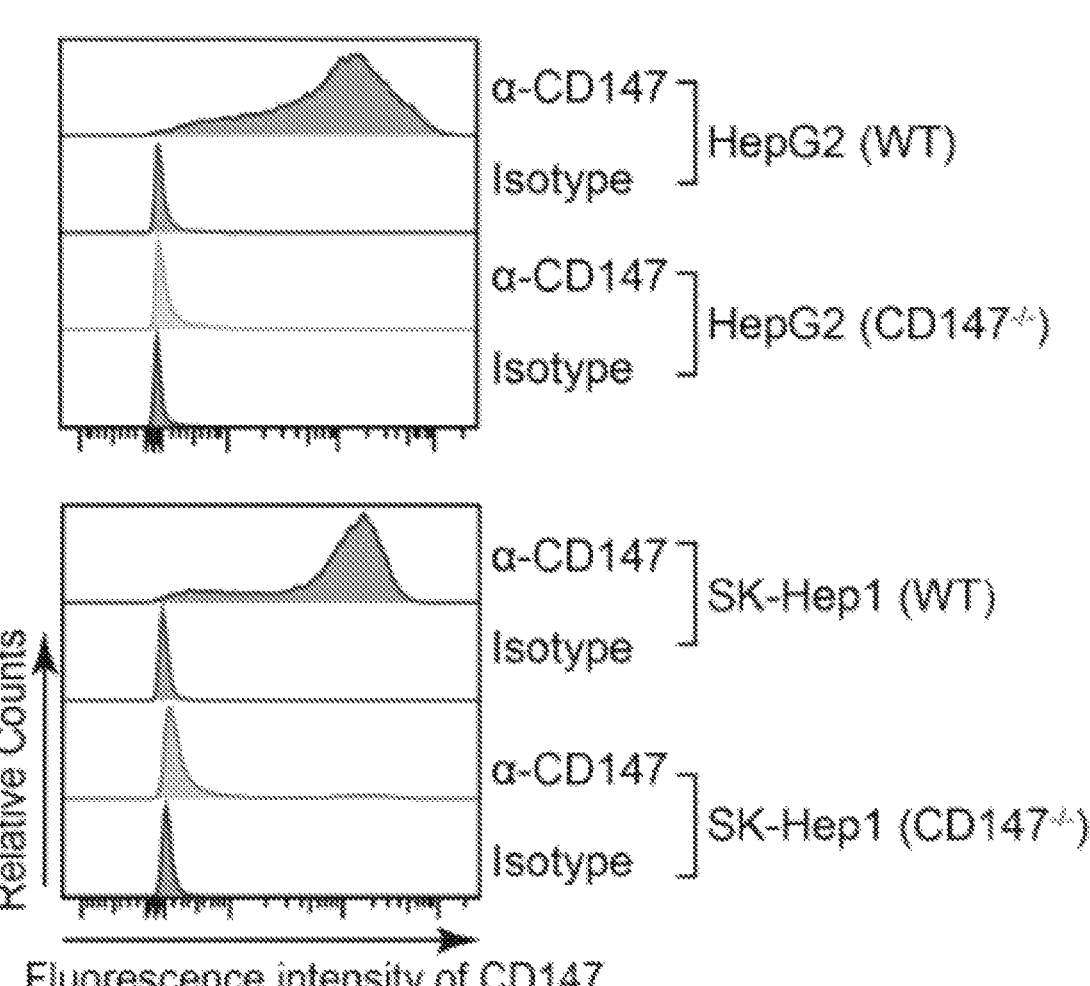
FIGS. 9A and 9B show verification of knockout-CD147 SK-Hep1 and HepG2 cell lines by flow cytometry and western-blot.
Figure 9B:
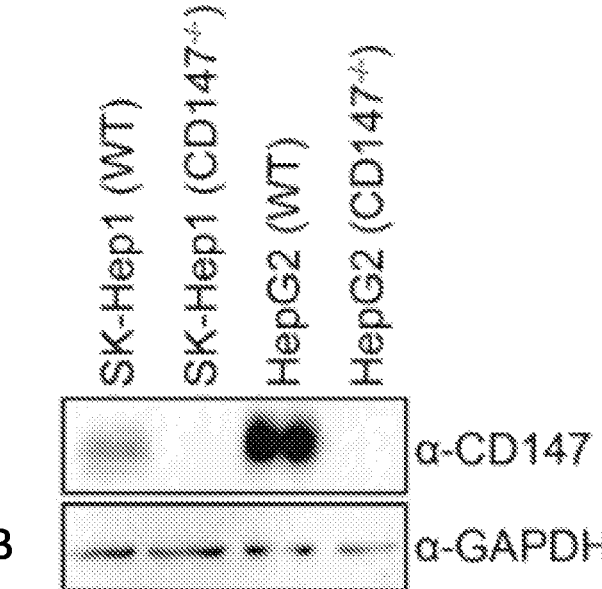
Figures 11A, 11B, 11C, 11D:
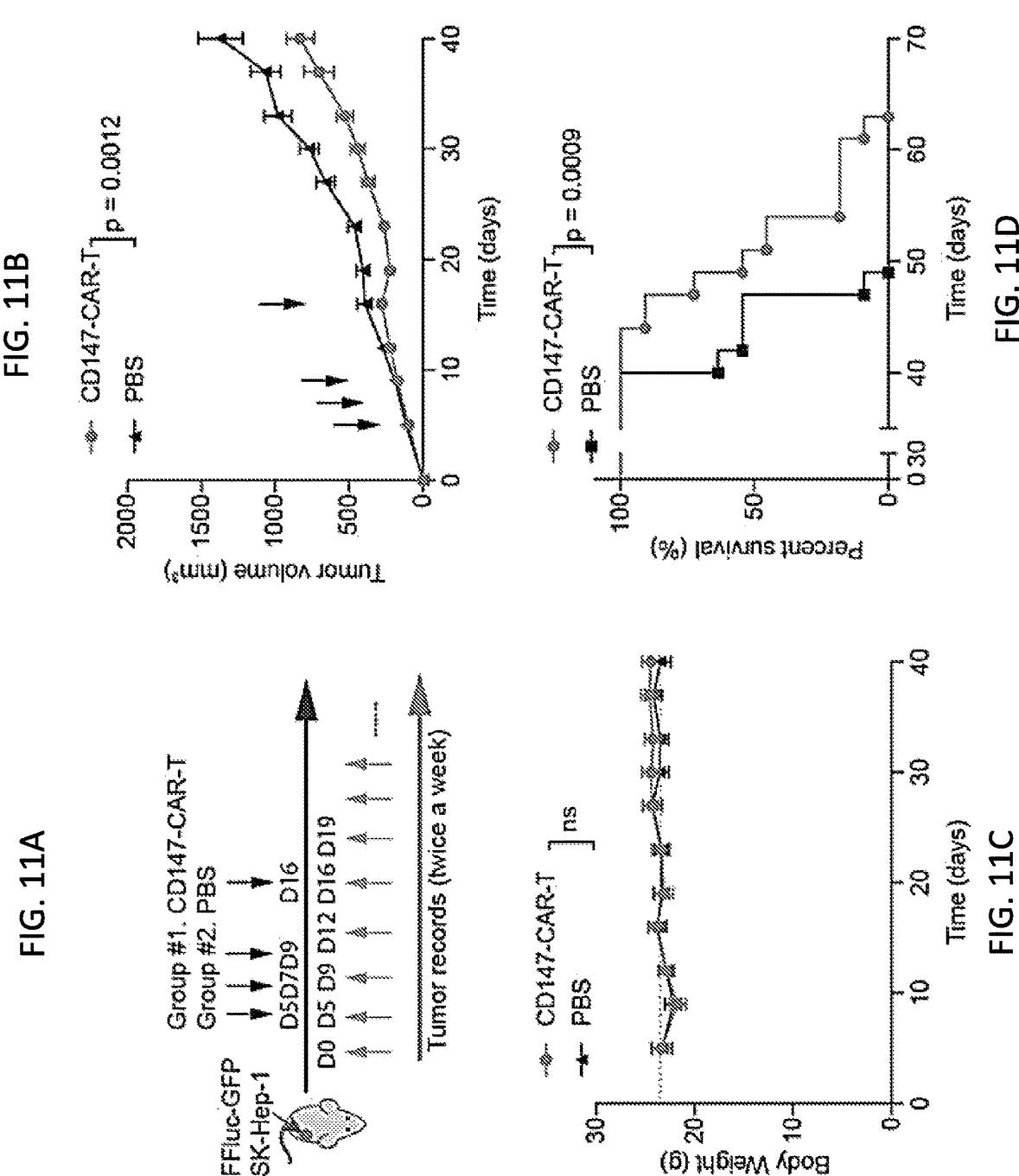
FIGS. 11A-11D show that CD147-CAR-T-92MI cells control progression of HCC in a xenograft mouse model.
Figures 14A, 14B, 14C, 14D:
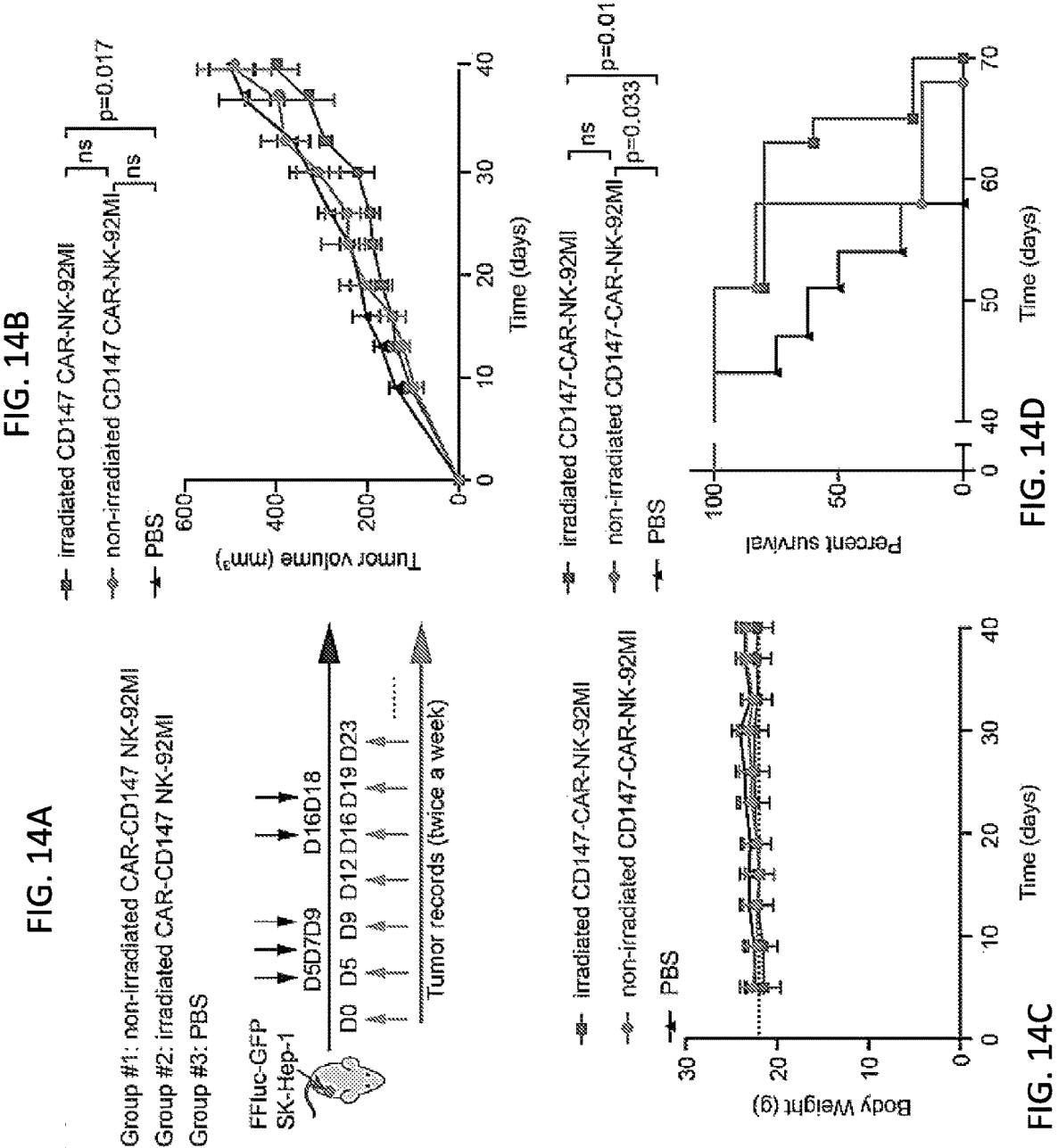
FIGS. 14A-14D show comparable anti-HCC tumor activity between irradiated CD147-CAR-NK-92MI and non-irradiated CD147-CAR-NK-92MI cells in control of HCC progression in xenograft mouse model.

At first, CD147-CAR modified primary T and NK cells isolated from human peripheral blood mononuclear cells (PBMCs) can eradicate multiple HCC cell lines (including SK-Hep1, Huh7, and HepG2, etc.), but not kappa-CAR modified T cells (FIGS. 8A-8C). We also demonstrated that CD147-CAR modified human primary NK cells effectively killed HCC cell lines, in vitro, by $^{51}$Cr release assay (FIGS. 8D-8F). To further demonstrate primary NK naturally killing ability through the NKGD/NKG2DL interaction in addition to CD147-CAR-primary NK cytotoxicity, we found anti-NKG2D further blocked the killing of CD147$^{-/-}$-SK-Hep1 cells by CD147-CAR-NK (FIG. 8G).

Figures 7A, 7B:
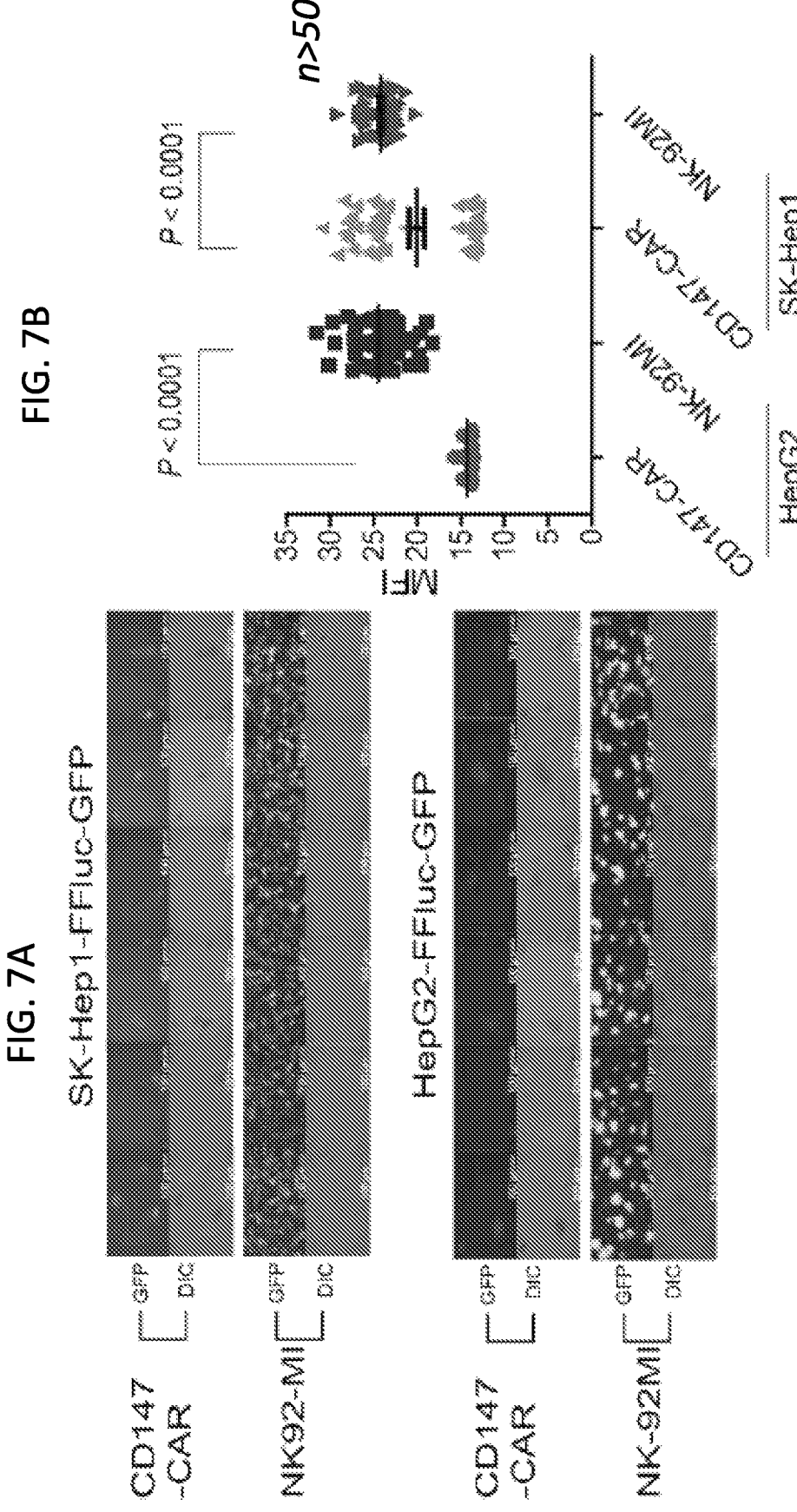
FIGS. 7A and 7B show representative images of CD147-CAR-NK-92MI killing activities. Effector cells (1×10$^4$) CD147-CAR-NK-92MI and NK-92MI were co-cultured for 12 hours with target cells FFLuc-GFP-SK-Hep1 (FIG. 7A, top) (1×10$^4$) and FFLuc-GFP-HepG2 (FIG. 7A, bottom) in a 96-well optical-bottom microplate. Conventional fluorescent microscopy detected GFP fluorescence (top lane) and brightfield (bottom lane) was used to visualize CD147-CAR-NK-92MI killing activities at the same setting. The GFP fluorescence intensity was quantified by ImageJ software (NIH) (FIG. 7B). Quantitative mean fluorescence intensity (MFI) of GFP was plotted by Graph prism 5 software (GraphPad Software, San Diego, CA, USA).

The dose-dependent specific lysis was comparable with $^{51}$Cr release assays. The cytotoxicity activity measured by this approach was further quantified under a common inverted fluorescence microscope to evaluate the morphology and dynamics of EGFP signal in target cells (FIGS. 7A and 7B). Therefore, two complementary approaches demonstrated that CD147-CAR NK cells specifically kill hepatocellular carcinoma (HCC) in vitro.

CD147-CAR-NK-92MI cells could not kill the CD147$^{-/-}$-SK-Hep1 and CD147$^{-/-}$-HepG2, compared to parental SK-Hep1 and HepG2 cells (FIGS. 8K and 8L). The specificity of CD147-CAR-NK-92MI cell cytotoxicity was further verified by adding anti-CD147 antibodies in the effector and target cell co-culture system (FIGS. 8M and 8N). To further validate CD147 as an effective and valid target for HCC, the cytotoxicity of CD147-CAR-T cells against two different HCC cell lines-HepG2 (FIG. 10A) and SK-Hep1 (FIG. 10B) was tested. When CD147 molecules were deleted in SK-Hep1 cell line (CD147-knockout SK-Hep1 cell line), the specific lysis of CD147-CAR-T cells had significantly decreased (FIG. 10C), which further validated the specificity cytotoxicity of CD147-CAR-T cells against CD147 positive HCC cell lines.

Example 5

CD147-CAR-NK Cells Control Progression of HCC In Vivo

To evaluate whether CD147-CAR can kill HCC, in vivo, two different xenograft models were used. First, CD147-CAR-modified primary T and NK cells derived from PBMCs were evaluated in a SK-Hep1 xenograft mouse model. CD147-CAR-modified primary T cells significantly suppressed tumor size and prolonged survival (FIGS. 11A-11D). To further evaluate the efficacy of CD147-CAR modified primary NK cells, we included a non-transduced (NT) primary NK group as an additional control (FIGS. 12A-12D). Mice receiving parental NT-NK control group and PBS vehicle control group developed rapid disease progression. In contrast, mice receiving CD147-CAR-primary T and NK cells were significantly protected from rapid progression and their median survival was prolonged (P<0.05), with comparable body weights among the different groups (FIGS. 11C and 12C), indicating the tolerable toxicity of CD147-CAR-modified primary T and NK cells, in vivo.

Figure 13:
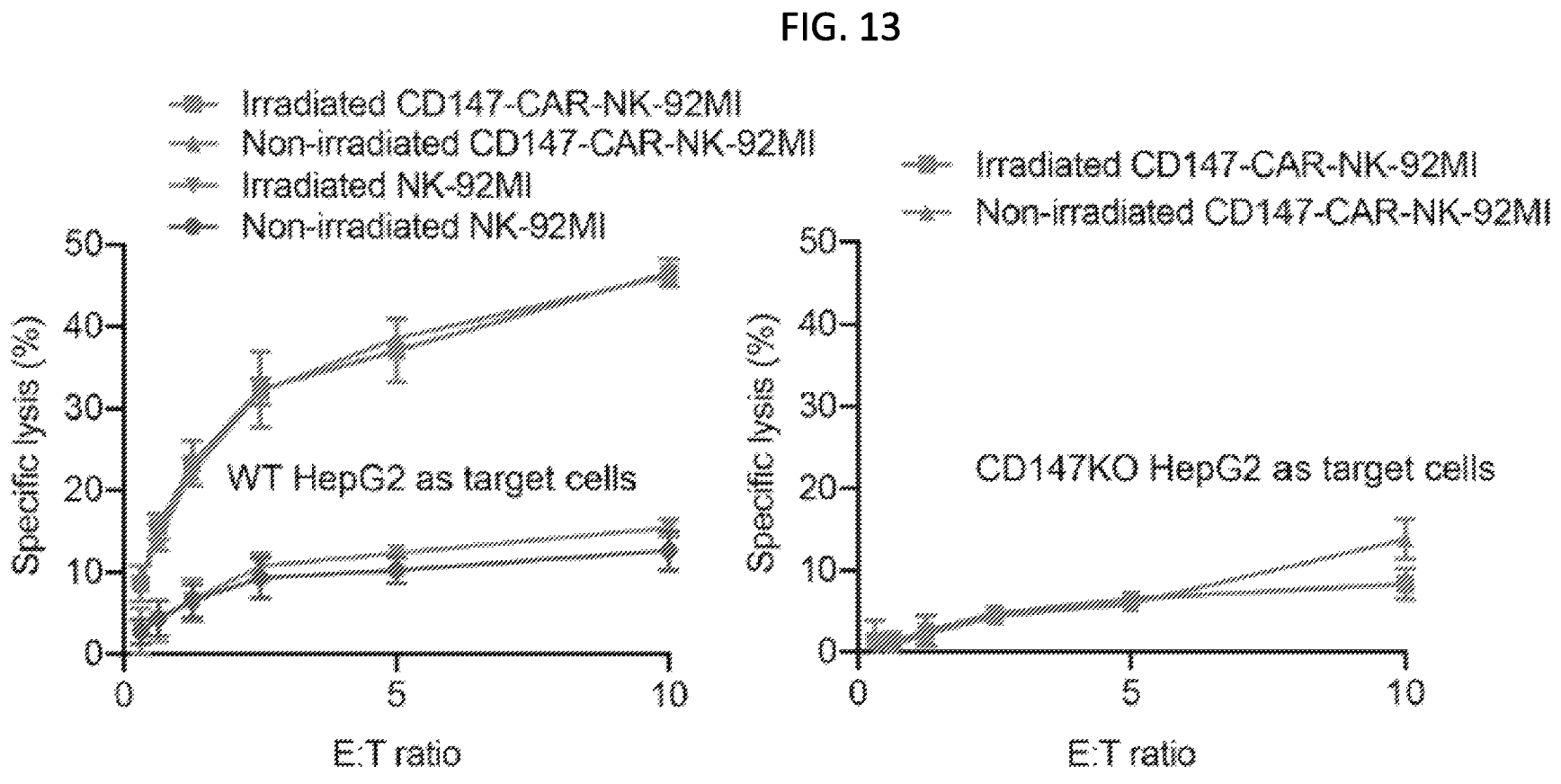

Furthermore, to further develop additional 'off-the-shelf' cell therapy strategies, we evaluated the efficacy of CD147-CAR modified NK-92MI cells. Due to the malignant nature of NK-92MI, CAR-modified NK-92MI cells need to be irradiated before administered to patients 46,61. The cytotoxicity of non-irradiated and irradiated CD147-CAR-NK-92MI cells were compared by standard 4-hour $^{51}$Cr release assays (FIG. 13). Comparable cytotoxicity between non-irradiated and irradiated CD147-CAR-NK-92MI cells was observed, in vitro (FIG. 13).

The efficacies between non-irradiated and irradiated CD147-CAR-NK-92MI cells in the xenograft NSG mouse model were further compared (FIGS. 14A-14D). Comparable efficacies, in vivo, measured by median survival, between non-irradiated and irradiated CD147-CAR-NK-92MI-infused mice were observed (FIGS. 14A-14D).

Figures 15A, 15B, 15C, 15D:
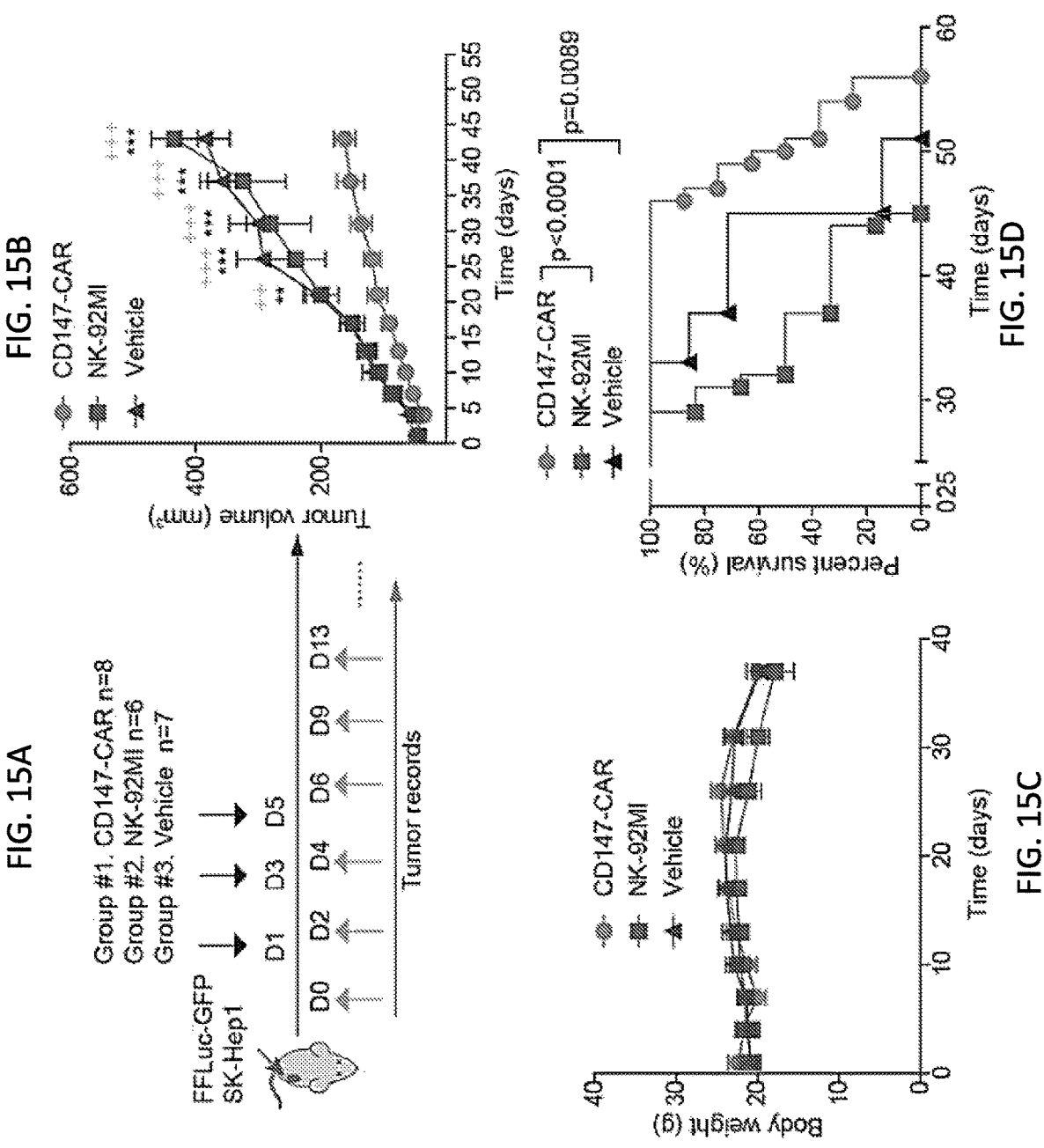
FIGS. 15A-15D show that CD147-CAR-NK-92MI cells control progression of HCC in a xenograft mouse model.

To further evaluate the efficacy of CD147-CAR-NK-92MI cells (injected on day 1, day 3, and day 5 after tumor implantation) to control tumor growth, disease progression was measured by tumor size (FIG. 15A). Mice receiving parental NK-92MI and PBS vehicle control groups developed rapid disease progression (FIG. 15B). In contrast, mice receiving CD147-CAR-NK-92MI cells were significantly protected from rapid progression and their median survival was prolonged (P<0.01), with comparable body weights among the different groups (FIGS. 15C and 15D), indicating the tolerable toxicity of CD147-CAR-NK-92MI cells, in vivo.

Figures 16A, 16B, 16C, 16D:
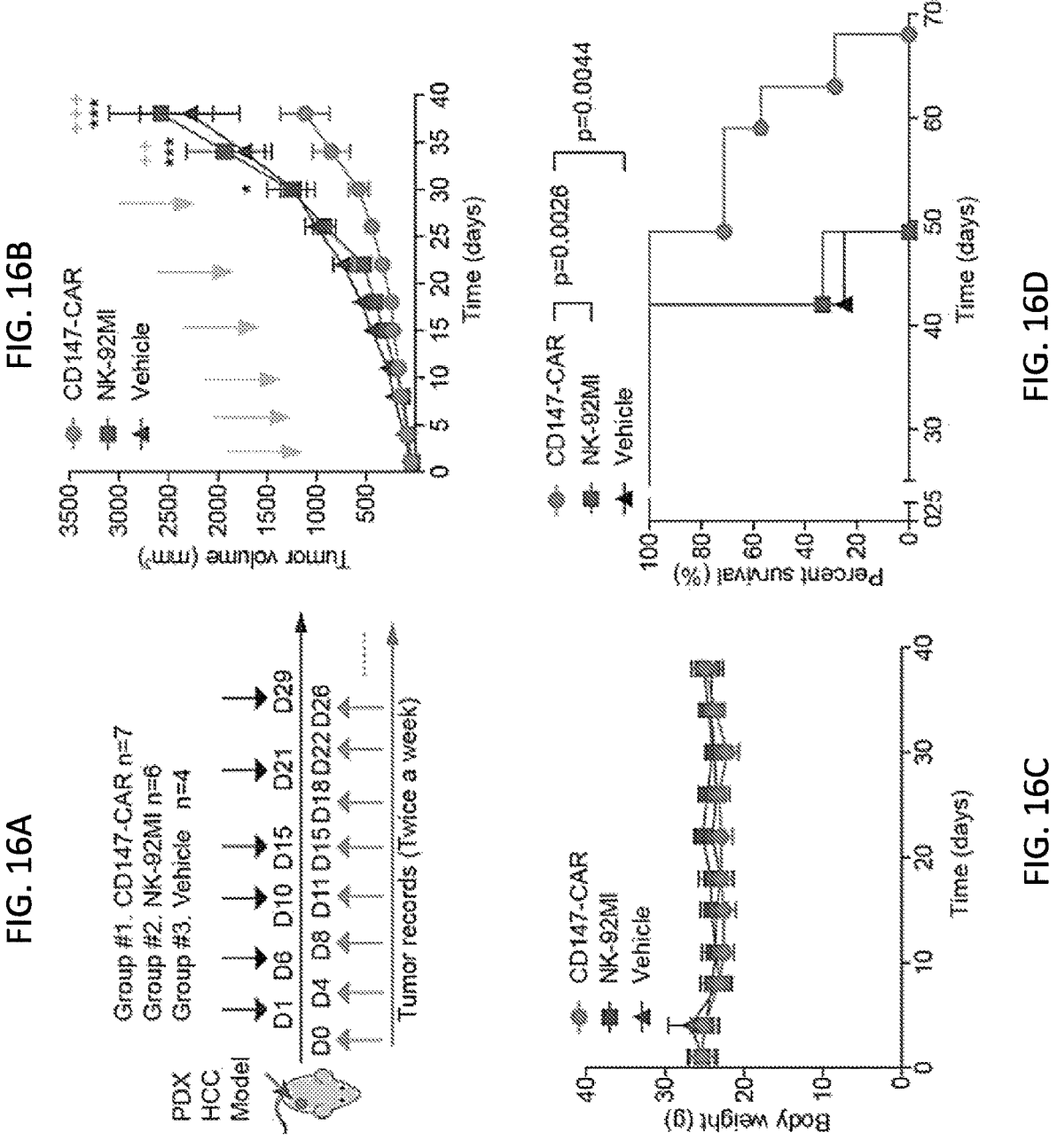
FIGS. 16A-16D show that CD147-CAR-NK-92MI cells control progression of HCC in a PDX mouse model.

Although cancer cell lines may have significant limitations in their ability to precisely model biology and therapeutic effects, patient-derived xenografts (PDXs) models are biologically stable and can mimic human clinic conditions regarding mutational status, gene expression patterns, and tumor heterogeneity. Thus, a second xenograft mouse model was employed, using metastatic liver cancer tissue from a patient. The effect of CD147-CAR-NK-92MI cells administered on day 0, day 4, day 8, day 11, day 15, day 22, day 25, and day 35 after engraftment was tested. The median survival of mice treated with CD147-CAR-NK-92MI cells was 63 days, which was significantly higher than that of control mice (median survival about 42 days). Reduced tumor burden and disease progression were observed in the mice treated with CD147-CAR-NK-92MI cells (FIGS. 16A-

16D), indicating the effectiveness of CD147-CAR-NK-92MI cells in suppressing liver cancer progression in a PDX mouse model.

Example 6

CD147-CAR-T Cells Specifically Kill CD147-Positive Tumor Cells

The ability of CD147-CAR-T cells to kill HCC cells was tested against 8 HCC cell lines (Huh7, Huh7.5, HepG2, SK-Hep1, Hep3B, Hu1545, HCO2, and LH86). Peripheral blood mononuclear cells (PBMCs) were obtained from healthy donors. To transduce the PBMCs, cells were activated with 1 µg/ml anti-CD3 (clone, OKT3, Ortho Biotech, Bridgewater, NJ, USA) and 1 µg/ml anti-CD28 with 100 U/ml recombinant human IL-2 (Proleukin; Chiron, Emeryville, CA, USA) in 10% FBS RPMI-1640 media. To produce CD147-CAR-T cells, activated T cells were transduced with retroviral supernatants on day 3 in plates coated with recombinant fibronectin fragment (FN CH-296; Retronectin; Takara Shuzo, Otsu, Japan). After transduction, T cells were expanded using IL-2 and then used for assays.

FFLuc reporter system assay as described in Example 1 was used to test for specific killing of FFLuc-EGFP-HepG2 by CD147-CAR-T cells (FIG. 17A). Effector cells (CD147-CAR-T cells) were co-cultured with target cells at $1 \times 10^4$ per well FFLuc-GFP-HepG2 in a 96-well optical-bottom microplate for 6 hours. The control group used the wild type kappa-CAR-T cells incubating with CD147-positive FFLuc-EGFP-HepG2. Decreased cytotoxicity of CD147-CAR-T cells using knockout-CD147 FFLuc-GFP-HepG1 was shown by FFLuc report system assay (FIG. 17B). Effector cells (CD147-CAR-T and Kapp-CAR-T cells) were co-cultured with target cells CD147-positive FFLuc-EGFP-HepG2 ($1 \times 10^4$) in a 96-well optical-bottom microplate for 6 hours. Cytotoxicity of CD147-CAR-T cells was measured by the luminescent signal read by microplate reader. Cytotoxicity of CD147-CAR-T cells was measured by a standard 4-hr $^{51}$Cr release assay (FIG. 17C). Kappa-CAR-T cells were used as a negative control group.

Example 7

Effect of CD147-CAR-T Cells on Neuroblastoma Cells

Figure 18A:
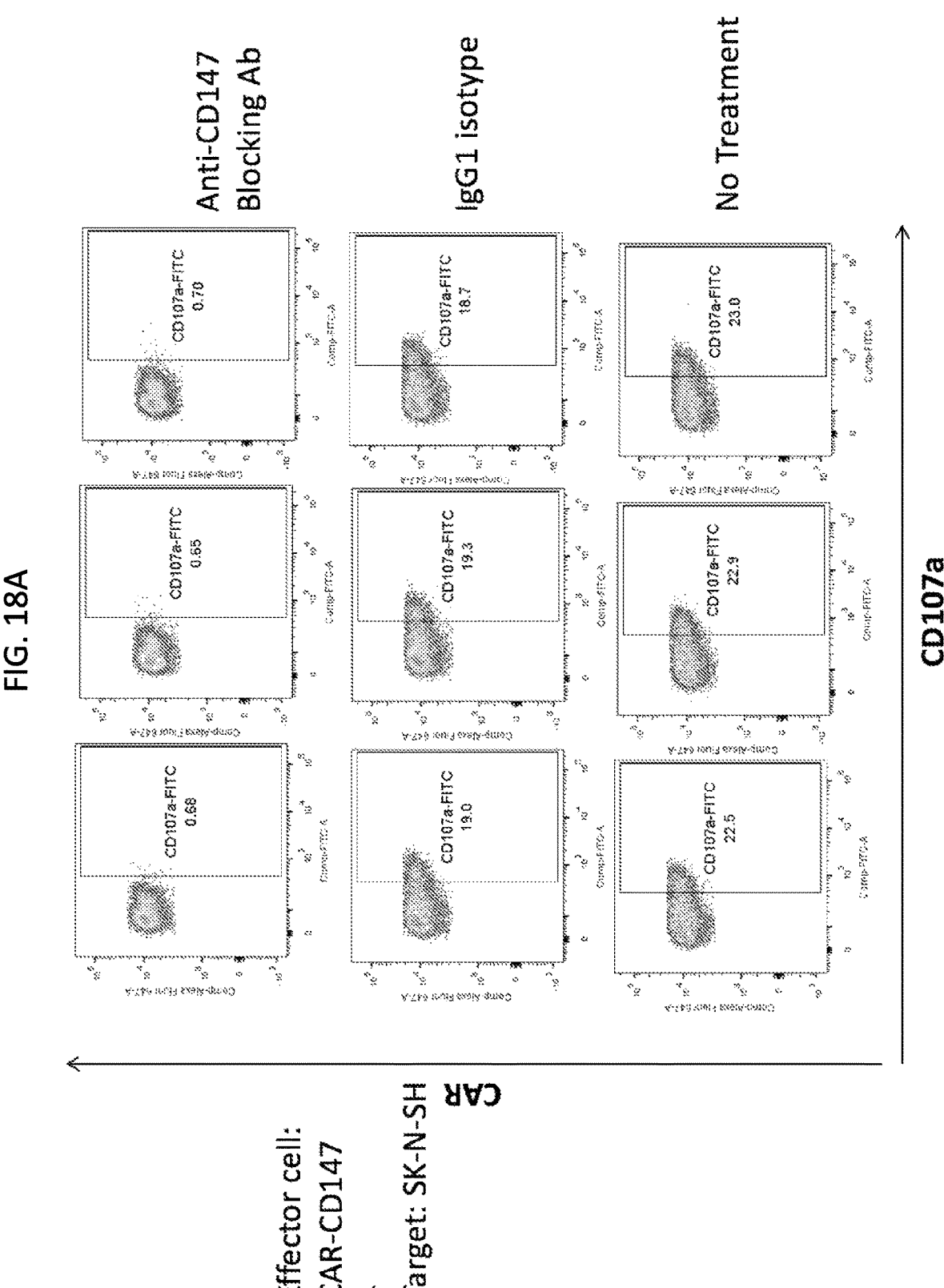
FIGS. 18A and 18B show CD107a degranulation by CD147 CAR-T or -NK cells.
Figure 18B:
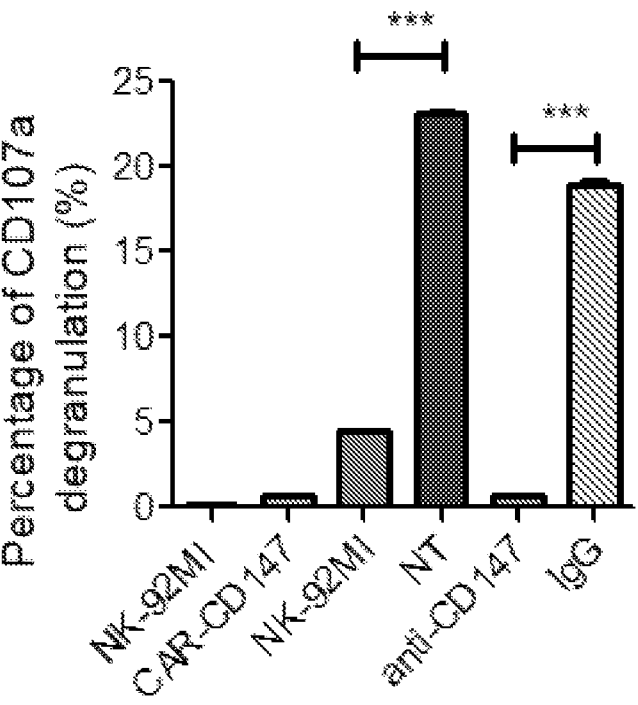
Figure 19:
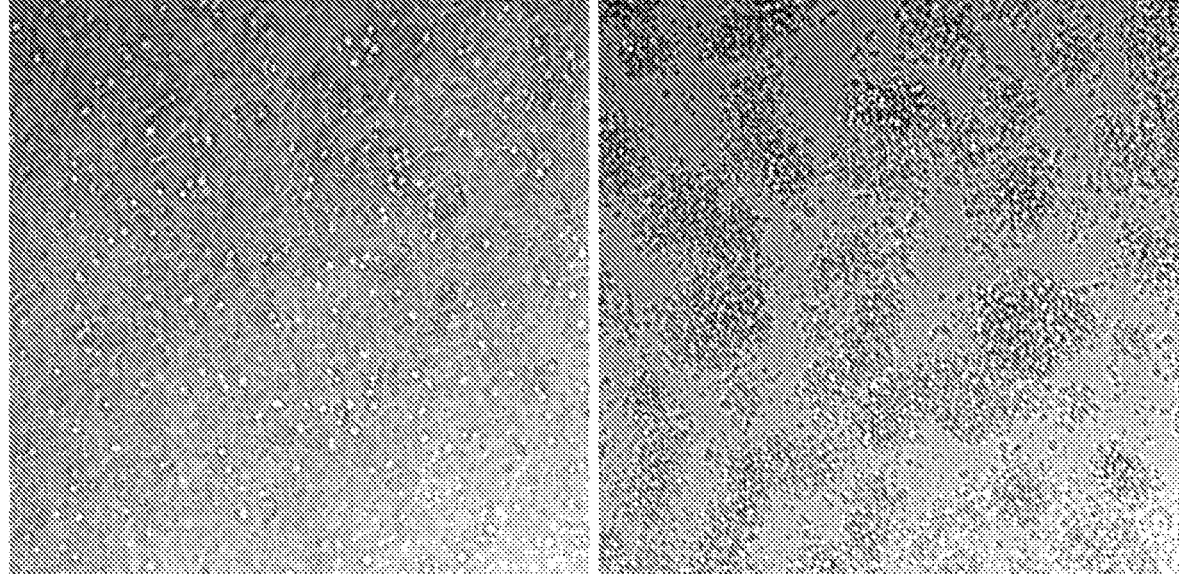
FIG. 19 shows cytotoxicity of CD147-CAR-NK-92MI cells to DaoY cells in vitro.

CD107a degranulation on CD147-CAR-T cells was observed after 10 hours with medium (control) or SK—N—SH tumor cells (FIG. 18A), as well as DaoY and D283 cells. The ratio of effector and target was 1:1.2. Cells were gated for CD56 positive subsets for quantifying surface CD107a expression. Quantitative data for percentage of surface CD107a expression on CD147-CAR-NK-92MI cells upon different stimulations, as indicated (FIG. 18B). CD147-CAR-NK-92MI cells were also cytotoxic to DaoY cells after 3 hours (FIG. 19).

Example 8

Figures 21A, 21B, 21C:
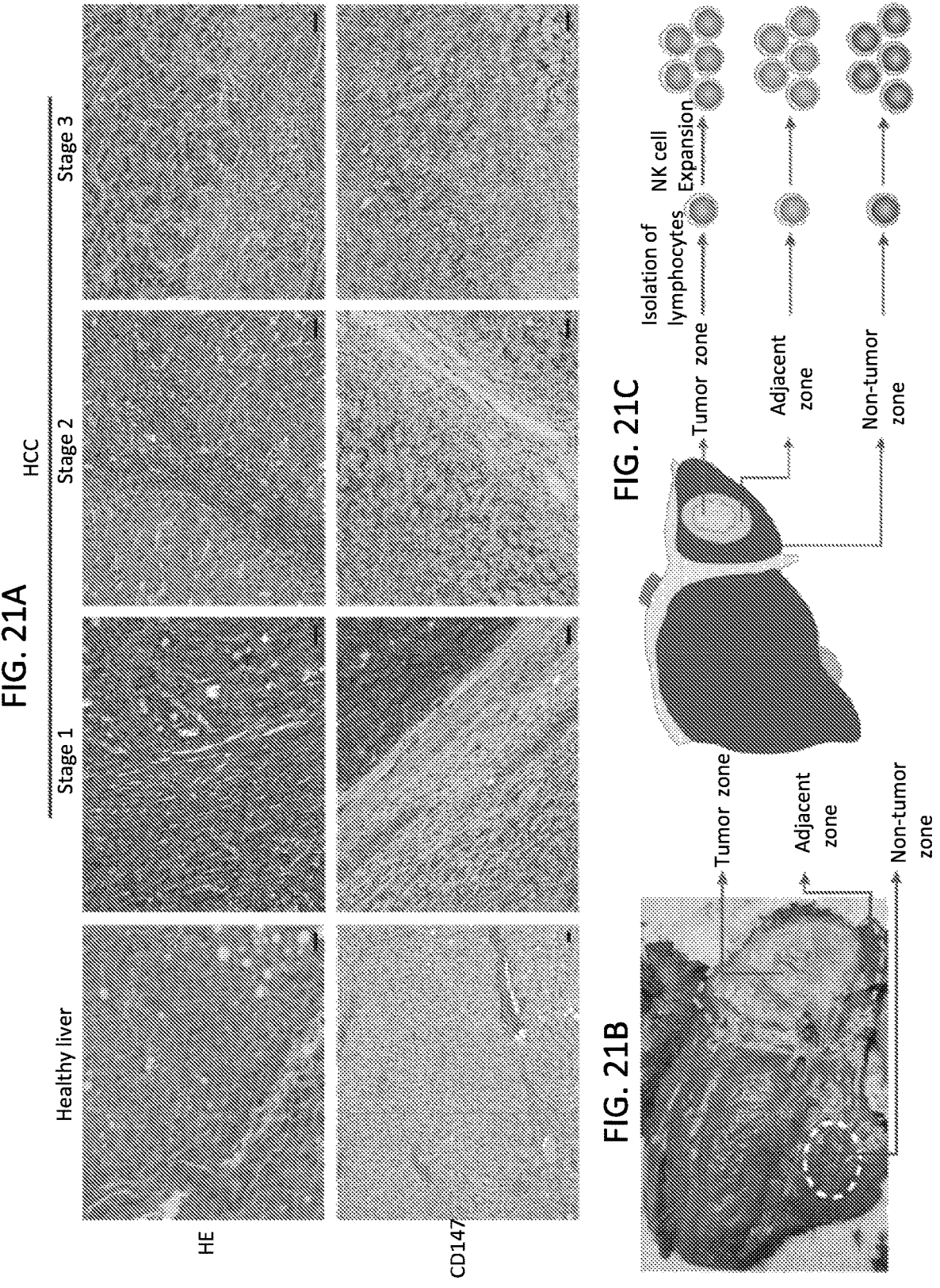
FIGS. 21A-21E show patient derived primary CD147-CAR-NK cells specifically kill CD147-positive tumor cells in vitro.

HCC Patient-Derived Primary CD147-CAR-NK Cells Specifically Kill CD147-Positive Tumor Cells In Vitro Due to CD147's broad expression pattern across multiple solid tumor types, CD147 is an attractive target for CD147-CAR-based cancer immunotherapy. Here, we examined whether CD147 is upregulated in human HCC tissue samples. Different stages of HCC tumor tissue stained strongly positive for CD147, compared to healthy liver tissue (FIG. 21A).

Figure 21D:
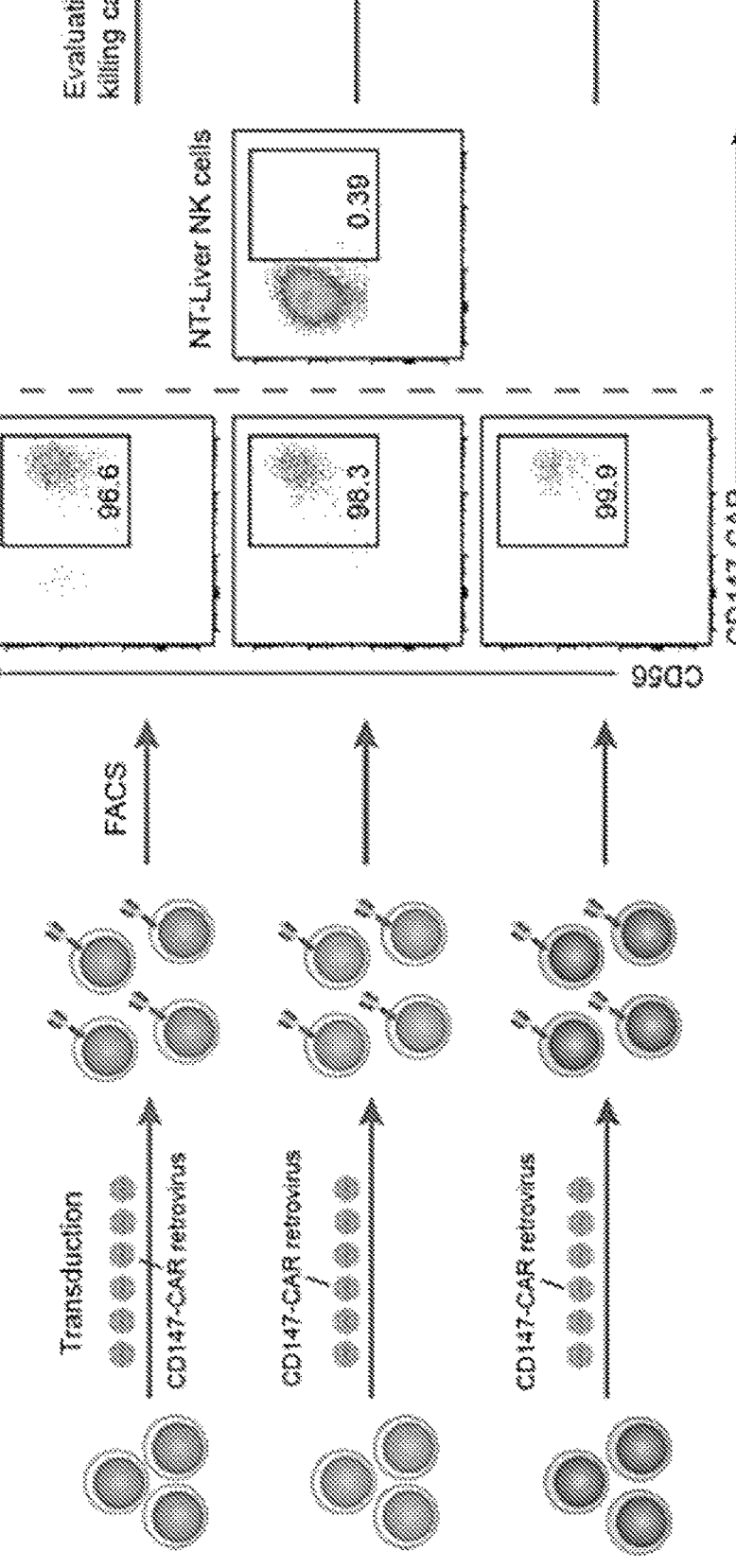
Figure 21E:
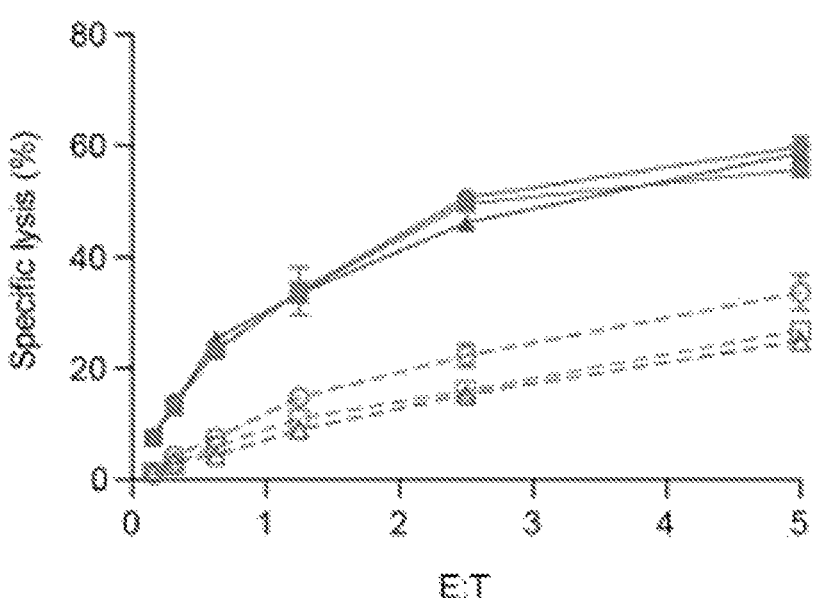

To evaluate whether CD147-CAR modified primary NK cells directly isolated from HCC liver can kill HCC, in vitro, NK cells were isolated from different zones of liver tissue (FIG. 21B), which includes a tumor zone, tumor adjacent zone, and a non-tumor zone in a human liver with HCC. Then, these NK cells were expanded (FIG. 21C). CD147-CAR were generated using these expanded NK cells from human HCC liver tissue. The transduction efficiency of activated NK cells was generally greater than 70% (FIG. 21D). CD147-CAR-NK cells specifically recognized tumor cells expressing CD147. The anti-tumor activity of CD147-CAR-NK was evaluated against HCC cell lines (FIG. 21E). Together, this demonstrates that CD147-CAR-redirected primary human liver NK cells kill the CD147-positive target cells specifically and selectively.

Example 9

SynNotch GPC3-Inducible CD147-CAR T Cells Selectively Target GPC3+CD147+ HCC Cells, but not GPC3+CD147− or GCP3-CD147+ HCC Cells To generate an anti-GPC3 synNotch induced receptor vector, anti-GPC3 (mouse GC33 clone) scFv that can specifically bind with human GPC3 antigen was synthesized by GENEWIZ. The sequence encoding a signal peptide and a myc-tag at the N-terminal were fused with the synNotch-Gal4VP64 induced element derived from (Addgene plasmid #79125) by overlap PCR. The fragments were inserted into the SFG gamma retrovirus vector which were digested by restriction endonucleases NcoI and XhoI.

For construction of the anti-CD147-CAR-mCherry vector, the entire CD147-CAR element was inserted into pHR_Gal4UAS_pGK_mCherry (Addgene plasmids #79124) which was digested by restriction endonucleases MluI and NdeI. The expression of the mCherry gene was under control of the pGK promoter. In this strategy, eGFP and mCherry double positive cells were gated as synNotch CAR modified cells for further analysis and functional evaluation.

To generate the anti-CD147 synNotch induced receptor vector, anti-CD147 scFv was fused with the synNotch-Gal4VP64 induced element derived from pHR_PGK_antiCD19_synNotch_Gal4VP64 (Addgene plasmid #79125) by overlap PCR. A myc-tag was added to the N-terminal. The fragments were inserted into the SFG gamma retrovirus vector after the signal peptide, which were digested by restriction endonucleases SalI and MluI.

For construction of the anti-GPC3-CAR-mCherry vector, the entire GPC3-CAR element, which contains anti-GPC3 (mouse GC33 clone) scFv, was inserted into pHR_Gal4UAS_pGK_mCherry (Addgene plasmids #79124) which was digested by restriction endonucleases MluI and NdeI. Expression of the mCherry gene was under control of the pGK promoter. In this strategy, myc-tagged and mCherry double positive cells were gated as synNotch CAR modified cells for further analysis and functional evaluation.

TABLE 2

Primers for plasmid construction

| Construct name | Primer name | Primer sequence | SEQ ID NO: |
|---|---|---|---|
| pSFG-Myc-αCD147-synNotch-Gal4VP64 | SFG-Myc-CD147.FOR | 5'-TGCGT CGACG AGCAG AAACT CATCT CTGAA GAGGA TCTGG AGATG AAGCT GGAAG AGAGC GGCGG-3' | 18 |
| | Fusion-Notch.FOR | 5'-GGCAC CAAGC TGGAG ATCAA GATCC TGGAC TACAG CTTCA CAGG-3' | 19 |
| | Fusion-CD147.REV | 5'-CCTGT GAAGC TGTAG TCCAG GATCT TGATC TCCAG CTTGG TGCC-3' | 20 |
| | SFG-Myc-CD147.REV | 5'-CTAAC GCGTT CATGA TCCGA GCATG TCCAG GTCAA AG-3' | 21 |
| pHR-Gal4UAS-GPC3-CAR-PGK-mCherry | FP-FOR-GPC3 | 5'-TCGACATTCGTTGGATCCGCCAGCATGGAGTTTGGTTTAAGC-3' | 22 |
| | FP-GPC-bbz-overlap | 5'-CGGCT CCGGA ACCAA GCTGG AGATT AAGGA GCCCA AATCT CCTGA CAAAA CTCAC-3' | 23 |
| | RT-GPC-bbz-overlap | 5'-GTGAG TTTTG TCAGG AGATT TGGGC TCCTT AATCT CCAGC TTGGT TCCGG AGCCG-3' | 24 |
| | RP-REV-bbz | 5'-TAGAA TTCGT TAACC TCGAG TTAGC GAGGG GGCAG GGCCT GC-3' | 25 |
| pSFG-Myc-αGPC3-synNotch-Gal4VP64-IRES-GFP | FP-NcoI | 5'-TGCCA CCATG GCAAT GGAGT TTGGT TTAAG CTGGC TGTTT TTAGT GGCCA TTTTA AAGGG CGTG-3' | 26 |
| | RP-MluI | 5'-CAGGA TACGC GTCTT AATCT CCAGC TTGGT TCCGG-3' | 27 |
| | FP-Notch-MluI | 5'-TTAAG ACGCG TATCC TGGAC TACAG CTTCA CAGGT G-3' | 28 |
| | RP-Notch-XhoI | 5'-TCCCG CTCGA GTCAT GATCC GAGCA TGTCC AGG-3' | 29 |
| pHR-Gal4UAS-CD147-CAR-PGK-mCherry | FP-BamHI | 5'-TCGTT GGATC CACGC GTCGT ACGTT AATTA ACCCG GGCAT ATGTT GACTT GCGGC CGCAA C-3' | 30 |
| | RP-BlpI | 5'-CCATT GCTCA GCGGT GCTG-3' | 31 |
| | FP-MluI-147 insert | 5'-GATCC ACGCG TATGG AGTTT GGGCT GAGCT GGC-3' | 32 |
| | RP-NdeI-147 insert | 5'-GTCAA CATAT GTTAG CGAGG GGGCA GGGCC TGCAT G-3' | 33 |
| pSFG-CD147-CAR-28bbz | FP-CD147 Insert | 5'-CTAGA CTGCC ATGGA GTTTG GGCTG AGCTG-3' | 34 |
| | RP-CD147 Insert | 5'-GACGG TGACG TACGT CTTGA TCTCC AGCTT GGTG-3' | 35 |

Figure 22A:
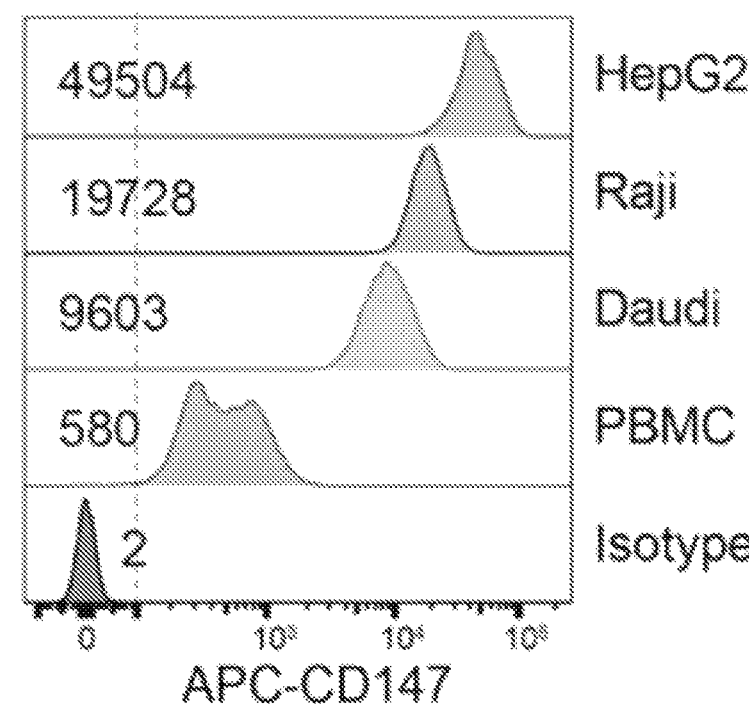
FIGS. 22A and 22B are representative flow cytometric analysis of CD147 expression on different types of cells (FIG. 22A) and cytotoxicity of CD147-CAR-NK-92MI measured by a standard 4-hr $^{51}Cr$ release assay against target cells with different CD147 expression levels (FIG. 22B). Data are representative of two independent experiments. All data are presented as the mean±SEM.
Figure 22B:
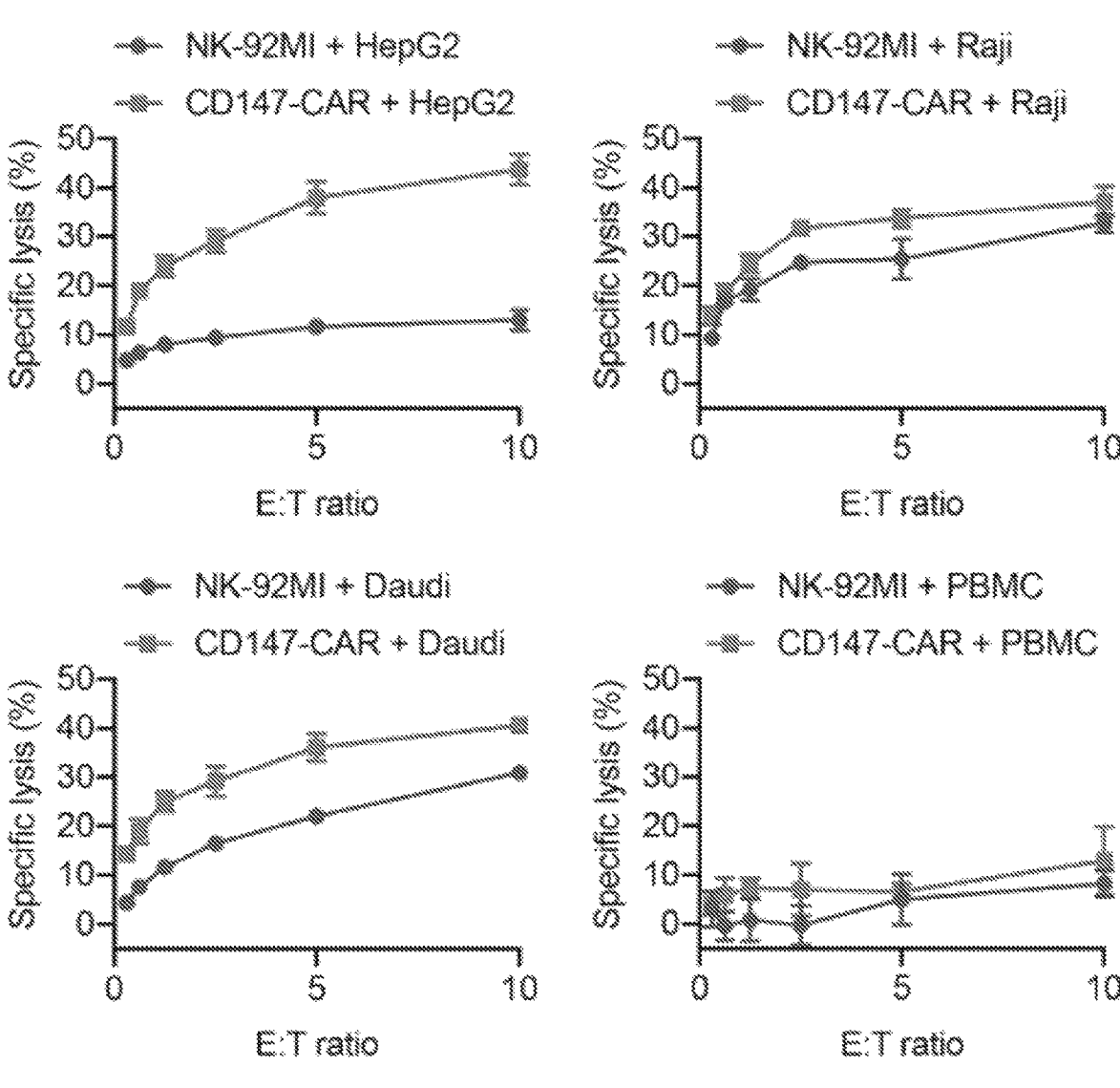

To mitigate off-tumor toxicity to normal tissue, the effect of density of CD147 expression in different types of cells (with a focus on hematopoietic cells) on anti-tumor activity of CD147-CAR was tested. The CD147 expression among HepG2, Raji, Daudi, and PBMCs was assessed. Different expression levels of CD147 were observed (FIG. 22A). Notably, those cells (e.g., PBMCs) expressing low levels of CD147 did not trigger cytotoxicity activity of CD147-CAR-NK-92MI cells, even when CD147-CAR cells were cultured with target cells at the high effector and target ratio (E:T ratio) of 10 to 1 (FIG. 22B). These findings suggest that the optimized scFv sequence of anti-CD147 only allows the specific scFv domain to bind cells with high-expressing CD147 molecules, which can mitigate off-tumor toxicity towards normal tissues that express low levels of CD147 molecules.

To further mitigate off-tumor toxicity of CD147-CAR, a synNotch receptor that can release transcription factors, which in turn drives expression of a CAR against a different tumor antigen, was used. This 'logic-gated' synNotch CAR can only kill dual antigen positive tumor cells, but not single tumor antigen positive tumor cells. A combination approach was designed, consisting of GPC-3 and CD147 to mitigate off-tumor toxicity. Briefly, an SFG retroviral vector encoding an anti-GPC3-specific synNotch receptor linking a Gal4-VP64 intracellular transcription activation domain was constructed. A constitutively expressed enhanced GFP (eGFP) was placed downstream of the GPC3-synNotch to identify transduced cells (FIG. 23A).

A lentiviral vector was constructed in which the anti-CD147-CAR was placed under control of the upstream activating sequence (UAS) promoter that can be activated by Gal4-VP64 transcription factors released after engagement of the synNotch receptor. A constitutively expressed monomeric red fluorescent protein Cherry (mCherry) was placed downstream of the inducible CD147-CAR to identify transduced cells (FIG. 23A).

Figures 23C, 23D:
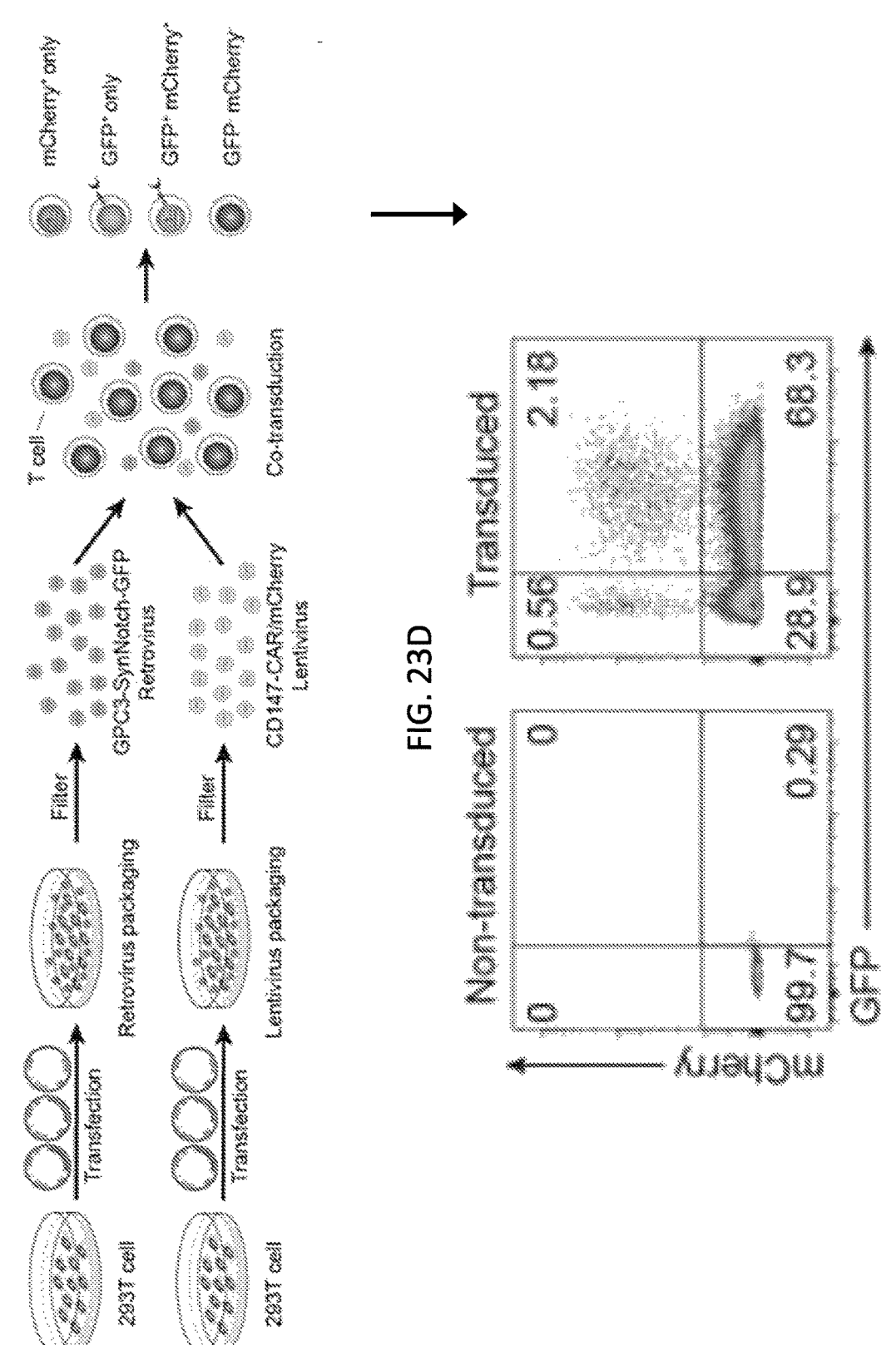
Figures 23E, 23F, 23G, 23H:
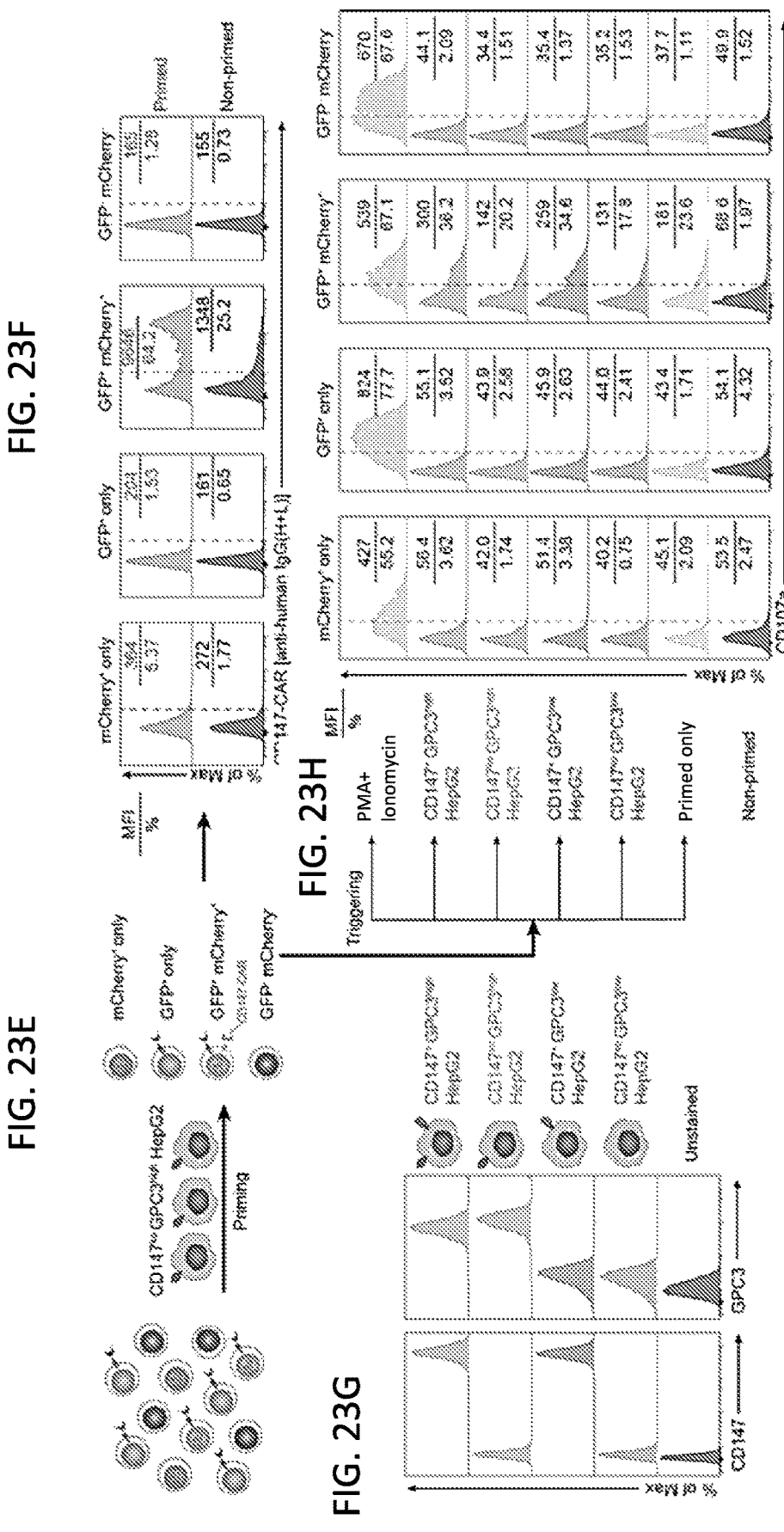
Figure 24:
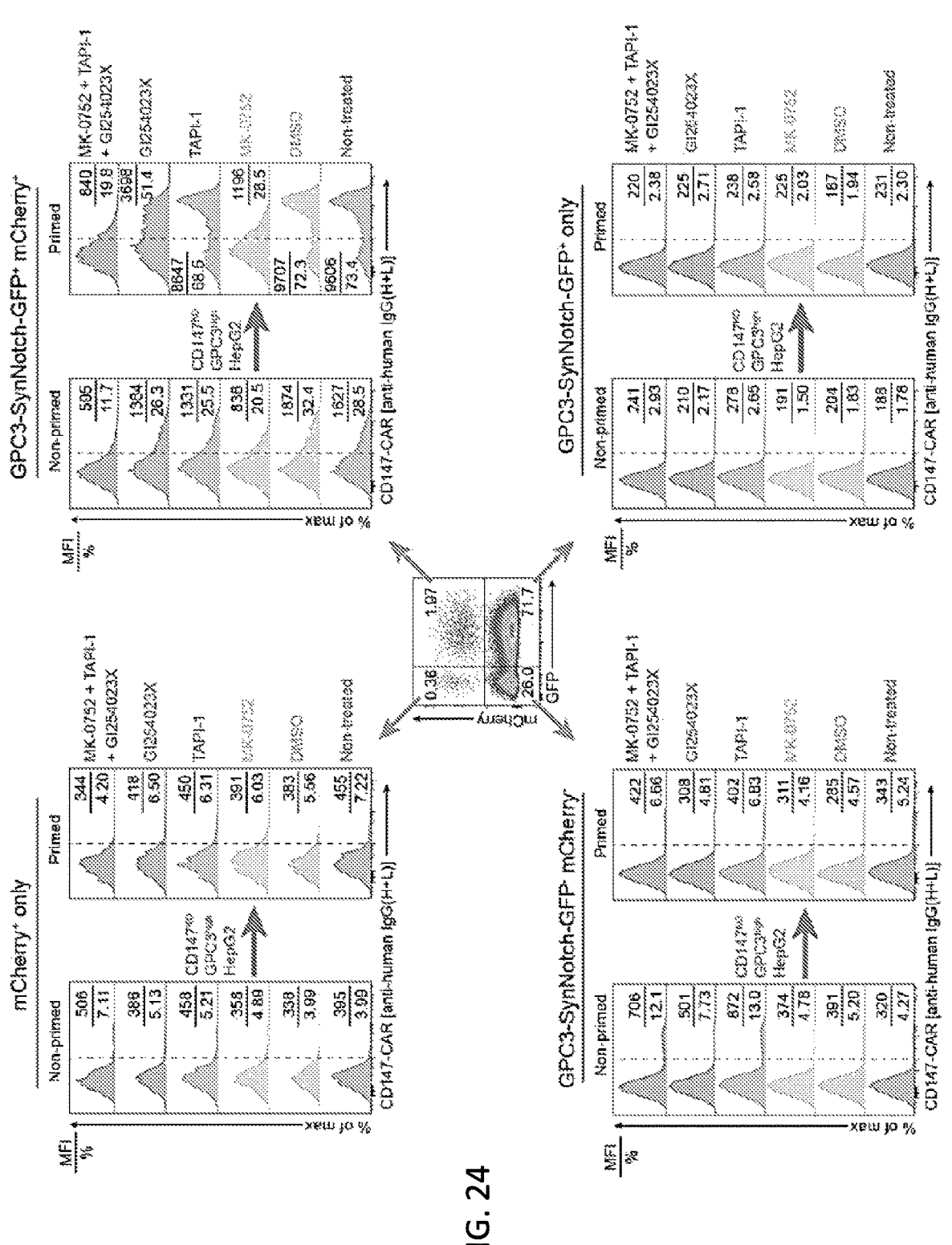
FIG. 24 shows that gamma secretase inhibitor (MK-0752, a Notch signaling inhibitor) specifically blocks the GPC3-SynNotch inducible CD147-CAR expression in the GPC3-SynNotch-eGFP+ and CD147-CAR-mCherry+ primary T cell subset, but not in other subsets of primary T cells. Representative flow cytometric analysis of CD147-CAR expression among different subsets of primary T cells (middle). Transduced T cells were treated with DMSO (0.3%; control), MK-0752 (10 μM), TAPI-1 (10 μM), GI254023X (10 μM), and a combination of MK-0752+TAPI-1+GI254023X, respectively. Meanwhile, these cells were primed in the presence of CD147KO GPC3high HepG2 cells. CD147-CAR expression on the surface of different subsets of transduced T cells was analyzed by flow cytometry. Both mean fluorescence intensity (MFI) and percentage of CD147-CAR are displayed in each representative flow cytometric chart. Data are representative of two independent experiments. All data are presented as the mean±SEM.

Human PBMCs were co-transduced with both lentiviral and retroviral vectors (FIG. 23C). The double positive cells were verified by eGFP (a marker for anti-GPC3-synNotch) and mCherry (a marker for CD147-CAR) using flow cytometry analysis (FIG. 23D). Four subsets of transduced T cells (including mCherry positive only, GFP positive only, GFP and mCherry double positive, and GFP and mCherry double negative subsets) were analyzed (FIG. 23E). These transduced T cells were primed by a GPC3$^{high}$CD147$^{low}$ HepG2 cell line to induce CD147-CAR expression on the surface (FIG. 23F). No CD147-CAR expression was observed in the absence of synNotch engagement. No leakiness of CAR expression was observed in transduced primary T cells. However, about 10% of CAR expression leakiness was observed in transduced NK-92MI cells (data not shown). This observation was further verified by a gamma secretase inhibitor (MK-0752, Notch signaling inhibitor) treatment assay (FIG. 24). The CD147-CAR expression on GPC3-synNotch-GFP and CD147-CAR-mCherry double positive T cells was dramatically inhibited upon MK-0752 treatment (FIG. 24).

Following GPC3-synNotch-GFP and CD147-CAR-mCherry co-transduction T cells and priming by the GPC3$^{high}$CD147$^{low}$ HepG2 cell line, the activity of transduced T cells were triggered by different subsets of HCC cell lines for 2 hours to assess killing efficacy. The different subsets of HCC cell lines were: CD147+GPC3$^{high}$ HepG2 cell line, CD147$^{ko}$GPC3$^{high}$ HepG2 cell line, CD147+GPC3$^{low}$ HepG2 cell line, CD147$^{ko}$GPC3$^{low}$ HepG2 cell line (FIG. 23G). Phorbol-12-myristate-13-acetate (PMA)/ionomycin (IONO) was used as a positive control.

GPC3-synNotch-GFP and CD147-CAR-mCherry double positive T cells that were primed with CD147$^{ko}$GPC3$^{high}$ HepG2 cells could be specifically activated by the CD147+ GPC3$^{high}$ HepG2 cells (FIG. 23H), which was quantified by CD107a surface expression when cocultured with different target cell lines. Similar results were obtained when a myc-tagged CD147 specific-synNotch-GFP and inducible GPC3-CAR-mCherry were co-transduced into T cells (FIGS. 25A-25H).

Together, the data suggest that only synNotch GPC3-inducible CD147-CAR T cells can specifically be activated by GPC3+CD147+ HepG2 cells, but not GPC3+CD147− or GPC3-CD147+ HepG2 cells. These activated CD147-CAR T cells can kill CD147+GPC3+HepG2 cells, but not CD147− GPC3+ HepG2 cells (FIGS. 26A-26D).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

---

I claim:

1. A nucleic acid molecule encoding a chimeric antigen receptor comprising:

(a) an antigen binding domain that specifically binds CD147, wherein the antigen binding domain is encoded by a nucleic acid comprising at least 95% sequence identity to SEQ ID NO: 1, and comprises an amino acid sequence comprising the variable heavy chain (VH) domain complementarity determining region 1 (CDR1), CDR2 and CDR3 amino acid sequences of amino acid positions 26-32, 52-59, and 101-104 of SEQ ID NO: 2, respectively, and the variable light chain (VL) domain CDR1, CDR2 and CDR3 amino acid sequences of amino acid positions 155-165, 181-187, and 220-228 of SEQ ID NO: 2, respectively;

(b) a hinge domain;

(c) a transmembrane domain; and (d) an intracellular domain comprising one or more co-stimulatory molecule intracellular domains and an intracellular signaling domain.

2. The nucleic acid molecule of claim 1, wherein the antigen binding domain has at least 95% sequence identity to the amino acid sequence of SEQ ID NO: 2 or comprises the amino acid sequence of SEQ ID NO: 2.

3. The nucleic acid molecule of claim 1, wherein the one or more co-stimulatory molecule intracellular domains comprise intracellular domains of CD28 and 4-1BB, and/or the intracellular signaling domain comprises a signaling domain of CD3ζ, and/or the hinge domain comprises an IgG1 hinge domain, and/or the transmembrane domain comprises a CD28 transmembrane domain or a CD8a transmembrane domain.

4. The nucleic acid molecule of claim 1, wherein the chimeric antigen receptor comprises an amino acid sequence with at least 98% identity to the amino acid sequence of SEQ ID NO: 5 or comprises the amino acid sequence of SEQ ID NO: 5.

5. The nucleic acid molecule of claim 1, wherein the chimeric antigen receptor further comprises one or more additional antigen binding domains, and/or an inducible suicide molecule, and/or a cytokine receptor intracellular domain.

6. The nucleic acid molecule of claim 5, wherein the chimeric antigen receptor comprises an amino acid sequence with at least 98% identity to the amino acid sequence of SEQ ID NO: 7 or comprises the amino acid sequence of SEQ ID NO: 7.

7. The nucleic acid molecule of claim 1, comprising the nucleic acid sequence of SEQ ID NO: 4, SEQ ID NO: 6, or SEQ ID NO: 14.

8. The nucleic acid molecule of claim 1, wherein the antigen binding domain is encoded by a nucleic acid comprising the nucleic acid sequence of SEQ ID NO: 1.

9. A nucleic acid molecule, comprising at least 95% sequence identity to the nucleic acid sequence of SEQ ID NO: 1, and encoding an antigen binding domain that specifically binds CD147, wherein the antigen binding domain comprises an amino acid sequence comprising the variable heavy chain (VH) domain complementarity determining region 1 (CDR1), CDR2 and CDR3 amino acid sequences of amino acid positions 26-32, 52-59, and 101-104 of SEQ ID NO: 2, respectively, and the variable light chain (VL) domain CDR1, CDR2 and CDR3 amino acid sequences of amino acid positions 155-165, 181-187, and 220-228 of SEQ ID NO: 2, respectively.

10. A vector comprising the nucleic acid molecule of claim 1.

11. The vector of claim 10, further comprising an inducible promoter or enhancer nucleic acid molecule operably linked to the nucleic acid molecule.

12. The vector of claim 11, wherein the vector comprises the nucleic acid sequence of SEQ ID NO: 15.

13. A T cell, natural killer (NK) cell, natural killer T (NKT) cell, double negative T (DNT) cell, neutrophil, or macrophage comprising the nucleic acid molecule of claim 1.

14. A T cell, NK cell, natural killer T (NKT) cell, double negative T (DNT) cell, neutrophil, or macrophage comprising the vector of claim 10.

15. An immune cell, comprising the nucleic acid molecule of claim 1.

16. The nucleic acid molecule of claim 9, comprising the nucleic acid sequence of SEQ ID NO: 1.

17. An immune cell, comprising a chimeric antigen receptor comprising:

(a) an antigen binding domain that specifically binds CD147, wherein the antigen binding domain is encoded by a nucleic acid comprising at least 95% sequence identity to SEQ ID NO: 1, and comprises an amino acid sequence comprising the variable heavy chain (VH) domain complementarity determining region 1 (CDR1), CDR2 and CDR3 amino acid sequences of amino acid positions 26-32, 52-59, and 101-104 of SEQ ID NO: 2, respectively, and the variable light chain (VL) domain CDR1, CDR2 and CDR3 amino acid sequences of amino acid positions 155-165, 181-187, and 220-228 of SEQ ID NO: 2, respectively;

(b) a hinge domain;

(c) a transmembrane domain; and (d) an intracellular domain comprising one or more co-stimulatory molecule intracellular domains and an intracellular signaling domain.

18. The immune cell of claim 17, wherein the antigen binding domain is encoded by a nucleic acid comprising the nucleic acid sequence of SEQ ID NO: 1.

19. The immune cell of claim 18, wherein the cell is a T cell, natural killer (NK) cell, natural killer T (NKT) cell, double negative T (DNT) cell, neutrophil, or macrophage.

20. A method of producing CD147-CAR-T cells or CD147-CAR-NK cells, comprising transducing or transfecting T cells or NK cells with the vector of claim 10.

21. A method of treating a subject with cancer, comprising administering an effective amount of the T cell, NK cell, natural killer T (NKT) cell, double negative T (DNT) cell, neutrophil, or macrophage of claim 13 to the subject, wherein the cancer expresses CD147.

22. The method of claim 21, wherein the subject has hepatocellular carcinoma, neuroblastoma, breast cancer, pancreatic cancer, leukemia, lymphoma, multiple myeloma, colorectal cancer, lung cancer, melanoma, renal cell carcinoma, sarcoma, or nasopharyngeal carcinoma.

\* \* \* \* \*

SEQUENCE LISTING

```
<160> NUMBER OF SEQ ID NOS: 47

<210> SEQ ID NO 1
<211> LENGTH: 729
<212> TYPE: DNA
<213> ORGANISM: Artificial Sequence
<220> FEATURE:
<223> OTHER INFORMATION: Modified CD147 ScFv

<400> SEQUENCE: 1
gagatgaagc tggaagagag cggcggcgga ctggtgcagc ccggcggcag catgaagctg      60
agctgcgtgg cctccggctt caccttcagc aactactgga tgaactgggt gagacagtcc     120
cccgaaaagg gcctggagtg ggtggcccag atcagactga gtcctacaa ctacgccacc     180 cactacgccg agagcgtgaa gggcagattc accatctcca gggacgactc caagtcctcc     240
gtgtacctgc agatgaacaa cctgagagcc gaggacaccg gcatctacta ctgcacccc      300 gatggcagcg actattgggg ccagggcaca acactcaccg tgagctccgg cggcggaggc     360
agcggcggcg gcggcagcgg cggcggcggc tccggcggag gcggcagcag catcgtgatg     420
acccagaccc ccaagttcct cctggtgagc gccggcgata gggtgaccat tacctgcaag     480
gcctcccagt ccgtgagcaa cgatgtggcc tggtaccagc agaagcccgg ccagagccct     540
aagctgctga tctactacgc cagcaacagg tacacaggcg tgcccgacag gtttaccggc     600
tccggctacg gcaccgactt caccttcacc atcagcacag tgcaggccga ggacctggcc     660
gtgtacttct gccagcagga ctactccagc ccctacacct tcggaggcgg caccaagctg     720
gagatcaag                                                              729

<210> SEQ ID NO 2
<211> LENGTH: 238
<212> TYPE: PRT
<213> ORGANISM: Artificial Sequence
<220> FEATURE:
<223> OTHER INFORMATION: Modified CD147 scFv

<400> SEQUENCE: 2

Glu Met Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45
```

```
Ala Gln Ile Arg Leu Lys Ser Tyr Asn Tyr Ala Thr His Tyr Ala Glu
    50              55                  60

Ser Val Lys Gly Arg Phe Thr Ile Ser Arg Asp Asp Ser Lys Ser Ser
65              70                  75                  80

Val Tyr Leu Gln Met Asn Asn Leu Arg Ala Glu Asp Thr Gly Ile Tyr
                85                  90                  95

Tyr Cys Thr Pro Asp Gly Ser Asp Tyr Trp Gly Gln Gly Thr Thr Leu
            100                 105                 110

Thr Val Ser Ser Gly Gly Gly Ser Gly Gly Gly Gly Ser Gly Gly
            115                 120                 125

Gly Gly Ser Ser Ile Val Met Thr Gln Thr Pro Lys Phe Leu Leu Val
    130                 135                 140

Ser Ala Gly Asp Arg Val Thr Ile Thr Cys Lys Ala Ser Gln Ser Val
145                 150                 155                 160

Ser Asn Asp Val Ala Trp Tyr Gln Gln Lys Pro Gly Gln Ser Pro Lys
                165                 170                 175

Leu Leu Ile Tyr Tyr Ala Ser Asn Arg Tyr Thr Gly Val Pro Asp Arg
            180                 185                 190

Phe Thr Gly Ser Gly Tyr Gly Thr Asp Phe Thr Phe Thr Ile Ser Thr
            195                 200                 205

Val Gln Ala Glu Asp Leu Ala Val Tyr Phe Cys Gln Gln Asp Tyr Ser
    210                 215                 220

Ser Pro Tyr Thr Phe Gly Gly Gly Thr Lys Leu Glu Ile Lys
225                 230                 235
```

<210> SEQ ID NO 3
<211> LENGTH: 729
<212> TYPE: DNA
<213> ORGANISM: Artificial Sequence
<220> FEATURE:
<223> OTHER INFORMATION: CD147 scFv

<400> SEQUENCE: 3

```
gagatgaagc ttgaggagag tggtggtggt cttgttcagc ctggtggtag tatgaagctt      60
agttgcgttg ctagtggttt cactttcagt aactactgga tgaactgggt tcgtcagagt     120
cctgagaagg gtcttgagtg ggttgctcag atccgtctta agagttacaa ctacgctact     180
cactacgctg agagtgttaa gggtcgtttc actatcagtc gtgacgacag taagagtagt     240
gtttaccttc agatgaacaa ccttcgtgct gaggacactg gtatctacta ctgcactcct     300
gacggtagtg actactgggg tcagggtact actcttactg ttagtagtgg tggtggtggt     360
tctggtggtg gtggttctgg cggcggcggc tccggtggtg gtggctccag tatcgttatg     420
actcagactc ctaagttcct tcttgttagt gctggtgacc gtgttactat cacttgcaag     480
gctagtcaga gtgttagtaa cgacgttgct tggtaccagc agaagcctgg tcagagtcct     540
aagcttctta tctactacgc tagtaaccgt tacactggtg ttcctgaccg tttcactggt     600
agtggttacg gtactgactt cactttcact atcagtactg ttcaggctga ggaccttgct     660
gtttacttct gccagcagga ctacagtagt ccttacactt tcggtggtgg tactaagctt     720
gagatcaag                                                            729
```

<210> SEQ ID NO 4
<211> LENGTH: 2202
<212> TYPE: DNA
<213> ORGANISM: Artificial Sequence
<220> FEATURE:

<223> OTHER INFORMATION: CD147 CAR

<400> SEQUENCE: 4

```
atggagtttg ggctgagctg gctttttctt gtggctattt taaaaggtgt ccagtgcgtc      60
gacgagatga agctggaaga gagcggcggc ggactggtgc agcccggcgg cagcatgaag     120
ctgagctgcg tggcctccgg cttcaccttc agcaactact ggatgaactg ggtgagacag     180
tcccccgaaa agggcctgga gtgggtggcc cagatcagac tgaagtccta caactacgcc     240
acccactacg ccgagagcgt gaagggcaga ttcaccatct ccagggacga ctccaagtcc     300
tccgtgtacc tgcagatgaa caacctgaga gccgaggaca ccggcatcta ctactgcacc     360
cccgatggca gcgactattg gggccagggc acaacactca ccgtgagctc cggcggcgga     420
ggcagcggcg gcggcggcag cggcggcggc ggctccggcg gaggcggcag cagcatcgtg     480
atgacccaga cccccaagtt cctcctggtg agcgccggca taggggtgac cattacctgc     540
aaggcctccc agtccgtgag caacgatgtg cctggtacc agcagaagcc cggccagagc     600
cctaagctgc tgatctacta cgccagcaac aggtacacag gcgtgcccga caggtttacc     660
ggctccggct acggcaccga cttcaccttc accatcagca cagtgcaggc cgaggacctg     720
gccgtgtact tctgccagca ggactactcc agcccctaca ccttcggagg cggcaccaag     780
ctggagatca gaacgtacgt caccgtctct tcacaggatc ccgccgagcc caaatctcct     840
gacaaaactc acacatgccc accgtgccca gcacctgaac tcctgggggg accgtcagtc     900
ttcctcttcc ccccaaaacc caaggacacc ctcatgatct cccggacccc tgaggtcaca     960
tgcgtggtgg tggacgtgag ccacgaagac cctgaggtca agttcaactg gtacgtggac    1020
ggcgtggagg tgcataatgc caagacaaag ccgcgggagg agcagtacaa cagcacgtac    1080
cgtgtggtca gcgtcctcac cgtcctgcac caggactggc tgaatggcaa ggagtacaag    1140
tgcaaggtct ccaacaaagc cctcccagcc cccatcgaga aaaccatctc caaagccaaa    1200
gggcagcccc gagaaccaca ggtgtacacc ctgcccccat cccgggatga gctgaccaag    1260
aaccaggtca gcctgacctg cctggtcaaa ggcttctatc ccagcgacat cgccgtggag    1320
tgggagagca atgggcaacc ggagaacaac tacaagacca cgcctcccgt gctggactcc    1380
gacggctcct tcttcctcta cagcaagctc accgtggaca gagcaggtg gcagcagggg    1440 aacgtcttct catgctccgt gatgcatgag gctctgcaca accactacac gcagaagagc    1500
ctctccctgt ctccgggtaa aaaagatccc aaattttggg tgctggtggt ggttggtgga    1560
gtcctggctt gctatagctt gctagtaaca gtggccttta ttatttttg ggtgaggagt    1620 aagaggagca ggctcctgca cagtgactac atgaacatga ctccccgccg ccccgggccc    1680
acccgcaagc attaccagcc ctatgcccca ccacgcgact cgcagcccta tcgctccaaa    1740
cggggcagaa agaaactcct gtatatattc aaacaaccat ttatgagacc agtacaaact    1800
actcaagagg aagatggctg tagctgccga tttccagaag aagaagaagg aggatgtgaa    1860
ctgagagtga agttcagcag gagcgcagac gcccccgcgt accagcaggg ccagaaccag    1920
ctctataacg agctcaatct aggacgaaga gaggagtacg atgttttgga caagagacgt    1980
ggccgggacc ctgagatggg gggaaagccg agaaggaaga cccctcagga aggcctgtac    2040
aatgaactgc agaaagataa gatggcggag gcctacagtg agattgggat gaaaggcgag    2100
cgccggaggg gcaaggggca cgatggcctt taccagggtc tcagtacagc caccaaggac    2160
acctacgacg cccttcacat gcaggccctg cccctcgct aa                        2202
```

<210> SEQ ID NO 5
<211> LENGTH: 733
<212> TYPE: PRT
<213> ORGANISM: Artificial Sequence
<220> FEATURE:
<223> OTHER INFORMATION: CD147 CAR

<400> SEQUENCE: 5

Met Glu Phe Gly Leu Ser Trp Leu Phe Leu Val Ala Ile Leu Lys Gly
1               5                   10                  15

Val Gln Cys Val Asp Glu Met Lys Leu Glu Glu Ser Gly Gly Gly Leu
            20                  25                  30

Val Gln Pro Gly Gly Ser Met Lys Leu Ser Cys Val Ala Ser Gly Phe
        35                  40                  45

Thr Phe Ser Asn Tyr Trp Met Asn Trp Val Arg Gln Ser Pro Glu Lys
    50                  55                  60

Gly Leu Glu Trp Val Ala Gln Ile Arg Leu Lys Ser Tyr Asn Tyr Ala
65                  70                  75                  80

Thr His Tyr Ala Glu Ser Val Lys Gly Arg Phe Thr Ile Ser Arg Asp
                85                  90                  95

Asp Ser Lys Ser Ser Val Tyr Leu Gln Met Asn Asn Leu Arg Ala Glu
            100                 105                 110

Asp Thr Gly Ile Tyr Tyr Cys Thr Pro Asp Gly Ser Asp Tyr Trp Gly
        115                 120                 125

Gln Gly Thr Thr Leu Thr Val Ser Ser Gly Gly Gly Gly Ser Gly Gly
        130                 135                 140

Gly Gly Ser Gly Gly Gly Gly Ser Gly Gly Gly Gly Ser Ser Ile Val
145                 150                 155                 160

Met Thr Gln Thr Pro Lys Phe Leu Leu Val Ser Ala Gly Asp Arg Val
                165                 170                 175

Thr Ile Thr Cys Lys Ala Ser Gln Ser Val Ser Asn Asp Val Ala Trp
            180                 185                 190

Tyr Gln Gln Lys Pro Gly Gln Ser Pro Lys Leu Leu Ile Tyr Tyr Ala
        195                 200                 205

Ser Asn Arg Tyr Thr Gly Val Pro Asp Arg Phe Thr Gly Ser Gly Tyr
        210                 215                 220

Gly Thr Asp Phe Thr Phe Thr Ile Ser Thr Val Gln Ala Glu Asp Leu
225                 230                 235                 240

Ala Val Tyr Phe Cys Gln Gln Asp Tyr Ser Ser Pro Tyr Thr Phe Gly
                245                 250                 255

Gly Gly Thr Lys Leu Glu Ile Lys Thr Tyr Val Thr Val Ser Ser Gln
            260                 265                 270

Asp Pro Ala Glu Pro Lys Ser Pro Asp Lys Thr His Thr Cys Pro Pro
        275                 280                 285

Cys Pro Ala Pro Glu Leu Leu Gly Gly Pro Ser Val Phe Leu Phe Pro
    290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

Glu Glu Gln Tyr Asn Ser Thr Tyr Arg Val Val Ser Val Leu Thr Val
        355                 360                 365

-continued

```
Leu His Gln Asp Trp Leu Asn Gly Lys Glu Tyr Lys Cys Lys Val Ser
    370             375             380

Asn Lys Ala Leu Pro Ala Pro Ile Glu Lys Thr Ile Ser Lys Ala Lys
385             390             395             400

Gly Gln Pro Arg Glu Pro Gln Val Tyr Thr Leu Pro Pro Ser Arg Asp
            405             410             415

Glu Leu Thr Lys Asn Gln Val Ser Leu Thr Cys Leu Val Lys Gly Phe
        420             425             430

Tyr Pro Ser Asp Ile Ala Val Glu Trp Glu Ser Asn Gly Gln Pro Glu
        435             440             445

Asn Asn Tyr Lys Thr Thr Pro Pro Val Leu Asp Ser Asp Gly Ser Phe
    450             455             460

Phe Leu Tyr Ser Lys Leu Thr Val Asp Lys Ser Arg Trp Gln Gln Gly
465             470             475             480

Asn Val Phe Ser Cys Ser Val Met His Glu Ala Leu His Asn His Tyr
            485             490             495

Thr Gln Lys Ser Leu Ser Leu Ser Pro Gly Lys Lys Asp Pro Lys Phe
        500             505             510

Trp Val Leu Val Val Val Gly Gly Val Leu Ala Cys Tyr Ser Leu Leu
        515             520             525

Val Thr Val Ala Phe Ile Ile Phe Trp Val Arg Ser Lys Arg Ser Arg
    530             535             540

Leu Leu His Ser Asp Tyr Met Asn Met Thr Pro Arg Arg Pro Gly Pro
545             550             555             560

Thr Arg Lys His Tyr Gln Pro Tyr Ala Pro Pro Arg Asp Phe Ala Ala
            565             570             575

Tyr Arg Ser Lys Arg Gly Arg Lys Lys Leu Leu Tyr Ile Phe Lys Gln
        580             585             590

Pro Phe Met Arg Pro Val Gln Thr Thr Gln Glu Glu Asp Gly Cys Ser
        595             600             605

Cys Arg Phe Pro Glu Glu Glu Glu Gly Gly Cys Glu Leu Arg Val Lys
    610             615             620

Phe Ser Arg Ser Ala Asp Ala Pro Ala Tyr Gln Gln Gly Gln Asn Gln
625             630             635             640

Leu Tyr Asn Glu Leu Asn Leu Gly Arg Arg Glu Glu Tyr Asp Val Leu
            645             650             655

Asp Lys Arg Arg Gly Arg Asp Pro Glu Met Gly Gly Lys Pro Arg Arg
            660             665             670

Lys Asn Pro Gln Glu Gly Leu Tyr Asn Glu Leu Gln Lys Asp Lys Met
        675             680             685

Ala Glu Ala Tyr Ser Glu Ile Gly Met Lys Gly Glu Arg Arg Arg Gly
        690             695             700

Lys Gly His Asp Gly Leu Tyr Gln Gly Leu Ser Thr Ala Thr Lys Asp
705             710             715             720

Thr Tyr Asp Ala Leu His Met Gln Ala Leu Pro Pro Arg
            725             730
```

<210> SEQ ID NO 6
<211> LENGTH: 3402
<212> TYPE: DNA
<213> ORGANISM: Artificial Sequence
<220> FEATURE:
<223> OTHER INFORMATION: CD147 CAR with inducible caspase 9

```
<400> SEQUENCE: 6
atgctcgagg gagtgcaggt ggagactatc tccccaggag acgggcgcac cttccccaag        60
cgcggccaga cctgcgtggt gcactacacc gggatgcttg aagatggaaa gaaagttgat       120
tcctcccggg acagaaacaa gccctttaag tttatgctag gcaagcagga ggtgatccga       180
ggctgggaag aagggggttgc ccagatgagt gtgggtcaga gagccaaact gactatatct       240
ccagattatg cctatggtgc cactgggcac ccaggcatca tcccaccaca tgccactctc       300
gtcttcgatg tggagcttct aaaactggaa tctggcggtg gatccggagt cgacggattt       360
ggtgatgtcg gtgctcttga gagtttgagg ggaaatgcag atttggctta catcctgagc       420
atggagccct gtggccactg cctcattatc aacaatgtga acttctgccg tgagtccggg       480
ctccgcaccc gcactggctc caacatcgac tgtgagaagt tgcggcgtcg cttctcctcg       540
ctgcatttca tggtggaggt gaagggcgac ctgactgcca agaaaatggt gctggctttg       600
ctggagctgg cgcagcagga ccacggtgct ctggactgct gcgtggtggt cattctctct       660
cacggctgtc aggccagcca cctgcagttc ccaggggctg tctacggcac agatggatgc       720
cctgtgtcgg tcgagaagat tgtgaacatc ttcaatggga ccagctgccc cagcctggga       780
gggaagccca agctctttt catccaggcc tgtggtgggg agcagaaaga ccatgggttt       840
gaggtggcct ccacttcccc tgaagacgag tccctggca gtaaccccga gccagatgcc       900
accccgttcc aggaaggttt gaggaccttc gaccagctgg acgccatatc tagtttgccc       960
acacccagtg acatctttgt gtcctactct actttcccag gttttgtttc ctggagggac      1020
cccaagagtg gctcctggta cgttgagacc ctggacgaca tctttgagca gtgggctcac      1080
tctgaagacc tgcagtccct cctgcttagg gtcgctaatg ctgtttcggt gaaagggatt      1140
tataaacaga tgcctggttg ctttaatttc ctccggaaaa acttttctt taaaacatca      1200 gagggcagag gaagtctgct aacatgcggt gacgtcgagg agaatcctgg cccagcggcc      1260
gctgagatga agctggaaga gagcggcggc ggactggtgc agcccggcgg cagcatgaag      1320
ctgagctgcg tggcctccgg cttcaccttc agcaactact ggatgaactg ggtgagacag      1380
tcccccgaaa agggcctgga gtgggtggcc cagatcagac tgaagtccta caactacgcc      1440
acccactacg ccgagagcgt gaagggcaga ttcaccatct ccagggacga ctccaagtcc      1500
tccgtgtacc tgcagatgaa caacctgaga gccgaggaca ccggcatcta ctactgcacc      1560
cccgatggca gcgactattg gggccagggc acaacactca ccgtgagctc cggcggcgga      1620
ggcagcggcg gcggcggcag cggcggcggc ggctccggcg gaggcggcag cagcatcgtg      1680
atgacccaga cccccaagtt cctcctggtg agcgccggcg atagggtgac cattacctgc      1740
aaggcctccc agtccgtgag caacgatgtg gcctggtacc agcagaagcc cggccagagc      1800
cctaagctgc tgatctacta cgccagcaac aggtacacag gcgtgcccga caggtttacc      1860
ggctccggct acggcaccga cttcaccttc accatcagca cagtgcaggc cgaggacctg      1920
gccgtgtact tctgccagca ggactactcc agcccctaca ccttcggagg cggcaccaag      1980
ctggagatca gtcgtacgt caccgtctct tcacaggatc ccgccgagcc caaatctcct      2040
gacaaaactc acacatgccc accgtgccca gcacctgaac tcctgggggg accgtcagtc      2100
ttcctcttcc ccccaaaacc caaggacacc ctcatgatct cccggacccc tgaggtcaca      2160
tgcgtggtgg tggacgtgag ccacgaagac cctgaggtca agttcaactg gtacgtggac      2220
ggcgtggagg tgcataatgc caagacaaag ccgcgggagg agcagtacaa cagcacgtac      2280
```

```
cgtgtggtca gcgtcctcac cgtcctgcac caggactggc tgaatggcaa ggagtacaag   2340
tgcaaggtct ccaacaaagc cctcccagcc cccatcgaga aaaccatctc caaagccaaa   2400
gggcagcccc gagaaccaca ggtgtacacc ctgcccccat cccgggatga gctgaccaag   2460
aaccaggtca gcctgacctg cctggtcaaa ggcttctatc ccagcgacat cgccgtggag   2520
tgggagagca atgggcaacc ggagaacaac tacaagacca cgcctcccgt gctggactcc   2580
gacggctcct tcttcctcta cagcaagctc accgtggaca gagcaggtg gcagcagggg   2640 aacgtcttct catgctccgt gatgcatgag gctctgcaca ccactacac gcagaagagc   2700 ctctccctgt ctccgggtaa aaaagatccc aaattttggg tgctggtggt ggttggtgga   2760
gtcctggctt gctatagctt gctagtaaca gtggccttta ttatttttg ggtgaggagt   2820 aagaggagca ggctcctgca cagtgactac atgaacatga ctccccgccg ccccgggccc   2880
acccgcaagc attaccagcc ctatgcccca ccacgcgact tcgcagccta tcgctccaaa   2940
cggggcagaa agaaactcct gtatatattc aaacaaccat ttatgagacc agtacaaact   3000
actcaagagg aagatggctg tagctgccga tttccagaag aagaagaagg aggatgtgaa   3060
ctgagagtga agttcagcag gagcgcagac gcccccgcgt accagcaggg ccagaaccag   3120
ctctataacg agctcaatct aggacgaaga gaggagtacg atgttttgga caagagacgt   3180
ggccgggacc ctgagatggg gggaaagccg agaaggaaga accctcagga aggcctgtac   3240
aatgaactgc agaaagataa gatggcggag gcctacagtg agattgggat gaaaggcgag   3300
cgccggaggg gcaagggggca cgatggcctt taccagggtc tcagtacagc caccaaggac   3360
acctacgacg cccttcacat gcaggccctg cccctcgct aa                       3402
```

```
<210> SEQ ID NO 7
<211> LENGTH: 1133
<212> TYPE: PRT
<213> ORGANISM: Artificial Sequence
<220> FEATURE:
<223> OTHER INFORMATION: CD147 CAR with inducible caspase 9

<400> SEQUENCE: 7

Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
    130                 135                 140

Gly His Cys Leu Ile Ile Asn Asn Val Asn Phe Cys Arg Glu Ser Gly
145                 150                 155                 160
```

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Val Ile Leu Ser His Gly Cys Gln
        210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
        290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
            325                 330                 335

Ser Trp Arg Asp Pro Lys Ser Gly Ser Trp Tyr Val Glu Thr Leu Asp
            340                 345                 350

Asp Ile Phe Glu Gln Trp Ala His Ser Glu Asp Leu Gln Ser Leu Leu
            355                 360                 365

Leu Arg Val Ala Asn Ala Val Ser Val Lys Gly Ile Tyr Lys Gln Met
        370                 375                 380

Pro Gly Cys Phe Asn Phe Leu Arg Lys Lys Leu Phe Phe Lys Thr Ser
385                 390                 395                 400

Glu Gly Arg Gly Ser Leu Leu Thr Cys Gly Asp Val Glu Glu Asn Pro
                405                 410                 415

Gly Pro Ala Ala Ala Glu Met Lys Leu Glu Glu Ser Gly Gly Gly Leu
            420                 425                 430

Val Gln Pro Gly Gly Ser Met Lys Leu Ser Cys Val Ala Ser Gly Phe
            435                 440                 445

Thr Phe Ser Asn Tyr Trp Met Asn Trp Val Arg Gln Ser Pro Glu Lys
        450                 455                 460

Gly Leu Glu Trp Val Ala Gln Ile Arg Leu Lys Ser Tyr Asn Tyr Ala
465                 470                 475                 480

Thr His Tyr Ala Glu Ser Val Lys Gly Arg Phe Thr Ile Ser Arg Asp
            485                 490                 495

Asp Ser Lys Ser Ser Val Tyr Leu Gln Met Asn Asn Leu Arg Ala Glu
        500                 505                 510

Asp Thr Gly Ile Tyr Tyr Cys Thr Pro Asp Gly Ser Asp Tyr Trp Gly
        515                 520                 525

Gln Gly Thr Thr Leu Thr Val Ser Ser Gly Gly Gly Ser Gly Gly
        530                 535                 540

Gly Gly Ser Gly Gly Gly Gly Ser Gly Gly Gly Gly Ser Ser Ile Val
545                 550                 555                 560

Met Thr Gln Thr Pro Lys Phe Leu Leu Val Ser Ala Gly Asp Arg Val
                565                 570                 575

-continued

```
Thr Ile Thr Cys Lys Ala Ser Gln Ser Val Ser Asn Asp Val Ala Trp
            580             585             590

Tyr Gln Gln Lys Pro Gly Gln Ser Pro Lys Leu Leu Ile Tyr Tyr Ala
        595             600             605

Ser Asn Arg Tyr Thr Gly Val Pro Asp Arg Phe Thr Gly Ser Gly Tyr
    610             615             620

Gly Thr Asp Phe Thr Phe Thr Ile Ser Thr Val Gln Ala Glu Asp Leu
625             630             635             640

Ala Val Tyr Phe Cys Gln Gln Asp Tyr Ser Ser Pro Tyr Thr Phe Gly
            645             650             655

Gly Gly Thr Lys Leu Glu Ile Lys Ser Tyr Val Thr Val Ser Ser Gln
            660             665             670

Asp Pro Ala Glu Pro Lys Ser Pro Asp Lys Thr His Thr Cys Pro Pro
        675             680             685

Cys Pro Ala Pro Glu Leu Leu Gly Gly Pro Ser Val Phe Leu Phe Pro
    690             695             700

Pro Lys Pro Lys Asp Thr Leu Met Ile Ser Arg Thr Pro Glu Val Thr
705             710             715             720

Cys Val Val Val Asp Val Ser His Glu Asp Pro Glu Val Lys Phe Asn
            725             730             735

Trp Tyr Val Asp Gly Val Glu Val His Asn Ala Lys Thr Lys Pro Arg
            740             745             750

Glu Glu Gln Tyr Asn Ser Thr Tyr Arg Val Val Ser Val Leu Thr Val
            755             760             765

Leu His Gln Asp Trp Leu Asn Gly Lys Glu Tyr Lys Cys Lys Val Ser
    770             775             780

Asn Lys Ala Leu Pro Ala Pro Ile Glu Lys Thr Ile Ser Lys Ala Lys
785             790             795             800

Gly Gln Pro Arg Glu Pro Gln Val Tyr Thr Leu Pro Pro Ser Arg Asp
            805             810             815

Glu Leu Thr Lys Asn Gln Val Ser Leu Thr Cys Leu Val Lys Gly Phe
            820             825             830

Tyr Pro Ser Asp Ile Ala Val Glu Trp Glu Ser Asn Gly Gln Pro Glu
        835             840             845

Asn Asn Tyr Lys Thr Thr Pro Pro Val Leu Asp Ser Asp Gly Ser Phe
    850             855             860

Phe Leu Tyr Ser Lys Leu Thr Val Asp Lys Ser Arg Trp Gln Gln Gly
865             870             875             880

Asn Val Phe Ser Cys Ser Val Met His Glu Ala Leu His Asn His Tyr
            885             890             895

Thr Gln Lys Ser Leu Ser Leu Ser Pro Gly Lys Lys Asp Pro Lys Phe
            900             905             910

Trp Val Leu Val Val Val Gly Gly Val Leu Ala Cys Tyr Ser Leu Leu
            915             920             925

Val Thr Val Ala Phe Ile Ile Phe Trp Val Arg Ser Lys Arg Ser Arg
    930             935             940

Leu Leu His Ser Asp Tyr Met Asn Met Thr Pro Arg Arg Pro Gly Pro
945             950             955             960

Thr Arg Lys His Tyr Gln Pro Tyr Ala Pro Pro Arg Asp Phe Ala Ala
            965             970             975

Tyr Arg Ser Lys Arg Gly Arg Lys Lys Leu Leu Tyr Ile Phe Lys Gln
            980             985             990
```

```
Pro Phe Met Arg Pro Val Gln Thr  Thr Gln Glu Glu Asp  Gly Cys Ser
        995                 1000                 1005

Cys Arg  Phe Pro Glu Glu Glu  Glu Gly Gly Cys Glu  Leu Arg Val
    1010                 1015                 1020

Lys Phe  Ser Arg Ser Ala Asp  Ala Pro Ala Tyr Gln  Gln Gly Gln
    1025                 1030                 1035

Asn Gln  Leu Tyr Asn Glu Leu  Asn Leu Gly Arg Arg  Glu Glu Tyr
    1040                 1045                 1050

Asp Val  Leu Asp Lys Arg Arg  Gly Arg Asp Pro Glu  Met Gly Gly
    1055                 1060                 1065

Lys Pro  Arg Arg Lys Asn Pro  Gln Glu Gly Leu Tyr  Asn Glu Leu
    1070                 1075                 1080

Gln Lys  Asp Lys Met Ala Glu  Ala Tyr Ser Glu Ile  Gly Met Lys
    1085                 1090                 1095

Gly Glu  Arg Arg Arg Gly Lys  Gly His Asp Gly Leu  Tyr Gln Gly
    1100                 1105                 1110

Leu Ser  Thr Ala Thr Lys Asp  Thr Tyr Asp Ala Leu  His Met Gln
    1115                 1120                 1125

Ala Leu  Pro Pro Arg
    1130

<210> SEQ ID NO 8
<211> LENGTH: 116
<212> TYPE: PRT
<213> ORGANISM: Artificial Sequence
<220> FEATURE:
<223> OTHER INFORMATION: anti-CD147 VH CDR domain

<400> SEQUENCE: 8

Glu Met Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Tyr Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Pro Asp Gly Ser Asp Tyr Trp Gly Gln Gly Thr Thr Leu
            100                 105                 110

Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: anti-CD147 VL CDR domain

<400> SEQUENCE: 9

Ser Ile Val Met Thr Gln Thr Pro Lys Phe Leu Leu Val Ser Ala Gly
1               5                   10                  15
```

-continued

```
Asp Arg Val Thr Ile Thr Cys Lys Ala Ser Gln Ser Val Ser Asn Asp
        20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105
```

<210> SEQ ID NO 10
<211> LENGTH: 20
<212> TYPE: DNA
<213> ORGANISM: Artificial Sequence
<220> FEATURE:
<223> OTHER INFORMATION: guide RNA targeting CD147

<400> SEQUENCE: 10

```
ttgacatcgt tggccaccgc                                                 20
```

<210> SEQ ID NO 11
<211> LENGTH: 20
<212> TYPE: DNA
<213> ORGANISM: Artificial Sequence
<220> FEATURE:
<223> OTHER INFORMATION: Guide RNA targeting CD147

<400> SEQUENCE: 11

```
gtggacgcag atgaccgctc                                                 20
```

<210> SEQ ID NO 12
<211> LENGTH: 489
<212> TYPE: DNA
<213> ORGANISM: Artificial Sequence
<220> FEATURE:
<223> OTHER INFORMATION: IL-15 receptor intracellular domain

<400> SEQUENCE: 12

```
atgcggatca gcaagcccca cctgcggagc atcagcatcc agtgctacct gtgcctgctg      60
ctgaacagcc acttcctgac cgaggccggc atccacgtgt tcatcctggg ctgcttcagc     120
gccggactgc ccaagaccga ggccaactgg gtgaacgtga tcagcgacct gaagaagatc     180
gaggacctga tccagagcat gcacatcgac gccaccctgt acaccgagag cgacgtgcac     240
cccagctgca aggtgaccgc catgaagtgc tttctgctgg aactgcaggt gatcagcctg     300
gaaagcggcg acgccagcat ccacgacacc gtggagaacc tgatcatcct ggccaacaac     360
agcctgagca gcaacggcaa cgtgaccgag agcggctgca agagtgcga ggaactggaa      420 gagaagaaca tcaaagagtt tctgcagagc ttcgtgcaca tcgtgcagat gttcatcaac     480
accagctga                                                             489
```

<210> SEQ ID NO 13
<211> LENGTH: 729
<212> TYPE: DNA
<213> ORGANISM: Artificial Sequence
<220> FEATURE:
<223> OTHER INFORMATION: Consensus scFv sequence -continued

```
<400> SEQUENCE: 13
gagatgaagc tggaagagag cggcggcgga ctggtgcagc ccggcggcag catgaagctg      60
agctgcgtgg ccaccggctt caccttcagc aactactgga tgaactgggt gagacagacc     120
cccgaaaagg gcctggagtg ggtggcccag atcagactga agacctacaa ctacgccacc     180
cactacgccg agagcgtgaa gggcagattc accatcacca gggacgacac caagaccacc     240
gtgtacctgc agatgaacaa cctgagagcc gaggacaccg gcatctacta ctgcaccccc     300
gacggcagcg actactgggg ccagggcaca acactcaccg tgagcaccgg cggcggaggc     360
accggcggcg cggcaccggg cggcggcggc tccggcggag cggcaccagg catcgtgatg     420
acccagaccc ccaagttcct cctggtgagc gccggcgaca gggtgaccat cacctgcaag     480
gccacccaga ccgtgagcaa cgacgtggcc tggtaccagc agaagcccgg ccagagccct     540
aagctgctga tctactacgc cagcaacagg tacacaggcg tgcccgacag gttcaccggc     600
accggctacg gcaccgactt caccttcacc atcagcacag tgcaggccga ggacctggcc     660
gtgtacttct gccagcagga ctacaccagc ccctacacct tcggaggcgg caccaagctg     720
gagatcaag                                                             729

<210> SEQ ID NO 14
<211> LENGTH: 3833
<212> TYPE: DNA
<213> ORGANISM: Artificial Sequence
<220> FEATURE:
<223> OTHER INFORMATION: Gal4UAS CD147-CAR

<400> SEQUENCE: 14
ggagcactgt cctccgaacg tcggagcact gtcctccgaa cgtcggagca ctgtcctccg      60
aacgtcggag cactgtcctc cgaacggagc atgtcctccg aacgtcggag cactgtcctc     120
cgaacgacta gttaggcgtg tacggtggga ggcctatata agcagagctc gtttagtgaa     180
ccgtcagatc gcctggagac gccatccacg ctgttttgac ctccatagaa gacaccggga     240
ccgatccagc ctctcgacat tcgttggatc cacgcgtatg gagtttgggc tgagctggct     300
ttttcttgtg gctattttaa aaggtgtcca gtgcgtcgac gagatgaagc tggaagagag     360
cggcggcgga ctggtgcagc ccggcggcag catgaagctg agctgcgtgg cctccggctt     420
caccttcagc aactactgga tgaactgggt gagacagtcc cccgaaaagg gcctggagtg     480
ggtggcccag atcagactga agtcctacaa ctacgccacc cactacgccg agagcgtgaa     540
gggcagattc accatctcca gggacgactc caagtcctcc gtgtacctgc agatgaacaa     600
cctgagagcc gaggacaccg gcatctacta ctgcaccccc gatggcagcg actattgggg     660
ccagggcaca acactcaccg tgagctccgg cggcggaggc agcggcggcg cggcagcggg     720
cggcggcggc tccggcggag cggcagcag catcgtgatg acccagaccc ccaagttcct     780
cctggtgagc gccggcgata gggtgaccat tacctgcaag gcctcccagt ccgtgagcaa     840
cgatgtggcc tggtaccagc agaagcccgg ccagagccct aagctgctga tctactacgc     900
cagcaacagg tacacaggcg tgcccgacag gtttaccggc tccggctacg gcaccgactt     960
caccttcacc atcagcacag tgcaggccga ggacctggcc gtgtacttct gccagcagga    1020
ctacaccagc ccctacacct tcggaggcgg caccaagctg gagatcaaga cgtacgtcac    1080
cgtctcttca caggatcccg ccgagcccaa atctcctgac aaaactcaca catgcccacc    1140
gtgcccagca cctgaactcc tggggggacc gtcagtcttc ctcttccccc caaaacccaa    1200
ggacaccctc atgatctccc ggacccctga ggtcacatgc gtggtggtgg acgtgagcca    1260
```

-continued

```
cgaagaccct gaggtcaagt tcaactggta cgtggacggc gtggaggtgc ataatgccaa    1320
gacaaagccg cgggaggagc agtacaacag cacgtaccgt gtggtcagcg tcctcaccgt    1380
cctgcaccag gactggctga atggcaagga gtacaagtgc aaggtctcca acaaagccct    1440
cccagccccc atcgagaaaa ccatctccaa agccaaaggg cagccccgag aaccacaggt    1500
gtacaccctg cccccatccc gggatgagct gaccaagaac caggtcagcc tgacctgcct    1560
ggtcaaaggc ttctatccca gcgacatcgc cgtggagtgg gagagcaatg ggcaaccgga    1620
gaacaactac aagaccacgc ctcccgtgct ggactccgac ggctccttct tcctctacag    1680
caagctcacc gtggacaaga gcaggtggca gcaggggaac gtcttctcat gctccgtgat    1740
gcatgaggct ctgcacaacc actacacgca gaagagcctc tccctgtctc cgggtaaaaa    1800
agatcccaaa tttttgggtgc tggtggtggt tggtggagtc ctggcttgct atagcttgct    1860
agtaacagtg gcctttatta ttttctgggt gaggagtaag aggagcaggc tcctgcacag    1920
tgactacatg aacatgactc cccgccgccc cgggcccacc cgcaagcatt accagcccta    1980
tgccccacca cgcgacttcg cagcctatcg ctccaaacgg ggcagaaaga aactcctgta    2040
tatattcaaa caaccattta tgagaccagt acaaactact caagaggaag atggctgtag    2100
ctgccgattt ccagaagaag aagaaggagg atgtgaactg agagtgaagt tcagcaggag    2160
cgcagacgcc cccgcgtacc agcagggcca gaaccagctc tataacgagc tcaatctagg    2220
acgaagagag gagtacgatg ttttggacaa gagacgtggc cgggaccctg agatgggggg    2280
aaagccgaga aggaagaacc ctcaggaagg cctgtacaat gaactgcaga aagataagat    2340
ggcggaggcc tacagtgaga ttgggatgaa aggcgagcgc cggaggggca aggggcacga    2400
tggcctttac cagggtctca gtacagccac caaggacacc tacgacgccc ttcacatgca    2460
ggccctgccc cctcgctaac atatgttgac ttgcggccgc aactcccacc tgcaacatgc    2520
gtgactgact gaggccgcga ctctagagtc gacctgcatc taggcgccgg aattagatct    2580
ctcgaggtta acgaattcta ccgggtaggg gaggcgcttt cccaaggca gtctggagca    2640 tgcgctttag cagccccgct gggcacttgg cgctacacaa gtggcctctg cctcgcaca    2700 cattccacat ccaccggtag gcgccaaccg gctccgttct ttggtggccc cttcgcgcca    2760
ccttctactc ctcccctagt caggaagttc ccccccgccc cgcagctcgc gtcgtgcagg    2820
acgtgacaaa tggaagtagc acgtctcact agtctcgtgc agatggacag caccgctgag    2880
caatggaagc gggtaggcct ttggggcagc ggccaatagc agctttgctc cttcgctttc    2940
tgggctcaga ggctgggaag gggtgggtcc ggggcgggc tcaggggcgg gctcaggggc    3000
ggggcgggcg cccgaaggtc ctccggaggc ccggcattct gcacgcttca aaagcgcacg    3060
tctgccgcgc tgttctcctc ttcctcatct ccgggccttt cgacctgcag cccaagctta    3120
ccatggtgag caagggcgag gaggataaca tggccatcat caaggagttc atgcgcttca    3180
aggtgcacat ggagggctcc gtgaacggcc acgagttcga gatcgagggc gagggcgagg    3240
gccgccccta cgagggcacc cagaccgcca agctgaaggt gaccaagggt ggccccctgc    3300
ccttcgcctg ggacatcctg tcccctcagt tcatgtacgg ctccaaggcc tacgtgaagc    3360
accccgccga catccccgac tacttgaagc tgtccttccc cgagggcttc aagtgggagc    3420
gcgtgatgaa cttcgaggac ggcggcgtgg tgaccgtgac ccaggactcc tccctgcagg    3480
acggcgagtt catctacaag gtgaagctgc gcggcaccaa cttcccctcc gacggccccg    3540
taatgcagaa gaagaccatg ggctgggagg cctcctccga gcggatgtac cccgaggacg    3600
```

```
gcgccctgaa gggcgagatc aagcagaggc tgaagctgaa ggacggcggc cactacgacg    3660
ctgaggtcaa gaccacctac aaggccaaga agcccgtgca gctgcccggc gcctacaacg    3720
tcaacatcaa gttggacatc acctcccaca acgaggacta caccatcgtg gaacagtacg    3780
aacgcgccga gggccgccac tccaccggcg gcatggacga gctgtacaag taa           3833
```

```
<210> SEQ ID NO 15
<211> LENGTH: 12221
<212> TYPE: DNA
<213> ORGANISM: Artificial Sequence
<220> FEATURE:
<223> OTHER INFORMATION: pHR_Gal4UAS-CD147-CAR-pGK_mCherry vector

<400> SEQUENCE: 15
```

```
cgataccgtc gaccaaggca gctgtagatc ttagccactt tttaaaagaa aaggggggac      60
tggaagggct aattcactcc caacgaagac aagatctgct ttttgcttgt actgggtctc     120
tctggttaga ccagatctga gcctgggagc tctctggcta actagggaac ccactgctta     180
agcctcaata aagcttgcct tgagtgcttc aagtagtgtg tgcccgtctg ttgtgtgact     240
ctggtaacta gagatccctc agaccctttt agtcagtgtg gaaaatctct agcagcatct     300
agaattaatt ccgtgtattc tatagtgtca cctaaatcgt atgtgtatga tacataaggt     360
tatgtattaa ttgtagccgc gttctaacga caatatgtac aagcctaatt gtgtagcatc     420
tggcttactg aagcagaccc tatcatctct ctcgtaaact gccgtcagag tcggtttggt     480
tggacgaacc ttctgagttt ctggtaacgc cgtcccgcac ccggaaatgg tcagcgaacc     540
aatcagcagg gtcatcgcta gccagatcct ctacgccgga cgcatcgtgg ccggcatcac     600
cggcgccaca ggtgcggttg ctggcgccta tatcgccgac atcaccgatg gggaagatcg     660
ggctcgccac ttcgggctca tgagcgcttg tttcggcgtg ggtatggtgg caggccccgt     720
ggccggggga ctgttgggcg ccatctcctt gcatgcacca ttccttgcgg cggcggtgct     780
caacggcctc aacctactac tgggctgctt cctaatgcag gagtcgcata agggagagcg     840
tcgaatggtg cactctcagt acaatctagc tctgatgccg catagttaag ccagccccga     900
cacccgccaa cacccgctga cgcgccctga cgggcttgtc tgctcccggc atccgcttac     960
agacaagctg tgaccgtctc cgggagctgc atgtgtcaga ggttttcacc gtcatcaccg    1020
aaacgcgcga cgaaagggg cctcgtgata cgcctatttt tataggttaa tgtcatgata    1080
ataatggttt cttagacgtc aggtggcact tttcggggaa atgtgcgcgg aacccctatt    1140
tgtttatttt tctaaataca ttcaaatatg tatccgctca tgagacaata accctgataa    1200
atgcttcaat aatattgaaa aaggaagagt atgagtattc aacatttccg tgtcgccctt    1260
attccctttt ttgcggcatt ttgccttcct gtttttgctc acccagaaac gctggtgaaa    1320
gtaaaagatg ctgaagatca gttgggtgca cgagtgggtt acatcgaact ggatctcaac    1380
agcggtaaga tccttgagag ttttcgcccc gaagaacgtt ttccaatgat gagcactttt    1440
aaagttctgc tatgtggcgc ggtattatcc cgtattgacg ccgggcaaga gcaactcggt    1500
cgccgcatac actattctca gaatgacttg gttgagtact caccagtcac agaaaagcat    1560
cttacggatg gcatgacagt aagagaatta tgcagtgctg ccataaccat gagtgataac    1620
actgcggcca acttacttct gacaacgatc ggaggaccga aggagctaac cgcttttttg    1680
cacaacatgg gggatcatgt aactcgcctt gatcgttggg aaccggagct gaatgaagcc    1740
ataccaaacg acgagcgtga caccacgatg cctgtagcaa tggcaacaac gttgcgcaaa    1800
ctattaactg gcgaactact tactctagct tcccggcaac aattaataga ctggatggag    1860
```

-continued

```
gcggataaag ttgcaggacc acttctgcgc tcggcccttc cggctggctg gtttattgct   1920
gataaatctg gagccggtga gcgtgggtct cgcggtatca ttgcagcact ggggccagat   1980
ggtaagccct cccgtatcgt agttatctac acgacgggga gtcaggcaac tatggatgaa   2040
cgaaatagac agatcgctga gataggtgcc tcactgatta agcattggta actgtcagac   2100
caagtttact catatatact ttagattgat ttaaaacttc attttttaatt taaaaggatc   2160 taggtgaaga tcctttttga taatctcatg accaaaatcc cttaacgtga gttttcgttc   2220
cactgagcgt cagaccccgt agaaaagatc aaaggatctt cttgagatcc tttttttctg   2280
cgcgtaatct gctgcttgca aacaaaaaaa ccaccgctac cagcggtggt ttgtttgccg   2340
gatcaagagc taccaactct ttttccgaag gtaactggct tcagcagagc gcagatacca   2400
aatactgtcc ttctagtgta gccgtagtta ggccaccact tcaagaactc tgtagcaccg   2460
cctacatacc tcgctctgct aatcctgtta ccagtggctg ctgccagtgg cgataagtcg   2520
tgtcttaccg ggttggactc aagacgatag ttaccggata aggcgcagcg tcgggctga   2580 acgggggggtt cgtgcacaca gcccagcttg gagcgaacga cctacaccga actgagatac   2640
ctacagcgtg agctatgaga aagcgccacg cttcccgaag ggagaaaggc ggacaggtat   2700
ccggtaagcg gcagggtcgg aacaggagag cgcacgaggg agcttccagg gggaaacgcc   2760
tggtatcttt atagtcctgt cgggtttcgc cacctctgac ttgagcgtcg attttttgtga   2820 tgctcgtcag ggggcggag cctatggaaa aacgccagca acgcggcctt tttacggttc   2880
ctggcctttt gctggccttt tgctcacatg ttctttcctg cgttatcccc tgattctgtg   2940
gataaccgta ttaccgcctt tgagtgagct gataccgctc gccgcagccg aacgaccgag   3000
cgcagcgagt cagtgagcga ggaagcggaa gagcgcccaa tacgcaaacc gcctctcccc   3060
gcgcgttggc cgattcatta atgcagctgt ggaatgtgtg tcagttaggg tgtggaaagt   3120
ccccaggctc cccagcaggc agaagtatgc aaagcatgca tctcaattag tcagcaacca   3180
ggtgtggaaa gtccccaggc tccccagcag gcagaagtat gcaaagcatg catctcaatt   3240
agtcagcaac catagtcccg cccctaactc cgcccatccc gcccctaact ccgcccagtt   3300
ccgcccattc tccgccccat ggctgactaa ttttttttat ttatgcagag gccgaggccg   3360
cctcggcctc tgagctattc cagaagtagt gaggaggctt ttttggaggc ctaggctttt   3420
gcaaaaagct tggacacaag acaggcttgc gagatatgtt tgagaatacc actttatccc   3480
gcgtcaggga gaggcagtgc gtaaaaagac gcggactcat gtgaaatact ggtttttagt   3540
gcgccagatc tctataatct cgcgcaacct attttcccct cgaacacttt ttaagccgta   3600
gataaacagg ctgggacact tcacatgagc gaaaaataca tcgtcacctg ggacatgttg   3660
cagatccatg cacgtaaact cgcaagccga ctgatgcctt ctgaacaatg gaaaggcatt   3720
attgccgtaa gccgtggcgg tctgtaccgg gtgcgttact ggcgcgtgaa ctgggtattc   3780
gtcatgtcga taccgtttgt atttccagct acgatcacga caaccagcgc gagcttaaag   3840
tgctgaaacg cgcagaaggc gatggcgaag gcttcatcgt tattgatgac ctggtggata   3900
ccggtggtac tgcggttgcg attcgtgaaa tgtatccaaa agcgcacttt gtcaccatct   3960
tcgcaaaacc ggctggtcgt ccgctggttg atgactatgt tgttgatatc ccgcaagata   4020
cctggattga acagccgtgg gatatgggcg tcgtattcgt cccgccaatc tccggtcgct   4080
aatcttttca acgcctggca ctgccgggcg ttgttctttt taacttcagg cgggttacaa   4140
tagtttccag taagtattct ggaggctgca tccatgacac aggcaaacct gagcgaaacc   4200
```

```
ctgttcaaac cccgctttaa acatcctgaa acctcgacgc tagtccgccg ctttaatcac    4260
ggcgcacaac cgcctgtgca gtcggccctt gatggtaaaa ccatccctca ctggtatcgc    4320
atgattaacc gtctgatgtg gatctggcgc ggcattgacc cacgcgaaat cctcgacgtc    4380
caggcacgta ttgtgatgag cgatgccgaa cgtaccgacg atgatttata cgatacggtg    4440
attggctacc gtggcggcaa ctggatttat gagtgggccc cggatctttg tgaaggaacc    4500
ttacttctgt ggtgtgacat aattggacaa actacctaca gagatttaaa gctctaaggt    4560
aaatataaaa tttttaagtg tataatgtgt taaactactg attctaattg tttgtgtatt    4620
ttagattcca acctatggaa ctgatgaatg ggagcagtgg tggaatgcct ttaatgagga    4680
aaacctgttt tgctcagaag aaatgccatc tagtgatgat gaggctactg ctgactctca    4740
acattctact cctccaaaaa agaagagaaa ggtagaagac cccaaggact ttccttcaga    4800
attgctaagt tttttgagtc atgctgtgtt tagtaataga actcttgctt gctttgctat    4860
ttacaccaca aaggaaaaag ctgcactgct atacaagaaa attatggaaa aatattctgt    4920
aacctttata agtaggcata acagttataa tcataacata ctgtttttte ttactccaca    4980 caggcataga gtgtctgcta ttaataacta tgctcaaaaa ttgtgtacct ttagcttttt    5040
aatttgtaaa ggggttaata aggaatattt gatgtatagt gccttgacta gagatcataa    5100
tcagccatac cacatttgta gaggttttac ttgctttaaa aaacctccca cacctcccc    5160 tgaacctgaa acataaaatg aatgcaattg ttgttgttaa cttgtttatt gcagcttata    5220
atggttacaa ataaagcaat agcatcacaa atttcacaaa taaagcattt ttttcactgc    5280
attctagttg tggtttgtcc aaactcatca atgtatctta tcatgtctgg atcaactgga    5340
taactcaagc taaccaaaat catcccaaac ttcccacccc atccctatt accactgcca    5400 attacctagt ggtttcattt actctaaacc tgtgattcct ctgaattatt ttcattttaa    5460
agaaattgta tttgttaaat atgtactaca aacttagtag ttggaagggc taattcactc    5520
ccaaagaaga caagatatcc ttgatctgtg gatctaccac acacaaggct acttccctga    5580
ttagcagaac tacacaccag ggccagggt cagatatcca ctgacctttg gatggtgcta    5640
caagctagta ccagttgagc cagataaggt agaagaggcc aataaaggag agaacaccag    5700
cttgttacac cctgtgagcc tgcatgggat ggatgacccg gagagagaag tgttagagtg    5760
gaggtttgac agccgcctag catttcatca cgtggcccga gagctgcatc cggagtactt    5820
caagaactgc tgatatcgag cttgctacaa gggactttcc gctggggact ttccagggag    5880
gcgtggcctg ggcgggactg gggagtggcg agccctcaga tcctgcatat aagcagctgc    5940
tttttgcctg tactgggtct ctctggttag accagatctg agcctgggag ctctctggct    6000
aactagggaa cccactgctt aagcctcaat aaagcttgcc ttgagtgctt caagtagtgt    6060
gtgcccgtct gttgtgtgac tctggtaact agagatccct cagacccttt tagtcagtgt    6120
ggaaaatctc tagcagtggc gcccgaacag ggacttgaaa gcgaaaggga accagagga    6180 gctctctcga cgcaggactc ggcttgctga gcgcgcacg gcaagaggcg aggggcggcg    6240
actggtgagt acgccaaaaa ttttgactag cggaggctag aaggagagag atgggtgcga    6300
gagcgtcagt attaagcggg ggagaattag atcgcgatgg gaaaaaattc ggttaaggcc    6360
agggggaaag aaaaaatata aattaaaaca tatagtatgg gcaagcaggg agctagaacg    6420
attcgcagtt aatcctggcc tgttagaaac atcagaaggc tgtagacaaa tactgggaca    6480
gctacaacca tcccttcaga caggatcaga agaacttaga tcattatata atacagtagc    6540
aaccctctat tgtgtgcatc aaaggataga gataaaagac accaaggaag ctttagacaa    6600
```

-continued

```
gatagaggaa gagcaaaaca aaagtaagac caccgcacag caagcggccg gtgatcttca      6660
gacctggacg atatatatga gggacaattg gagaagtgaa ttatataaat ataaagtagt      6720
aaaaattgaa ccattaggag tagcacccac caaggcaaag agaagagtgg tgcagagaga      6780
aaaaagagca gtgggaatag gagctttgtt ccttgggttc ttgggagcag caggaagcac      6840
tatgggcgca gcgtcaatga cgctgacggt acaggccaga caattattgt ctggtatagt      6900
gcagcagcag aacaatttgc tgagggctat tgaggcgcaa cagcatctgt tgcaactcac      6960
agtctggggc atcaagcagc tccaggcaag aatcctggct gtggaaagat acctaaagga      7020
tcaacagctc ctggggattt ggggttgctc tggaaaactc atttgcacca ctgctgtgcc      7080
ttggaatgct agttggagta ataaatctct ggaacagatt tggaatcaca cgacctggat      7140
ggagtgggac agagaaatta acaattacac aagcttaata cactccttaa ttgaagaatc      7200
gcaaaaccag caagaaaaga atgaacaaga attattggaa ttagataaat gggcaagttt      7260
gtggaattgg tttaacataa caaattggct gtggtatata aaattattca taatgatagt      7320
aggaggcttg gtaggtttaa gaatagtttt tgctgtactt tctatagtga atagagttag      7380
gcagggatat tcaccattat cgtttcagac ccacctccca accccgaggg gacccgacag      7440
gcccgaagga atagaagaag aaggtggaga gagagacaga gacagatcca ttcgattagt      7500
gaacggatct cgacggtcgc aaatggcag tattcatcca caattttaaa agaaaagggg      7560
ggattggggg gtacagtgca ggggaaagaa tagtagacat aatagcaaca gacatacaaa      7620
ctaaagaatt acaaaaacaa attacaaaaa ttcaaaattt tcgggtttat tacagggaca      7680
gcagagatcc agtttggatc gataagcttg atatcgaatt cggagcactg tcctccgaac      7740
gtcggagcac tgtcctccga acgtcggagc actgtcctcc gaacgtcgga gcactgtcct      7800
ccgaacggag catgtcctcc gaacgtcgga gcactgtcct ccgaacgact agttaggcgt      7860
gtacggtggg aggcctatat aagcagagct cgtttagtga accgtcagat cgcctggaga      7920
cgccatccac gctgttttga cctccataga agacaccggg accgatccag cctctcgaca      7980
ttcgttggat ccacgcgtat ggagtttggg ctgagctggc ttttcttgt ggctattta      8040 aaaggtgtcc agtgcgtcga cgagatgaag ctggaagaga gcggcggcgg actggtgcag      8100
cccggcggca gcatgaagct gagctgcgtg gcctccggct tcaccttcag caactactgg      8160
atgaactggg tgagacagtc cccccgaaaag ggcctggagt gggtggccca gatcagactg      8220
aagtcctaca actacgccac ccactacgcc gagagcgtga agggcagatt caccatctcc      8280
agggacgact ccaagtcctc cgtgtacctg cagatgaaca acctgagagc cgaggacacc      8340
ggcatctact actgcacccc cgatggcagc gactattggg ccagggcac aacactcacc      8400 gtgagctccg gcggcggagg cagcggcggc ggcggcagcg gcggcggcgg ctccggcgga      8460
ggcggcagca gcatcgtgat gacccagacc cccaagttcc tcctggtgag cgccggcgat      8520
agggtgacca ttacctgcaa ggcctcccag tccgtgagca cgatgtggc ctggtaccag      8580 cagaagcccg gccagagccc taagctgctg atctactacg ccagcaacag gtacacaggc      8640
gtgcccgaca ggtttaccgg ctccggctac ggcaccgact tcaccttcac catcagcaca      8700
gtgcaggccg aggacctggc cgtgtacttc tgccagcagg actactccag cccctacacc      8760
ttcggaggcg gcaccaagct ggagatcaag acgtacgtca ccgtctcttc acaggatccc      8820
gccgagccca atctcctga caaaactcac acatgcccac cgtgcccagc acctgaactc      8880
ctggggggac cgtcagtctt cctcttcccc ccaaaaccca aggacaccct catgatctcc      8940
```

-continued

```
cggacccctg aggtcacatg cgtggtggtg gacgtgagcc acgaagaccc tgaggtcaag   9000
ttcaactggt acgtggacgg cgtggaggtg cataatgcca agacaaagcc gcgggaggag   9060
cagtacaaca gcacgtaccg tgtggtcagc gtcctcaccg tcctgcacca ggactggctg   9120
aatggcaagg agtacaagtg caaggtctcc aacaaagccc tcccagcccc catcgagaaa   9180
accatctcca aagccaaagg gcagccccga gaaccacagg tgtacaccct gcccccatcc   9240
cgggatgagc tgaccaagaa ccaggtcagc ctgacctgcc tggtcaaagg cttctatccc   9300
agcgacatcg ccgtggagtg ggagagcaat gggcaaccgg agaacaacta caagaccacg   9360
cctcccgtgc tggactccga cggctccttc ttcctctaca gcaagctcac cgtggacaag   9420
agcaggtggc agcaggggaa cgtcttctca tgctccgtga tgcatgaggc tctgcacaac   9480
cactacacgc agaagagcct ctccctgtct ccgggtaaaa aagatcccaa attttgggtg   9540
ctggtggtgg ttggtggagt cctggcttgc tatagcttgc tagtaacagt ggcctttatt   9600
attttctggg tgaggagtaa gaggagcagg ctcctgcaca gtgactacat gaacatgact   9660
ccccgccgcc ccgggcccac ccgcaagcat taccagccct atgccccacc acgcgacttc   9720
gcagcctatc gctccaaacg gggcagaaag aaactcctgt atatattcaa acaaccattt   9780
atgagaccag tacaaactac tcaagaggaa gatggctgta gctgccgatt ccagaagaa    9840 gaagaaggag gatgtgaact gagagtgaag ttcagcagga gcgcagacgc ccccgcgtac   9900
cagcagggcc agaaccagct ctataacgag ctcaatctag gacgaagaga ggagtacgat   9960
gttttggaca agagacgtgg ccgggaccct gagatggggg gaaagccgag aaggaagaac   10020
cctcaggaag gcctgtacaa tgaactgcag aaagataaga tggcggaggc ctacagtgag   10080
attgggatga aaggcgagcg ccggaggggc aaggggcacg atggccttta ccagggtctc   10140
agtacagcca ccaaggacac ctacgacgcc cttcacatgc aggccctgcc ccctcgctaa   10200
catatgttga cttgcggccg caactcccac ctgcaacatg cgtgactgac tgaggccgcg   10260
actctagagt cgacctgcat ctaggcgcgc gaattagatc tctcgaggtt aacgaattct   10320
accgggtagg ggaggcgctt ttcccaaggc agtctggagc atgcgcttta gcagccccgc   10380
tgggcacttg cgctacaca agtggcctct ggcctcgcac acattccaca tccaccggta   10440
ggcgccaacc ggctccgttc tttggtggcc ccttcgcgcc accttctact cctcccctag   10500
tcaggaagtt cccccccgcc ccgcagctcg cgtcgtgcag gacgtgacaa atggaagtag   10560
cacgtctcac tagtctcgtg cagatggaca gcaccgctga gcaatggaag cgggtaggcc   10620 tttgggcag cggccaatag cagctttgct ccttcgcttt ctgggctcag aggctgggaa   10680
ggggtgggtc cgggggcggg ctcaggggcg gctcaggg cggggcgggc gcccgaaggt   10740
cctccggagg cccggcattc tgcacgcttc aaaagcgcac gtctgccgcg ctgttctcct   10800
cttcctcatc tccgggcctt tcgacctgca gcccaagctt accatggtga gcaagggcga   10860
ggaggataac atggccatca tcaaggagtt catgcgcttc aaggtgcaca tggagggctc   10920
cgtgaacggc cacgagttcg agatcgaggg cgagggcgag ggccgcccct acgagggcac   10980
ccagaccgcc aagctgaagg tgaccaaggg tggcccctg cccttcgcct gggacatcct   11040
gtcccctcag ttcatgtacg gctccaaggc ctacgtgaag caccccgccg acatccccga   11100
ctacttgaag ctgtccttcc ccgagggctt caagtgggag cgcgtgatga acttcgagga   11160
cggcggcgtg gtgaccgtga cccaggactc ctccctgcag gacggcgagt tcatctacaa   11220
ggtgaagctg cgcggcacca acttcccctc cgacggcccc gtaatgcaga agaagaccat   11280
gggctgggag gcctcctccg agcggatgta ccccgaggac ggcgccctga agggcgagat   11340
```

```
caagcagagg ctgaagctga aggacggcgg ccactacgac gctgaggtca agaccaccta   11400
caaggccaag aagcccgtgc agctgcccgg cgcctacaac gtcaacatca agttggacat   11460
cacctcccac aacgaggact acaccatcgt ggaacagtac gaacgcgccg agggccgcca   11520
ctccaccggc ggcatggacg agctgtacaa gtaaagcggc cgcgactcta gagtcgacct   11580
gcaggcatgc aagcttgcag gcatgcaagc ttgatatcaa gcttatcgat aatcaacctc   11640
tggattacaa aatttgtgaa agattgactg gtattcttaa ctatgttgct ccttttacgc   11700
tatgtggata cgctgcttta atgcctttgt atcatgctat tgcttcccgt atggctttca   11760
ttttctcctc cttgtataaa tcctggttgc tgtctcttta tgaggagttg tggcccgttg   11820
tcaggcaacg tggcgtggtg tgcactgtgt ttgctgacgc aacccccact ggttggggca   11880
ttgccaccac ctgtcagctc ctttccggga ctttcgcttt ccccctccct attgccacgg   11940
cggaactcat cgccgcctgc cttgcccgct gctggacagg ggctcggctg ttgggcactg   12000
acaattccgt ggtgttgtcg gggaaatcat cgtcctttcc ttggctgctc gcctgtgttg   12060
ccacctggat tctgcgcggg acgtccttct gctacgtccc ttcggccctc aatccagcgg   12120
accttccttc ccgcggcctg ctgccggctc tgcggcctct tccgcgtctt cgccttcgcc   12180
ctcagacgag tcggatctcc ctttgggccg cctccccgca t                       12221
```

```
<210> SEQ ID NO 16
<211> LENGTH: 819
<212> TYPE: DNA
<213> ORGANISM: Artificial Sequence
<220> FEATURE:
<223> OTHER INFORMATION: GPC3-CAR

<400> SEQUENCE: 16
atggagtttg gtttaagctg ctgtttttta gtggccattt taaagggcgt gcagtgcgag    60
caaaaactta tctctgaaga ggacctcgtc gaccaagttc agctgcagca gagcggagcc   120
gaactggtga cacccggcgc tagcgtgaag ctgtcttgta aggctagcgg ctacaccttc   180
accgactacg agatgcattg ggtcaagcag accccccgttc acggtttaaa gtggatcggc   240
gctctcgatc ctaagactgg tgacaccgcc tacagccaga agttcaaagg caaggccact   300
ttaaccgccg acaagtccag cagcaccgct tacatggagc tgaggagcct cacctccgag   360
gacagcgccg tgtattactg cacaaggttc tacagctaca catactgggg ccaaggtaca   420
ctggtgaccg tgagcgctgg cggcggaggc tccggtggcg gcggcagcgg aggcggcggt   480
tctgacgtgg tgatgaccca gacaccttta agcctccccg tttctttagg cgatcaagct   540
agcatctctt gtcgttcctc ccagtcttta gtgcactcca acggcaacac ctatttacac   600
tggtatctgc agaagcccgg ccagagcccc aagctgctga tctacaaggt cagcaatagg   660
ttcagcggcg tgcccgatcg ttttagcgga agcggcagcg gcaccgactt cactttaaaa   720
atctctcgtg tggaggccga agatttaggc gtgtacttt gttcccagaa cacccacgtg    780
ccccccacat tcggctccgg aaccaagctg gagattaag                          819
```

```
<210> SEQ ID NO 17
<211> LENGTH: 87
<212> TYPE: DNA
<213> ORGANISM: Artificial Sequence
<220> FEATURE:
<223> OTHER INFORMATION: GAL4-VP64
```

-continued

<400> SEQUENCE: 17
gcctggagac gccatccacg ctgttttgac ctccatagaa gacaccggga ccgatccagc      60
ctctcgacat tcgttggatc cacgcgt      87

<210> SEQ ID NO 18
<211> LENGTH: 65
<212> TYPE: DNA
<213> ORGANISM: Artificial Sequence
<220> FEATURE:
<223> OTHER INFORMATION: Synthetic oligonucleotide primer

<400> SEQUENCE: 18
tgcgtcgacg agcagaaact catctctgaa gaggatctgg agatgaagct ggaagagagc      60
ggcgg      65

<210> SEQ ID NO 19
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 19
ggcaccaagc tggagatcaa gatcctggac tacagcttca cagg      44

<210> SEQ ID NO 20
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 20
cctgtgaagc tgtagtccag gatcttgatc tccagcttgg tgcc      44

<210> SEQ ID NO 21
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 21
ctaacgcgtt catgatccga gcatgtccag gtcaaag      37

<210> SEQ ID NO 22
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 22
tcgacattcg ttggatccgc cagcatggag tttggtttaa gc      42

<210> SEQ ID NO 23
<211> LENGTH: 55
<212> TYPE: DNA
<213> ORGANISM: Artificial Sequence
<220> FEATURE:
<223> OTHER INFORMATION: Synthetic oligonucleotide primer -continued

<400> SEQUENCE: 23
cggctccgga accaagctgg agattaagga gcccaaatct cctgacaaaa ctcac        55

<210> SEQ ID NO 24
<211> LENGTH: 55
<212> TYPE: DNA
<213> ORGANISM: Artificial Sequence
<220> FEATURE:
<223> OTHER INFORMATION: Synthetic oligonucleotide primer

<400> SEQUENCE: 24
gtgagttttg tcaggagatt tgggctcctt aatctccagc ttggttccgg agccg        55

<210> SEQ ID NO 25
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 25
tagaattcgt taacctcgag ttagcgaggg ggcagggcct gc                      42

<210> SEQ ID NO 26
<211> LENGTH: 64
<212> TYPE: DNA
<213> ORGANISM: Artificial Sequence
<220> FEATURE:
<223> OTHER INFORMATION: Synthetic oligonucleotide primer

<400> SEQUENCE: 26
tgccaccatg gcaatggagt ttggtttaag ctggctgttt ttagtggcca ttttaaaggg   60
cgtg                                                               64

<210> SEQ ID NO 27
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 27
caggatacgc gtcttaatct ccagcttggt tccgg                             35

<210> SEQ ID NO 28
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 28
ttaagacgcg tatcctggac tacagcttca caggtg                            36

<210> SEQ ID NO 29
<211> LENGTH: 33
<212> TYPE: DNA
<213> ORGANISM: Artificial Sequence
<220> FEATURE:
<223> OTHER INFORMATION: Synthetic oligonucleotie primer

<400> SEQUENCE: 29
tcccgctcga gtcatgatcc gagcatgtcc agg                               33

-continued

```
<210> SEQ ID NO 30
<211> LENGTH: 61
<212> TYPE: DNA
<213> ORGANISM: Artificial Sequence
<220> FEATURE:
<223> OTHER INFORMATION: Synthetic oligonucleotide primer

<400> SEQUENCE: 30
tcgttggatc cacgcgtcgt acgttaatta acccgggcat atgttgactt gcggccgcaa      60
c                                                                     61

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 31
ccattgctca gcggtgctg                                                  19

<210> SEQ ID NO 32
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 32
gatccacgcg tatggagttt gggctgagct ggc                                  33

<210> SEQ ID NO 33
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 33
gtcaacatat gttagcgagg gggcagggcc tgcatg                               36

<210> SEQ ID NO 34
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 34
ctagactgcc atggagtttg ggctgagctg                                      30

<210> SEQ ID NO 35
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 35
gacggtgacg tacgtcttga tctccagctt ggtg                                 34

<210> SEQ ID NO 36
<211> LENGTH: 21
<212> TYPE: DNA
<213> ORGANISM: Artificial Sequence
```

<220> FEATURE:
<223> OTHER INFORMATION: VH CDR1 of CD147 scFv

<400> SEQUENCE: 36
ggcttcacct tcagcaacta c                                              21

<210> SEQ ID NO 37
<211> LENGTH: 24
<212> TYPE: DNA
<213> ORGANISM: Artificial Sequence
<220> FEATURE:
<223> OTHER INFORMATION: VH CDR2 of CD147 scFv

<400> SEQUENCE: 37
agactgaagt cctacaacta cgcc                                          24

<210> SEQ ID NO 38
<211> LENGTH: 12
<212> TYPE: DNA
<213> ORGANISM: Artificial Sequence
<220> FEATURE:
<223> OTHER INFORMATION: VH CDR3 of CD147 scFv

<400> SEQUENCE: 38
gatggcagcg ac                                                       12

<210> SEQ ID NO 39
<211> LENGTH: 33
<212> TYPE: DNA
<213> ORGANISM: Artificial Sequence
<220> FEATURE:
<223> OTHER INFORMATION: VL CDR1 of CD147 scFv

<400> SEQUENCE: 39
aaggcctccc agtccgtgag caacgatgtg gcc                                33

<210> SEQ ID NO 40
<211> LENGTH: 21
<212> TYPE: DNA
<213> ORGANISM: Artificial Sequence
<220> FEATURE:
<223> OTHER INFORMATION: VL CDR2 of CD147 scFv

<400> SEQUENCE: 40
tacgccagca acaggtacac a                                             21

<210> SEQ ID NO 41
<211> LENGTH: 27
<212> TYPE: DNA
<213> ORGANISM: Artificial Sequence
<220> FEATURE:
<223> OTHER INFORMATION: VL CDR3 of CD147 scFv

<400> SEQUENCE: 41
cagcaggact actccagccc ctacacc                                       27

<210> SEQ ID NO 42
<211> LENGTH: 7
<212> TYPE: PRT
<213> ORGANISM: Artificial Sequence
<220> FEATURE:
<223> OTHER INFORMATION: VH CDR1 of CD147 scFv

<400> SEQUENCE: 42

Gly Phe Thr Phe Ser Asn Tyr
1               5

-continued

```
<210> SEQ ID NO 43
<211> LENGTH: 8
<212> TYPE: PRT
<213> ORGANISM: Artificial Sequence
<220> FEATURE:
<223> OTHER INFORMATION: VH CDR2 of CD147 scFv

<400> SEQUENCE: 43

Arg Leu Lys Ser Tyr Asn Tyr Ala
1               5

<210> SEQ ID NO 44
<211> LENGTH: 4
<212> TYPE: PRT
<213> ORGANISM: Artificial Sequence
<220> FEATURE:
<223> OTHER INFORMATION: VH CDR3 of CD147 scFv

<400> SEQUENCE: 44

Asp Gly Ser Asp
1

<210> SEQ ID NO 45
<211> LENGTH: 11
<212> TYPE: PRT
<213> ORGANISM: Artificial Sequence
<220> FEATURE:
<223> OTHER INFORMATION: VL CDR1 of CD147 scFv

<400> SEQUENCE: 45

Lys Ala Ser Gln Ser Val Ser Asn Asp Val Ala
1               5                   10

<210> SEQ ID NO 46
<211> LENGTH: 7
<212> TYPE: PRT
<213> ORGANISM: Artificial Sequence
<220> FEATURE:
<223> OTHER INFORMATION: VL CDR2 of CD147 scFv

<400> SEQUENCE: 46

Tyr Ala Ser Asn Arg Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: VL CDR3 of CD147 scFv

<400> SEQUENCE: 47

Gln Gln Asp Tyr Ser Ser Pro Tyr Thr
1               5
```